US009889184B2

(12) United States Patent
Heath et al.

(10) Patent No.: US 9,889,184 B2
(45) Date of Patent: Feb. 13, 2018

(54) ANTI-PATHOGEN SYSTEMS

(71) Applicant: Hexima Limited, Melbourne (AU)

(72) Inventors: Robyn Louise Heath, Northcote (AU); Marilyn Anne Anderson, Keilor (AU); Nicole Louise van der Weerden, Coburg (AU); James Anthony McKenna, Pascoe Vale South (AU); Simon Poon, Brunswick West (AU)

(73) Assignee: Hexima Limited, Melbourne (AU)

( * ) Notice: Subject to any disclaimer, the term of this patent is extended or adjusted under 35 U.S.C. 154(b) by 692 days.

(21) Appl. No.: 13/839,745

(22) Filed: Mar. 15, 2013

(65) Prior Publication Data

US 2013/0267459 A1 Oct. 10, 2013

Related U.S. Application Data

(63) Continuation-in-part of application No. 12/535,443, filed on Aug. 4, 2009, now abandoned.

(60) Provisional application No. 61/086,444, filed on Aug. 5, 2008.

(51) Int. Cl.
| *C12N 15/82* | (2006.01) |
| *A61K 38/56* | (2006.01) |
| *A01N 65/00* | (2009.01) |
| *A01N 65/38* | (2009.01) |
| *C07K 14/415* | (2006.01) |
| *C07K 14/81* | (2006.01) |

(52) U.S. Cl.
CPC .............. *A61K 38/56* (2013.01); *A01N 65/00* (2013.01); *A01N 65/385* (2013.01); *C07K 14/415* (2013.01); *C07K 14/8139* (2013.01); *C12N 15/8279* (2013.01); *C12N 15/8282* (2013.01)

(58) Field of Classification Search
None
See application file for complete search history.

(56) References Cited

U.S. PATENT DOCUMENTS

| 4,767,777 A | 8/1988 | Bass et al. |
| 5,482,928 A | 1/1996 | De Bolle et al. |
| 5,538,525 A | 7/1996 | Broekaert et al. |
| 5,689,043 A | 11/1997 | Broekaert et al. |
| 6,031,153 A | 2/2000 | Ryals et al. |
| 6,121,436 A | 9/2000 | Liang et al. |
| 6,147,281 A | 11/2000 | Garcia-Olmedo et al. |
| 6,215,048 B1 | 4/2001 | Liang et al. |
| 6,316,407 B1 | 11/2001 | Liang et al. |
| 6,329,504 B1 | 12/2001 | Liang et al. |
| 6,512,166 B1 | 1/2003 | Harman et al. |
| 6,605,698 B1 | 8/2003 | van Amerongen et al. |
| 6,653,280 B2 | 11/2003 | Liang et al. |
| 6,677,503 B1 | 1/2004 | Bidney et al. |
| 6,680,424 B2 | 1/2004 | Atkinson et al. |
| 6,770,750 B2 | 8/2004 | Oh et al. |
| 6,806,074 B2 | 10/2004 | Anderson et al. |
| 6,855,865 B2 | 2/2005 | Famodu et al. |
| 6,864,068 B2 | 3/2005 | Rees et al. |
| 6,911,577 B2 | 6/2005 | Simmons et al. |
| 6,916,970 B2 | 7/2005 | Liang et al. |
| 7,041,877 B2 | 5/2006 | Anderson et al. |
| 7,238,781 B2 | 7/2007 | Famodu et al. |
| 7,297,840 B2 | 11/2007 | Anderson et al. |
| 7,462,695 B2 | 12/2008 | Dunse et al. |
| 7,544,861 B2 | 6/2009 | Anderson et al. |
| 8,252,898 B2 | 8/2012 | Anderson et al. |
| 8,722,968 B2 | 5/2014 | Anderson et al. |
| 2002/0144306 A1 | 10/2002 | Liang et al. |
| 2003/0217382 A1 | 11/2003 | Anderson et al. |
| 2004/0064850 A1 | 4/2004 | Liang et al. |
| 2004/0073971 A1 | 4/2004 | Bidney et al. |
| 2004/0111761 A1 | 6/2004 | Bidney et al. |
| 2005/0058689 A1 | 3/2005 | McDaniel |
| 2005/0273881 A1 | 12/2005 | Simmons et al. |
| 2006/0150276 A1 | 7/2006 | Anderson et al. |
| 2007/0197474 A1 | 8/2007 | Clinton et al. |
| 2007/0277263 A1 | 11/2007 | Anderson et al. |
| 2008/0134367 A1 | 6/2008 | Anderson et al. |
| 2009/0069545 A1 | 3/2009 | Anderson et al. |
| 2009/0083880 A1 | 3/2009 | Anderson et al. |
| 2009/0093880 A1 | 4/2009 | Justin |
| 2009/0197809 A1 | 8/2009 | Anderson et al. |
| 2010/0068762 A1 | 3/2010 | Craik et al. |
| 2010/0095408 A1 | 4/2010 | Heath et al. |
| 2010/0218280 A1 | 8/2010 | Anderson et al. |
| 2013/0263326 A1 | 10/2013 | Heath et al. |
| 2013/0269059 A1 | 10/2013 | Heath et al. |
| 2014/0208461 A1 | 7/2014 | Anderson et al. |

(Continued)

FOREIGN PATENT DOCUMENTS

| EP | 0120516 | 10/1984 |
| WO | 93/04586 | 3/1993 |

(Continued)

OTHER PUBLICATIONS

Girard et al. New Phytologist (2007), vol. 173, pp. 841-851.*
Bartlett et al. (2002) "The strobilurin fungicides," Pest Manag. Sci. 58:649-662.
Dong et al. (2005) "Interacting Proteins and Differences in Nuclear Transport Reveal Specific Functions for the NAP1 Family Proteins in Plants," Plant Physiol. 138:1446-1456.
Lay et al. (2003) "The Three-dimensional Solution Structure of NaD1, a New Floral Defensin from Nicotiana alata and its Application to a Homology Model of the Crop Defense Protein alfAFP," J. Mol. Biol. 325:175-188.
Ryals et al. (1996) "Systemic Acquired Resistance," The Plant Cell. 8:1809-1819.

(Continued)

*Primary Examiner* — Medina A Ibrahim
(74) *Attorney, Agent, or Firm* — Knobbe, Martens, Olson & Bear, LLP

(57) ABSTRACT

Provided is a system for protecting plants from attack by pests, including pathogens such as fungi. Specifically, a plant defensin is provided in conjunction with a protease inhibitor protects a plant from pest attack or reduces severity of an attack.

7 Claims, 46 Drawing Sheets

(56) References Cited

U.S. PATENT DOCUMENTS

| | | | |
|---|---|---|---|
| 2015/0067917 A1 | 3/2015 | Heath et al. | |
| 2015/0237860 A1 | 8/2015 | Anderson et al. | |

FOREIGN PATENT DOCUMENTS

| | | |
|---|---|---|
| WO | 97/37024 | 10/1997 |
| WO | 98/00023 | 1/1998 |
| WO | 00/11175 | 3/2000 |
| WO | 00/11196 | 3/2000 |
| WO | 00/68405 | 11/2000 |
| WO | 00/78983 | 12/2000 |
| WO | 01/009174 | 2/2001 |
| WO | 01/009175 | 2/2001 |
| WO | 01/067865 | 9/2001 |
| WO | 04/001012 | 12/2003 |
| WO | 04/054366 | 7/2004 |
| WO | 04/072239 | 8/2004 |
| WO | 07/006079 | 1/2007 |
| WO | 07/110686 | 10/2007 |
| WO | 09/094719 | 8/2009 |

OTHER PUBLICATIONS

Terras et al. (1993) "Synergistic Enhancement of the Antifungal Activity of Wheat and Barley Thionins by Radish and Oilseed Rape 2S Albumins and by Barley Trypsin Inhibitors," Plant Physiol. 103:1311-1319.

van der Weerden et al. (May 2007) "Defining the Molecular Interactions of Plant Defensin with Fungal Pathogen," In; The 10th IUBMB Conference and 36th Annual Meeting of SBBq, Abstract Publication.

Wijaya et al. (2000) "Defense proteins from seed of Cassia fistula include a lipid transfer protein homologue and a protease inhibitory plant defensing," Plant Science. 159:243-255.

Prosecution history for U.S. Appl. No. 12/535,443, filed Aug. 4, 2009 (downloaded Aug. 21, 2013), last document dated Aug. 1, 2013, 93 pp.

Prosecution history for related U.S. Appl. No. 12/362,657, filed Jan. 30, 2009 (downloaded Aug. 21, 2013), last document dated Mar. 13, 2013, 85 pp.

U.S. Appl. No. 13/837,472, filed Mar. 15, 2013, including Preliminary Amendment filed Jun. 14, 2013, 85 pp.

U.S. Appl. No. 13/838,291, filed Mar. 15, 2013, including Preliminary Amendment filed Jun. 14, 2013, 86 pp.

International Search Report for International Application No. PCT/AU2009/000106, dated Mar. 20, 2009.

Abad et al. (Jul. 21, 1996) "Antifungal Activity of Tobacco Osmotin has Specificity and Involves Plasma Membrane Permeabilization," Plant Sci. 118(1):11-23.

Abraham et al. (2006) "Structural and Functional Diversity Within the Cystatin Gene Family of *Hordeum vulgare*," J Exp Bot 57:4245-4255.

Alcouloumre et al. (Dec. 1993) "Fungal Properties of Defensin NP-1 and Activity Against *Crytococcus neoformans* In Vitro,"Antimicrob. Agents Chemother. 37(12):2628-2632.

Alexander et al. (Aug. 1993) "Increased Tolerance to Two Oomycete Pathogens in Transgenic Tobacco Expressing Pathogenesis-Related Protein 1a," Proc. Nat. Acad. Sci. USA 90:7327-7331.

Almeida et al. (2000) "Characterization of Two Novel Defense Peptides from Pea (*Pisum sativum*) Seeds," Arch Biochem Biophys 378:278-286.

Aluru et al. (Jul. 6, 1999) "Capsicum Chinese Putative Gamma-Thionin Precursor, mRNA", GenBank Nucleotide Accession No. AF128239.1.

Anderson et. al. (Nov. 1983) "Isolation of a Genomic Clone for Bovine Pancreatic Trypsin Inhibitor by Using a Unique-Sequence Synthetic DNA Probe," Proc. Nat. Acad. Sci. USA 80:6838-6842.

Baker et al. (2005) "Using Deubiquitylating Enzymes as Research Tools," Methods in Enzymology 398:540-554.

Balandin et al. (2005) "A Protective Role for the Embryo Surrounding Region of the Maize Endosperm, as Evidenced by the Characterization of *ZmESR-6*, a Defensin Gene Specifically Expressed in this Region," Plant Mol Biol 58:269-282.

Beck et al. (1993) "Environmental Release Permits," Bio/Technology 11:1524-1528.

Bevan et al. (1983) "Structure and Transcription of Nopaline Synthase Gene Region of T-DNA," Nucleic Acids Res 11(2):369-385.

Bjork et al. (1996) "Importance of the Second Hairpin Loop of Cystatin C for Proteinase Binding.Characterization of the Interaction of Trp-106 Variants of the Inhibitor with Cysteine Proteinases," Biochemistry 35:10720-10726.

Broekaert et al. (1990) "An Automated Quantitative Assay for Fungal Growth Inhibition," FEMS Microbiol. Lett. 69:55-59.

Catanzariti et al. (2004) "An Efficient System for High-Level Expression and Easy Purification of Authentic Recombinant Proteins," Protein Science 13:1331-1339.

Chen et al. (2005) "Cloning and Characterization of a Plant Defensin VaD1 from Azuki Bean," J. Agric Food Chem 53:982-988.

De Samblanx et al. (Jan. 10, 1997) "Mutational Analysis of a Plant Defensin from Radish (*Raphanus sativus* L.) Reveals Two Adjacent Sites Important for Antifungal Activity," J. Biol. Chem. 272(2):1171-1179.

De Vos et al. (Mar. 1985) "Three-Dimensional Structure of Thaumatin I, an Intensely Sweet Protein," Proc. Nat. Acad. Sci. USA 82:1406-1409.

Del Sorbo et al. (2000) "Fungal Transporters Involved in Efflux of Natural Toxic Compounds and Fungicides," Fungal Genet. Biol. 30:1-15.

Dunse et al. (Aug. 24, 2010) "Coexpression of Potato Type I and II Proteinase Inhibitors Gives Cotton Plants Protection Against Insect Damage in the Field," Proc. Nat. Acad. Sci. USA 107(34):15011-15015.

Ekengren et al. (Nov. 1999) "*Drosophila* cecropin as an Antifungal Agent," Insect Biochem. Mol. Biol. 29(11):965-972.

Epand et al. (2006) "Role of Membrane Lipids in the Mechanism of Bacterial Species Selective Toxicity by Two α/β-Antimicrobial Peptides," Biochim. Biophys. Acta 1758:1343-1350.

Gorlach et al. (Apr. 1996) "Benzothiadiazole, a Novel Class of Inducers of Systemic Acquired Resistance, Activates Gene Expression and Disease Resistance in Wheat," Plant Cell 8:629-643.

Graham et al. (Jul. 2004) "Computational Identification and Characterization of Novel Genes from Legumes," Plant Physiol. 135:1179-1197.

Greco et al. (1995) "The Search for Synergy: a Critical Review from a Response Surface Perspective," Pharmacol. Rev. 47:331-385.

Gu et al. (1992) "A Flower-Specific cDNA Encoding a Novel Thionin in Tobacco," Mol. Gen. Genet 234:89-96.

Hanks et al. (2005) "Defensin Gene Family in *Medicago truncatula*: Structure, Expression and Induction by Signal Molecules," Plant Mol Biol 58:385-399.

Harrison et al. (1997) "An Antimicrobial Peptide from the Australian Native *Hardenbergia violacea* Provides the First Functionally Characterised Member of a Subfamily of Plant Defensins," Aust J Plant Phys 24:571-578.

Heath et al. (1997) "Proteinase Inhibitors from *Nicotiana alate* Enhance Plant Resistance to Insect Pests," J. Insect Physiol 43(9):833-842.

Herrera-Estrella et al. (1983) "Chimeric Genes as Dominant Selectable Markers in Plant Cells," EMBO J 2(6):987-995.

Janssen et al. (2003) "Structure of *Petunia hybrida* Defensin 1, a Novel Plant Defensin with Five Disulfide Bonds," Biochemistry 42(27):8214-8222.

Johnson et al. (2005) "Maturation of the Floral Defensin of *Nicotiana alate*," ASPB/ComBio 2005, Adelaide, Sep. 25-29, 2005 (Joint meeting).

Johnson et al. (2006) "The C-Terminal Propeptide Governs Vacuolar Deposition of the *Nicotiana alate* Floral Defensin" Lorne 2006, Feb. 5-9, 2006.

Joshi et al. (1998) "Cysteine Protease Inhibitor from Pearl Millet: A New Class of Antifungal Protein," Biochem. Biophys. Res Comm. 246:382-387.

(56) References Cited

OTHER PUBLICATIONS

Kim et al. (Aug. 2001) "Internalization of Tenecin 3 by a Fungal Cellular Process is Essential for its Fungicidal Effect on *Candida albicans*," Eur. J. Biochem. 268(16):4449-4458.
Klee et al. (1985) "Vectors for Transformation of Higher Plants," Bio/Technology 3:637-642.
Klis et al. (2002) "Dynamics of Cell Wall Structure in *Saccharomyces cerevisiae*," FEMS Microbiol. Rev. 26:239-256.
Kragh et al. (1995) "Characterization and Localization of New Antifungal Cysteine-Rich Proteins From *Beta vulgaris*," Mol Plant Microbe Interact 8(3):424-434.
Ladokhin et al. (2001) "Detergent-Like Permeabilization of Anionic Lipid Vesicles by Melittin," Biochim. Biophys. Acta 1514:253-260.
Ladokhin et al. (Apr. 1997) "Sizing Membrane Pores in Lipid Vesicles by Leakage of Co-Encapsulated Markers: Pore Formation by Melittin," Biophys. J. 72:1762-1766.
Lay et al. (2005) "Defensins—Components of the Innate Immune System in Plants," Curr. Prot. Pept. Sci. 6:85-101.
Lay et al. (Mar. 2003) "Isolation and Properties of Floral Defensins from Ornamental Tobacco and Petunia," Plant Physiol. 131:1283-1293.
Lee et al. (1999) "A Novel Two-Chain Proteinase Inhibitor Generated by Circularization of a Multidomain Precursor Protein," Nature Structure Biology 6(6):526-530.
Leiter et al. (Jun. 2005) "Antifungal Protein PAF Severely Affects the Integrity of the Plasma Membrane of *Aspergillus nidulans* and Induces an Apoptosis-Like Phenotype," Antimicrob. Agents Chemother. 49(6):2445-2453.
Li et. al. (Jul. 30, 1999) "*N. tabacum* mRNA for defensin," GenBank Nucleotide Accession No. X99403.1.
Lin et al. (Aug. 1, 2007) "Structure-Based Protein Engineering for α-Amylase Inhibitory Activity of Plant Defensin." Proteins: Structure, Function, Bioinformatics 68:530-540.
Lobo et al. (Jan. 6, 2007) "Antifungal *Pisum sativum* Defensin 1 Interacts with *Neurospora crassa* Cyclin F Related to the Cell Cycle," Biochemistry 46(4):987-996.
Lou et al. (May 2004) "Nitrogen Supply Influences Herbivore-Induced Direct and Indirect Defenses and Transcriptional Responses in *Nicotiana attenuata*," Plant Physiol. 135:496-506.
Martinez et al. (2003) "Inhibition of Plant-Pathogenic Fungi by the Barley Cystatin Hv-CPI (Gene Icy) Is Not Associated with Its Cysteine-Proteinase Inhibitory Properties," Molecular Plant-Microbe Interactions 16:876-883.
Marton et al. (2010) "Nontransgenic Genome Modification in Plant Cells," Plant Physiology 154:1079-1087.
Massonneau et al. (2005) "Maize Cystatins Respond to Developmental Cues, Cold Stress and Drought," Biochim Biophys Acta: (BBA)—Gene Structure and Expression 1729:186-199.
Matsuzaki, K. (1999) "Why and How are Peptide-Lipid Interactions Utilized for Self-Defense? Magainins and Tachyplesins as Archetypes," Biochem. Biophys. Acta 1462:1-10.
Matsuzaki et al. (1995) "Molecular Basis of Membrane Selectivity of an Antimicrobial Peptide, Magainin 2," Biochemistry 34(10):3423-3429.
McKenna et al. (2004) "The Potential of the Antifungal Protein NaD1 for Control of Fusarium Wilt and Verticillium Wilt," 12th Australian Cotton Conference, Aug. 10-12, 2004, 1 page.
Melo et al. (2001) "Synthesis and Hydrolysis by Cysteine and Serine Proteases of Short Internally Quenched Fluorogenic Peptides," Analytical Biochemistry 293:71-77.
Meyer et al. (1996) "Fruit-Specific Expression of a Defensin-Type Gene Family in Bell Pepper," Plant Physiol. 112:615-622.
Nielsen et al. (1994) "The Three-Dimensional Solution Structure by $^1$H NMR of a 6-kDa Proteinase Inhibitor Isolated from the Stigma of *Nicotiana alate*," J Mol Biol 242:231-243.
Nielsen et al. (1995) "Structures of a Series of 6-kDa Trypsin Inhibitors Isolated from the Stigma of *Nicotiana alate*," Biochemistry 34:14304-14311.
Nilsson et al. (Aug. 25, 1989) "Short Cytoplasmic Sequences Serve as Retention Signals for Transmembrane Proteins in the Endoplasmic Reticulum," Cell 58:707-718.
Oberparleiter et al. (Nov. 2003) "Active Internalization of the *Penicillium chrysogenum* Antifungal Protein PAF in Sensitive Aspergilli," Antimicrob. Agents Chemother. 47(11):3598-3601.
Oerke et. al. (2004) "Safeguarding Production—Losses in Major Crops and the Role of Crop Protection," Crop Protection 23:275-285.
Osborn et al. (1995) "Isolation and Characterization of Plant Defensins from Seeds of Asteraceae, Fabaceae, Hippocastanaceae and Saxifragaceae," FEBS Lett 368: 257-262.
Park et al. (2002) "Characterization of a Stamen-Specific cDNA Encoding a Novel Plant Defensin in Chinese Cabbage," Plant Molecular Biology 50:57-68.
Pelegrini et al. (2005) "Plant γ-Thionins: Novel Insights on the Mechanism of Action of a Multi-Functional Class of Defense Proteins," Int. J. Biochem. Cell Biol. 37:2239-2253.
Pervieux et al. (2004) "A Spruce Defensin Showing Strong Antifungal Activity and Increased Transcript Accumulation After Wounding and Jasmonate Treatments," Physiol Mol Plant Pathol 64:331-341.
Potter et al. (1993) "Regulation of a Hevein-Like Gene in *Arabidopsis*," Mol. Plant Microbe. Interact. 6:680-685.
Ramamoorthy et al. (Oct. 1, 2007) "Glucosylceramide Synthase is Essential for Alfalfa Defensin-Mediated Growth Inhibition but not for Pathogenicity of *Fusarium graminearum*," Mol. Microbiol. 66(3):771-786.
Reimann et al. (Jun. 2005) "Inhibition of Efflux Transporter-Mediated Fungicide Resistance in *Pyrenophora tritici-repentis* by a Derivative of 4'-Hydroxyflavone and Enhancement of Fungicide Activity," Appl. Environ. Microbiol. 71(6):3269-3275.
Richer, D.L. (1987) "Synergism—A Patent View," Pest. Sci. 19:309-315.
Rogers et al. (1998) "Gene Transfer in Plants: Production of Transformed Plants Using Ti Plasmid Vectors," Methods for Plant Mol. Biol. 423-436.
Saitoh et al. (2001) "Production of Antimicrobial Defensin in *Nicotiana benthamiana* with a Potato Virus X Vector," Mol Plant Microbe Interact 14(2):111-115.
Salzman et al. (2004) "Inorganic Cations Mediate Plant PR5 Protein Antifungal Activity Through Fungal Mnn1- and Mnn4-Regulated Cell Surface Glycans," Mol. Plant Microbe Interact. 17(0):780-788.
Schirra et al. (2001) "The Solution Structure of C1-T1, a Two-Domain Proteinase Inhibitor Derived from a Circular Precursor Protein from *Nicotiana alata*," J Mol Biol 306:69-79.
Segura et al. (1998) "Novel Defensin Subfamily from Spinach (*Spinacia oleracea*)," FEBS Lett 435:159-162.
Silverstein et al. (Jun. 2005) "Genome Organization of More Than 300 Defensin-Like Genes in *Arabidopsis*," Plant Physiol. 138:600-610.
Stotz et al. (2009) "Plant Defensins: Defense, Development and Application," Plant Signaling & Behavior 4(11):1010-1012.
Tabe et al. (1995) "A Biotechnological Approach to Improving the Nutritive Value of Alfalfa," Journal of Animal Science 73:2752-2759.
Tamura et al. (May 7, 2007) "MEGA4: Molecular Evolutionary Genetics Analysis (MEGA) Software Version 4.0," Mol. Biol. Evol. 24:1596-1599.
Terras et al. (1992) "Analysis of Two Novel Classes of Plant Antifungal Proteins from Radish (*Raphanus sativus L.*) Seeds," J Biol Chem 267(22):15301-15309.
Theis et al. (2005) "New Insights into the Target Site and Mode of Action of the Antifungal Protein of *Aspergillus giganteus*,"Res Microbiol 156:47-56.
Theis et al. (2004) "Antifungal Proteins: Targets, Mechanisms and Prospective Applications," Cell Mol. Life Sci. 61:437-455.
Theis et al. (Feb. 2003) "The Antifungal Protein from *Aspergillus giganteus* Causes Membrane Permeabilization," Antimicrob. Agents Chemother. 47(2):588-593.
Thevissen et al. (2005) "Fungal Sphingolipids as Targets for the Development of Selective Antifungal Therapeutics," Curr. Drug Targets 6:923-928.

(56) References Cited

OTHER PUBLICATIONS

Thevissen et al. (Feb. 6, 2004) "Defensins from Insects and Plants Interact with Fungal Glucosylceramides," J. Biol. Chem. 279(6):3900-3905.

Thevissen et al. (Aug. 15, 2000) "A Gene Encoding a Sphingolipid Biosynthesis Enzyme Determines the Sensitivity of *Saccharomyces cerevisiae* to an Antifungal Plant Defensin from Dahlia (*Dahlia merckii*)," Proc. Nat. Acad. Sci. USA 97(17):9531-9536.

Thevissen et al. (2000) "Specific Binding Sites for an Antifungal Plant Defensin from Dahlia (*Dahlia merckii*) on Fungal Cells are Required for Antifungal Activity," Mol. Plant. Microbe. Interact. 13(1):54-61.

Tregear et al. (2002) "Characterization of a Defensin Gene Expressed in Oil Palm Inflorescences: Induction During Tissue Culture and Possible Association with Epigenetic Somaclonal Variation Events," J Experimental Botany 53(373):1387-1396.

Turk et. al. (1991) "The Cystatins: Protein Inhibitors of Cysteine Proteinases" FEBS Lett. 285:213-219.

Urdangarin et al. (2000) "A Defensin Gene Expressed in Sunflower Inflorescence," Plant Physiol Biochem 38(3):253-258.

Van Der Weerden et al. (2004) "Permeabilization of Fungal Membranes by a Floral Defensin," ComBio 2004 Perth, Sep. 26-30, 2004, 1 page.

Van Der Weerden et al. (2005) "Defensin Gets Under Fungal 'Skin'," MPG2005, Melbourne, 1 page.

Van Der Weerden et al. (2005) "A Fluorescence Approach to Studying the Interaction of Defensin with Fungi," ComBio2005 Adelaide, Sep. 25-29, 2005, 1 page.

Van Der Weerden et al. (Mar. 13, 2008) "The Plant Defensin, NaD1, Enters the Cytoplasm of *Fusarium Oxysporum* Hyphae," J. Biol. Chem. 283(21):14445-14452.

Williams et al. (1979) "Screening for Resistance to Blackleg of Crucifers in the Seedling Stage," Proceedings of Ecucarpia Cruciferae Conference, Wageningen, The Netherlands, pp. 164-170.

Non-Final Office Action corresponding to U.S. Appl. No. 13/838,291, dated Feb. 4, 2016.

Non-Final Office Action corresponding to U.S. Appl. No. 14/535,111, dated Jan. 14, 2016.

Lay, F.T., et al., Isolation and Properties of Floral Defensins From Ornamental Tobacco and Petunia, Plant Physiology 131:1283-1293, Mar. 2003.

\* cited by examiner

```
           10        20        30        40        50        60        70        80        90
    ....|....|....|....|....|....|....|....|....|....|....|....|....|....|....|....|....|....|
NaCys1  MATISQIREAGGSENSLEINDLARFAVDEHNKKQMALLEFGKVVNVKEQVVAQTMYYITLEATEGGKKAYEAKVWVKPWDNFKQLEDFKLIGDAASA
NaCys2  MANIGQIREAGGSENSLEINDLARFAVDGHNKKQNALLEFRKVVNVKEQVVAQTMYYITLEATEGGKKKAYEAKVWVKPWDNFKQLEDFKLIGDAASA
NaCys3  MANIGQIREAGGSENSLEINDLARFAVDEHNKKQNALLEFGKVVNVKEQVVAQIMYYITLEATEGGKKKAYEAKVWVKPWDNFKQLEDPKLIGDAASA
NaCys4  MANIGQIREAGGSENSLEINDLARFAVDEHNKKQNALLEFGKVVNVKEQVVAQIMYYITLEATEGGNKKAYEAKVWVKPWDNFKQLEIFKLIGDAASA
        ****  *************** ****  ***** ***** ******** **** *********** ** ************ ********* ****
```

FIGURE 1A

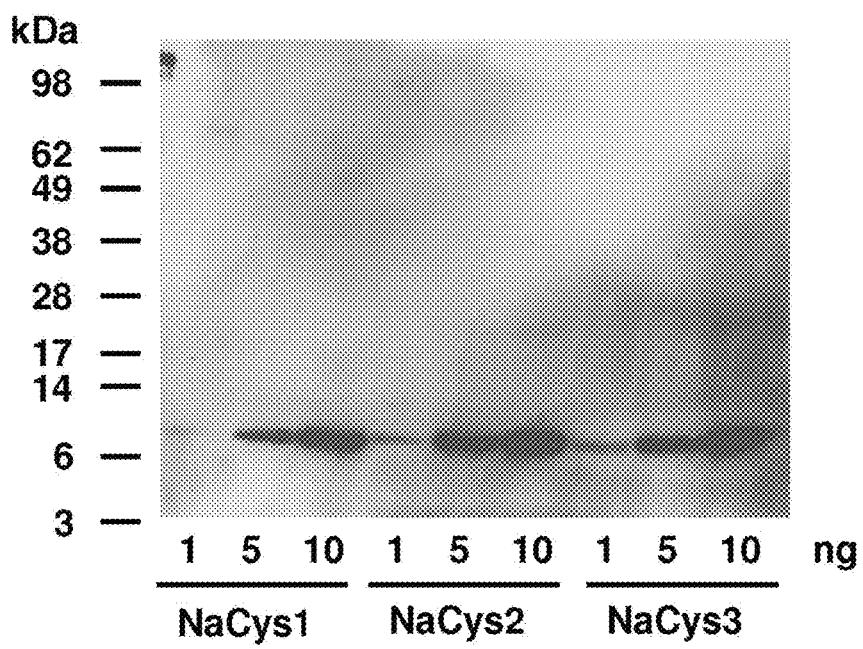

| Proteinase inhibitor | Source |
|---|---|
| NaPin1A | *Nicotiana alata* |
| NaPin1B | *Nicotiana alata* |
| StPin1A | *Solanum tuberosum* |
| CI-1B | *Hordeum vulgare* |
| CI-2 | *Hordeum vulgare* |
| At2g38870 | *Arabidopsis thaliana* |

Figure 2A

```
              10        20        30        40        50
              ....|....|....|....|....|....|....|....|....|....|
CI-1B         MRSMEGSVPKYPEPTEGSIG-ASGAKRSTPEVGMSAEKAKEIDLRDKPD
CI-2          MSSME-----KKPEGVNIGAGDRQNQKTETPELVCKSVEEAKKVILQDKPE
At2g38870     ----------MSTECPRKNSTPELTETNGDYAAVVERENPT 60        70        80
              ....|....|....|....|....|....|....|....|
CI-1B         AQIEVIPVDAMVPLDENPNEIFILVA---VARTETVG
CI-2          AQIIMLPVGTIVTIEYRIDRVRIFVDRLDNIAQVPRVE
At2g38870     VNAAVILDGSPVTADERCDEVRVFVDGNRIVVKTEKSG
```

Figure 2B

|  | uM | ppm | 0.25 uM (1.3 ppm) NaD1 | | 0.5 uM (2.6 ppm) NaD1 | |
|---|---|---|---|---|---|---|
|  |  |  | Ee | Io | Ee | Io |
| NaCys1 | 0.25 | 2.6 | 2.0 | 19.0 | 38.0 | 85.0 |
|  | 1.0 | 10.8 | -2.0 | 44.0 | 36.0 | 94.0 |
|  | 4.0 | 43.2 | -5.0 | 87.0 | 34.0 | 95.0 |
| NaCys2 | 0.25 | 2.6 | 17.0 | 23.0 | 32.0 | 93.0 |
|  | 1.0 | 10.8 | 11.0 | 21.0 | 26.0 | 98.0 |
|  | 4.0 | 43.2 | 1.0 | 86.0 | 18.0 | 92.0 |
| NaCys3 | 0.25 | 2.6 | -20.0 | 19.0 | 31.0 | 93.0 |
|  | 1.0 | 10.8 | -15.0 | 24.0 | 33.0 | 96.0 |
|  | 4.0 | 43.2 | -35.0 | 58.0 | 22.0 | 96.0 |
| NaCys4 | 0.25 | 2.6 | 8.0 | 15.0 | 57.0 | 91.0 |
|  | 1.0 | 10.8 | 6.0 | 25.0 | 56.0 | 97.0 |
|  | 4.0 | 43.2 | 3.0 | 70.0 | 55.0 | 97.0 |
| Hv-CPI6 | 0.25 | 2.8 | 17.0 | 44.0 | 59.0 | 95.0 |
|  | 1.0 | 11.1 | 15.0 | 87.0 | 58.0 | 96.0 |
|  | 4.0 | 44.3 | 15.0 | 91.0 | 76.0 | 91.0 |
| CC6 | 0.25 | 2.7 | 8.0 | 15.0 | 47.0 | 88.0 |
|  | 1.0 | 11.0 | 11.0 | 32.0 | 49.0 | 92.0 |
|  | 4.0 | 44.0 | 14.0 | 69.0 | 76.0 | 91.0 |

FIGURE 3G

| | µM | ppm | 0.25 µM (1.3 ppm) NaD1 | | 0.5 µM (2.6 ppm) NaD1 | |
|---|---|---|---|---|---|---|
| | | | Ee | Io | Ee | Io |
| BPTI | 1.54 | 10 | 1.0 | 95.0 | 55.0 | 99.0 |
| | 3.08 | 20 | 8.0 | 95.0 | 62.0 | 98.0 |
| StPin1A | 1.24 | 10 | 14.0 | 20.0 | 38.0 | 70.0 |
| | 9.9 | 86 | 3.0 | 61.0 | 28.0 | 72.0 |
| NaPin1A | 0.5 | 4 | 7.0 | 5.0 | 26.0 | 32.0 |
| | 1.0 | 8 | 4.0 | 18.0 | 23.0 | 59.0 |
| NaPin1B | 0.5 | 4 | 1.0 | -3.0 | 8.0 | 28.0 |
| | 1.0 | 8 | -3.0 | -5.0 | 4.0 | 30.0 |
| NaPI | 1.75 | 5 | 13.0 | 15.0 | 43.0 | 56.0 |
| | 3.5 | 10 | 86.0 | 92.0 | 91.0 | 98.0 |

FIGURE 4F

```
                                                        % identity    SeqID#
NaD1     1  --RECKTESNTFPGICITKPPCPRKACIS---EKFTDGHCSKILRRCLCTKPC   47
PhD1A    1  --ATCKAECPTWDGICINKGPCVKCCKAQPEKFTDGHCSKILRRCLCTKPC      49      69.2    24
Tomdef2  1  QQICKAPSQTFPGLCFMDSSCRKYCIK---EKFTGGHCSKLQRKCLCTKPC      48      62.5    22
            **:  . *:.*:  . * * .  :      **: * ****:. .*:*******
```

FIGURE 5A

|  | uM | 0.25 uM tomdef2 | | 0.5 uM tomdef2 | |
| --- | --- | --- | --- | --- | --- |
|  |  | Ee | Io | Ee | Io |
| NaCys2 | 0.5 | -2.0* | 5.1* | 21.2* | 51.1* |
|  | 2 | -13.7* | 67.5* | 12.2* | 90.8* |
|  | 4 | -17.9* | 92.7* | 9.0* | 93.4* |
| CC6 | 0.5 | 12.1 | 13.2 | 27.0 | 28.2 |
|  | 2 | 10.9* | 15.4* | 26.0* | 55.2* |
|  | 4 | 11.6* | 57.1* | 26.5* | 71.4* |
| BPTI | 0.125 | 4.8* | 22.0* | 29.4* | 99.0* |
|  | 0.5 | 0.4* | 29.2* | 26.2* | 99.3* |
|  | 1 | 1.1* | 45.4* | 26.7* | 99.3* |
| StPin1A | 0.5 | 8.1* | 14.5* | 30.7* | 44.3* |
|  | 2 | 7.0* | 27.7* | 29.9* | 84.6* |
|  | 4 | -5.1* | 51.5* | 20.8* | 98.1* |

FIGURE 5J

|  | uM | 0.25 uM PhD1A | | 0.5 uM PhD1A | |
|---|---|---|---|---|---|
|  |  | Ee | Io | Ee | Io |
| NaCys2 | 0.5 | 8.3* | 40.5* | 48.2* | 92.8* |
|  | 2 | 3.8* | 77.4* | 45.7* | 93.0* |
|  | 4 | 13.8* | 86.6* | 51.4* | 95.4* |
| CC6 | 0.5 | 28.7 | 26.5 | 50.8 | 52.1 |
|  | 2 | 30.3* | 35.1* | 51.9* | 77.9* |
|  | 4 | 30.5* | 71.6* | 52.1* | 79.2* |
| BPTI | 0.125 | 26.5* | 41.6* | 58.0* | 98.9* |
|  | 0.5 | 21.3* | 81.9* | 55.1* | 99.4* |
|  | 1 | 23.7* | 99.3* | 56.4* | 99.3* |
| StPin1A | 0.5 | 24.1* | 36.6* | 62.2* | 78.9* |
|  | 2 | 25.2* | 63.6* | 62.7* | 93.4* |
|  | 4 | 17.2 | 28.2 | 58.7 | 58.6 |

FIGURE 5K

|  | uM | 0.5 uM NaD1 | | 1 uM NaD1 | |
|---|---|---|---|---|---|
|  |  | Ee | Io | Ee | Io |
| NaCys2 | 0.5 | 22.1 | 17.3 | 23.5 | 18.7 |
|  | 2 | 16.0 | 14.6 | 17.5 | 19.3 |
|  | 4 | 9.7 | 9.0 | 11.4* | 28.4* |
| CC6 | 0.5 | 18.0 | 15.7 | 25.4 | 25.5 |
|  | 2 | 18.4 | 15.3 | 25.8 | 20.2 |
|  | 4 | 16.8 | 19.2 | 24.3 | 19.8 |
| BPTI | 0.125 | 20.2* | 35.5* | 32.6* | 67.7* |
|  | 0.5 | 21.4* | 37.0* | 33.6* | 66.8* |
|  | 1 | 21.1* | 46.0* | 33.4* | 65.7* |
| StPin1A | 0.5 | 17.0 | 14.5 | 22.4 | 28.5 |
|  | 2 | 21.2 | 24.2 | 26.4* | 34.4* |
|  | 4 | 25.2* | 38.2* | 30.1* | 48.7* |

FIGURE 6

|  | uM | 2.5 uM NaD1 | | 5 uM NaD1 | |
| --- | --- | --- | --- | --- | --- |
|  |  | Ee | Io | Ee | Io |
| NaCys2 | 0.5 | 4.1 | 5.7 | 17.9 | 14.4 |
|  | 2 | 8.1 | 3.2 | 21.3* | 36.1* |
|  | 4 | 0.4 | -0.7 | 14.7* | 63.4* |
| CC6 | 0.5 | 6.7 | 6.4 | 19.3 | 22.2 |
|  | 2 | 7.8 | 5.5 | 20.3 | 16.9 |
|  | 4 | 3.5 | 4.4 | 16.6 | 16.9 |
| BPTI | 0.125 | 6.9* | 93.6* | 18.8* | 97.4* |
|  | 0.5 | 5.9* | 94.1* | 17.8* | 97.2* |
|  | 1 | 6.2* | 94.8* | 18.2* | 95.8* |
| StPin1A | 0.5 | 9.1 | 7.9 | 17.0 | 24.1 |
|  | 2 | 19.0 | 18.5 | 26.1* | 60.7* |
|  | 4 | 42.6 | 40.2 | 47.6* | 94.7* |

FIGURE 7E

| Fungus | Protease inhibitor | Ee | Io |
|---|---|---|---|
| *Fusarium graminearum* | CI-1B (2 µM) | 25.9 | 82.1* |
| | CI-2 (2 µM) | 2.5 | 66.5* |
| | LBTI (10 µM) | 0.0 | 73.4* |
| | SBTI (10 µM) | 17.3 | 74.0* |
| | BBTI (10 µM) | 6.3 | 6.5 |
| *Colletotrichum graminicola* | CI-1B (4 µM) | 22.3 | 63.8* |
| | CI-2 (4 µM) | 59.8 | 100* |
| | LBTI (10 µM) | 16.1 | 82.6* |
| | SBTI (10 µM) | 24.1 | 23.1 |
| | NaPin1A (1.25 µM) | 52.0 | 85.2* |
| | NaPin1B (2.5 µM) | 51.8 | 75.8* |
| | BBTI (10 µM) | 26.0 | 96.6* |
| *Aspergillus niger* | CI-2 (2 µM) | 40.4 | 100* |

FIGURE 9

| Defensin | Source |
|---|---|
| HXL001 | *Zea mays* |
| HXL002 | *Triticum aestivum* |
| HXL004 | *Nicotiana benthamiana* |
| HXL007 | *Cyamopsis tetragonoloba* |
| HXL008 | *Picramnia pentandra* |

FIGURE 10A

| | | | | | |
|---|---|---|---|---|---|
| | 10 | 20 | 30 | 40 | 50 |
| HXL001 | RHCLSQSHRFKCLCMSSNMCANVQQ-TCNFPGCCKAEG-ATRKCFCKKI |
| HXL002 | RDCLSQSHKFKCACLSSSNCAAVQR-TCNFPDCCHTHN-EARKCFCKRA |
| HXL004 | RTCESQSHRFKCLCFSRSNCASVCH-TCGFNGCCR---G-FRRRCFCTRH |
| HXL005 | KMCQTTSHVFS--CVNDSGCSGSCE-KCGFAGCCD---G-VRRRCTCYKK |
| HXL007 | RTCESLADTYRCPCFTDGSCDDHCKNKEHLISCR---RN--DFRCWCTRN |
| HXL008 | KVCTKPSKFFKCLCGTDGACTTACR-KCGLHSYCQLKGFINSVCRKH |
| DmAMP1 | ELCEKASKTWSGNCGNTGHCDNQCKSWECAAHCAHVRNG-KHMCFCYFNC |

FIGURE 10B

| Defensin | Proteinase inhibitor | Ee | Io |
|---|---|---|---|
| HXL001 (2.5 µM) | At2g38870 (2 µM) | 2.3 | 36.6* |
| | HvCPI6 (2 µM) | 20.6 | 64.9* |
| | BPTI (2 µM) | 29.5 | 60.2* |
| HXL002 (1 µM) | At2g38870 (4 µM) | 22.1 | 63.5* |
| | HvCPI6 (2 µM) | 27.2 | 69.0* |
| | BPTI (4 µM) | 44.5 | 75.6* |
| HXL007 (2.5 µM) | At2g38870 (2 µM) | 55.0 | 93.8* |
| | HvCPI6 (2 µM) | 52.1 | 95.6* |
| | BPTI (2 µM) | 22.4 | 88.5* |
| HXL008 (2.5 µM) | At2g38870 (2 µM) | 19.6 | 70.5* |
| | HvCPI6 (2 µM) | 47.9 | 96.8* |
| | BPTI (2 µM) | 32.1 | 92.3* |

FIGURE 10D

| Defensin | Proteinase inhibitor | Ee | Io |
|---|---|---|---|
| HXL002 (1 µM) | BPTI (2 µM) | 4.9 | 99.4* |
| HXL007 (1 µM) | BPTI (2 µM) | 47.5 | 86.1* |
| | HvCPI6 (2 µM) | 49.5 | 90.4* |
| | At2g38870 (2 µM) | 27.2 | 77.1* |
| HXL008 (1 µM) | BPTI (1 µM) | 27.6 | 82.0* |
| | HvCPI6 (2 µM) | 22.2 | 74.6* |
| DmAMP1 (0.5 µM) | BPTI (2 µM) | 77.1 | 82.0 |
| | NaCys2 (0.5 M) | 80.0 | 93.0 |

FIGURE 10E

ANTI-PATHOGEN SYSTEMS

CROSS-REFERENCE TO RELATED APPLICATIONS

This application is a Continuation-in-Part of U.S. patent application Ser. No. 12/535,443, filed Aug. 4, 2009, which application claims benefit of U.S. Patent Application No. 61/086,444, filed on Aug. 5, 2008, both of which are incorporated herein by reference to the extent there is no inconsistency with the present disclosure.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 26612239$_{13}$ 1.TXT, the date of creation of the ASCII text file is Aug, 31, 2017, and the size of the ASCII text file is 22.8 KB.

ACKNOWLEDGEMENT OF FEDERAL FUNDING

Not applicable.

BACKGROUND

The present application relates generally to the protection of plants from plant pathogens and in particular from fungal pathogens. The present methods especially provide a multivalent approach to inhibiting pathogen infection in plants and to ameliorate damage to susceptible plants.

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Crop losses due to infection by plant pathogens such as fungal pathogens are a major problem in the agricultural industry and each year, millions of dollars are spent on the application of fungicides to curb these losses (Oerke and Dehne, 2004). There is a need to identify new anti-microbial agents and strategies for dealing with infection by pathogens such as fungi. This is particularly important given the propensity for pathogens to develop resistance.

Antimicrobial peptides have evolved to protect organisms from pathogens. Their specificity is largely dependent on the organism from which they originate, probably due to evolutionary pressure placed on these organisms by various pathogens. As such, peptides isolated from mammalian species generally exhibit a higher degree of activity toward bacterial pathogens compared to fungal pathogens, presumably due to the higher risk of infection from bacteria. In contrast, plant antimicrobial peptides generally display higher antifungal activity due to the higher risk of fungal infection faced by plants.

Plant defensins represent one class of antimicrobial peptides (reviewed by Lay and Anderson, 2005). There is a wide variety of defensins with differing spatial and temporal patterns of expression and spectra of activity.

The mechanisms underlying the specificity of these peptides remain unknown, although interactions with plasma membrane components are presumed to be involved. Since membrane permeabilization is a common activity of many antimicrobial peptides and the membrane composition of various cell types is highly variable, the presence of specific lipids is postulated in some cases to be responsible for the efficacy of antimicrobial peptides. In particular, the plasma membrane of bacterial cells contains negatively charged phospholipids in the outer layer while mammalian cells do not (Matsuzaki, 1999). These negatively charged lipids could interact with positively charged antimicrobial peptides. In support of this hypothesis, in vitro studies have demonstrated that the presence of negatively charged lipids is important for the membrane permeabilizing activity of a number of antimicrobial peptides (Matsuzaki et al, 1995; Matsuzaki, 1999; Epand et al, 2006).

Membrane permeabilization has been suggested as a mechanism of action for some plant defensins, although the mechanism of permeabilization has not been investigated. In the case of the plant defensins RsAFP2 and DmAMP1, permeabilization is proposed to involve a specific receptor on the cell surface. The presence of specific sphingolipids in the plasma membrane is also required for the activity of these defensins, possibly as binding sites (Thevissen et al, 2000; Thevissen et al, 2004; Thevissen et al, 2005; Ramamoorthy et al, 2007).

Plant pathogens induce significant plant yield loss and current strategies for pathogen control are both expensive and potentially damaging to the environment. Given the need to improve the economy of agriculture production, new strategies are required for protecting agronomic and ornamentally important plants from a range of diseases, especially fungal disease.

SUMMARY

Disclosed herein is a system for reducing damage to crops and ornamental plants caused by pathogens such as fungal agents. The traditional method of control involves application of chemical fungicides. This adds to the cost of crop and flower production. In accordance with the present disclosure, a surprising synergy is identified between plant defensins and proteinase inhibitors resulting in increased efficacy in preventing and ameliorating disease conditions in plants.

Herein is provided a system for protecting a plant from a disease associated with infection by a pathogen, the system comprising providing cells of the plant with a plant defensin and a proteinase inhibitor or a precursor or a functional homolog, analog, derivative or variant thereof of either or both. In a particular embodiment, the plant pathogen is a fungus. Reference to a "plant" or a genetically modified plant includes in one aspect, a plant and its progeny. Defensins and proteinase inhibitors include precursors or a functional homologs analogs, derivatives or variants.

The present disclosure provides inter alia, therefore, a system for protecting a plant from infection by a fungal pathogen and/or for reducing the incidence of severity of fungal pathogen-associated disease. The system encompasses a multivalent approach of using a combination of at least one defensin and one proteinase inhibitor. Unexpectedly, the combined action of a given defensin and a given proteinase inhibitor on a given fungal pathogen is synergistic, i.e. the anti-pathogen activity of the (at least) two components is greater than the sum of the inhibitory effects of either the proteinase inhibitor or the defensin acting alone when they are combined in the plant environment.

Hence, further provided is a system for protecting a plant from a disease associated with infection by a pathogen, the system comprising providing cells of the plants with a plant defensin and a proteinase inhibitor or a precursor or a functional homolog, analog, derivative or variant thereof of either or both in a synergistically effective amount to reduce infection by the pathogen.

Reference to a "system" includes a plant management system, a protocol and a method. As indicated above, in a particular embodiment, the pathogen is a fungal pathogen.

Reference to "providing cells of the plant" includes providing the defensin and the proteinase inhibitor from an exogenous source, or providing both from within the cell or providing one exogenously and one intracellularly.

The present application further contemplates the use of a plant defensin and a proteinase inhibitor or a precursor form of either or both in the manufacture of a genetically modified plant which is less susceptible to fungal infection or exhibits less fungal infection-associated damage.

In an embodiment, there is a system for protecting crop or ornamental plants from fungal disease, comprising providing to the plant a plant defensin and a proteinase inhibitor or functional homologs, analogs or variants or equivalents thereof. In this embodiment, the extent of fungal inhibition by both components is considered synergistic compared to the combined separate effects of each component alone. In one embodiment, there is synergistic inhibition of *Fusarium* species by a combination of at least one plant defensin, for example, NaD1 or an antifungal variant thereof, and at least one of various proteinase inhibitors including, but not limited to, a cysteine proteinase inhibitor from a plant or a serine proteinase inhibitor such as StPin1A (a potato type I inhibitor previously called Pot1A as described in U.S. Pat. No. 7,462,695) or Bovine Trypsin Inhibitor I-P. Any fungus individually susceptible to inhibition by each of the components of the system can be more effectively controlled by using the gombination than by either component used by itself. In an embodiment, the present methods and compositions do not extend to the combination of the permeabilizing defensin NaD1 and the proteinase inhibitor NaPI from *Nicotiana alata*. In certain embodiments, when the defensin is NaD1, the proteinase inhibitor is not NaPI, and when the protease inhibitor is NaPI, the defensin is not NaD1.

Accordingly, there is provided a genetically modified plant or progeny thereof which is resistant to fungal infection, the plant comprising cells genetically modified to produce a fungus-permeabilizing plant defensin and a proteinase inhibitor or precursor form thereof, wherein neither is produced in a cell of a plant not genetically modified and wherein if the defensin is NaD1, the proteinase inhibitor is not NaPI, and when the protease inhibitor is NaPI, the defensin is not NaD1

There is further provided a system for protecting a plant from a disease associated with infection by a fungal pathogen. The system comprises providing cells of a plant with a plant defensin and a proteinase inhibitor or a precursor (or a functional homolog, analog, derivative or variant thereof of either or both).

The multivalent approach herein comprises a plant defensin and a proteinase inhibitor acting synergistically. These components may be produced by recombinant means within a plant cell and optionally exported from or into the plant cell. Alternatively, the components may be provided to a plant cell topically such as in the form of a spray, aerosol, powder or as part of fertilizer or plant food. As indicated above, in yet another alternative, one of the defensin or the proteinase inhibitor is provided by recombinant means and the other of these components is provided exogenously.

There is contemplated a method for inhibiting fungal growth, replication, infection and/or maintenance, the method comprising exposing the fungus to a combination of a plant defensin and a proteinase inhibitor.

Again, the extent of fungal inhibition in the presence of both a defensin and a proteinase inhibitor is synergistic as compared to the sum of inhibition provided by either component in individual contact with the fungus at the same dose used for the combined exposure.

A fungus is "susceptible to inhibition" by each of the individual components of the system if it can be shown that each component individually exerts an inhibitory activity against the fungus, or the components in combination exert a combined inhibitory effect that is synergistic.

The present disclosure extends to the measurement of the effect of a component of the system on permeability of fungal cells. A substance whose location can be identified, whether inside or outside of a fungal cell, is employed. The substance is referred to herein inter alia as a "permeability indicator compound". A permeability indicator compound is one whose presence$either inside or outside of a cell, can be detectably measured by virtue of possessing a detectable property such as fluorescence, radio-label, immunological characteristic or the like. Also, a permeability indicator compound is one which under normal conditions remains extracellular, and would not be detected intracellularly unless cell permeability had been altered from the normal physiological condition of the cell. In principle an indicator of permeability could also be a compound normally retained intracellularly, only leaking out under abnormal conditions, but the former type of indicator is the more common. Examples of permeability indicator compounds that can be used to monitor movement from the extra cellular to intra cellular environment include fluorescent dyes that bind to nucleic acids such as SYTOX® Green, or propidium iodide. Other examples include FITC-labelled dextrans or an immuno-gold labelled antibody, whose location can be detected by microscopy. Fluorescently tagged defensin itself can also be used as a permeability indicator compound. Measurement of ATP released from the intra cellular environment to the extra cellular environment (as disclosed in U.S. patent application Ser. No. 12/362,657 which is incorporated herein by reference) may also be used as an indicator of permeability. The term "detectable amount" is intended to convey that differences in amount of the permeability indicator compound can be semi-quantitatively assessed, sufficient for comparison purposes. For the purpose of comparing the possible effect of a plant defensin on fungal cell permeability, the plant defensin NaD1 is used as a basis for comparison.

Embodiments herein include those where the defensin is any defensin with fungicidal and/or fungistatic activity against at least one pathogenic fungus. Examples of such anti-fungal defensins include without limitation NaD1, PhD1A, PhD2, Tomdef2, RsAFP2, RsAFP1, RsAFP3 and RsAFP4 from radish, DmAMP1 from dahlia, MsDef1, MtDef2, CtAMP1, PsD1, HsAFP1, VaD1, VrD2, ZmESR6, AhAMP1 and AhAMP4 from *Aesculus hippocatanum*, AflAFP from alfalfa, NaD2, AX1, AX2, BSD1, EGAD1, HvAMP1, JI-2, PgD1, SD2, SoD2, WT1, pI39 and pI230 from pea. Chimeric defensin molecules and/or defensin variants which retain antifungal activity can also be employed in the present system for plant protection.

Chimeric defensin molecules and/or defensin variants which retain anti-fungal activity can also be employed in the present system for plant protection. In an embodiment, the defensin is NaD1, the proteinase inhibitor is not NaPI, and when the protease inhibitor is NaPI, the defensin is not NaD1.

The present compositions and methods further contemplate the use of a plant defensin and a proteinase inhibitor or a functional homolog, analog, derivative or variant thereof of either or both in the manufacture of a system for protecting a plant or its progeny from a fungal pathogen.

Another aspect herein is directed to a topical composition comprising a fungus-permeabilizing plant defensin and a proteinase inhibitor or precursor form thereof wherein if the defensin is NaD1 then the proteinase inhibitor is not NaP and when the protease inhibitor is NaPl, the defensin is not NaD1.

Another aspect herein provides a topical anti-fungal composition comprising a fungus-permeabilizing plant defensin and a proteinase inhibitor or precursor form thereof wherein if the defensin is NaD1 then the proteinase inhibitor is not NaPl and when the protease inhibitor is NaPl, the defensin is not NaD1. In an embodiment, the anti-fungal composition is a seed coating composition.

In another aspect herein provides the use of a plant defensin and a proteinase inhibitor or a functional homolog, analog, derivative or variant thereof of either or both in the manufacture of a plant or its progeny protected from a fungal pathogen.

TABLE 1

Examples of plant defensins for use in the anti-pathogen system

| Peptide | Source | Accession number | Reference |
|---|---|---|---|
| NaD1 | Nicotiana alata | Q8GTM0 | Lay et al, 2003 |
| PhD1A | Petunia hybrida | Q8H6Q1 | Lay et al, 2003 |
| PhD2 | Petunia hybrida | Q8H6Q0 (SEQ ID NO: 45) | Lay et al, 2003 |
| RsAFP2 | Raphanus sativus | P30230 | Terras et al, 1992 |
| RsAFP1 | Raphanus sativus | P69241 | Terras et al, 1992 |
| RsAFP3 | Raphanus sativus | O24332 | Terras et al, 1992 |
| RsAFP4 | Raphanus sativus | O24331 | Terras et al, 1992 |
| DmAMP1 | Dahlia merckii | AAB34972 | Osborn et al, 1995 |
| MsDef1 | Medicago sativa | AAV85437 | Hanks et al, 2005 |
| MtDef2 | Medicago truncatula | AY313169 | Hanks et al, 2005 |
| CtAMP | Clitoria ternatea | AAB34971 | Osborn et al, 1995 |
| PsD1 | Pisum sativum | P81929 | Almeida et al, 2000 |
| HsAFP1 | Heuchera sanguinea | AAB34974 | Osborn et al, 1995 |
| VaD1 | Vigna angularis | n/a | Chen et al, 2005 |
| VrD2 | Vigna radiata | 2GL1_A | Lin et al, 2007 |
| ZmESR6 | Zea mays | CAH61275 | Balandin et al, 2005 |
| AhAMP1 | Aesculus hippocastanum | AAB34970 | Osborn et al, 1995 |
| AX1 | Beta vulgaris | P81493 | Kragh et al, 1995 |
| AX2 | Beta vulgaris | P82010 | Kragh et al, 1995 |
| BSD1 | Brassica campestris | L47901 | Park et al, 2002 |
| EGAD1 | Elaeis guineensis | AF322914 | Tregear et al 2002 |
| HvAMP1 | Hardenbergia violacea | n/a | Harrison et al, 1997 |
| JI-2 | Capsicum annuum | X95730 | Meyer et al, 1996 |
| PgD1 | Picea glauca | AY494051 | Pervieux et al, 2004 |
| SD2 | Helianthus annuus | AF178634 | Urdangarin et al, 2000 |
| SoD2 | Spinacia oleracea | P81571 | Segura et al, 1998 |
| WT1 | Wasabi japonica | BAB19054 | Saitoh et al, 2001 |
| HXL001 | Zea mays | n/a | n/a |
| HXL002 | Triticum aestivum | n/a | n/a |
| HXL004 | Nicotiana benthamiana | n/a | n/a |
| HXL007 | Cyamopsis tetragonoloba | n/a | n/a |
| HXL008 | Picramnia pentandra | n/a | n/a |

Proteinase inhibitors useful in embodiments herein include but are not limited to proteinase inhibitors from the following classes: serine-, cysteine-, aspartic- and metallo-proteinase inhibitors and carboxypeptidases.

Plants which can be protected from fungal infection by the present system include those which are susceptible to a fungus which is sensitive to a proteinase inhibitor and a plant defensin which can be expressed as transgenes in that plant or to which a composition comprising the defensin and proteinase inhibitor can be applied. A combined transgene and topical application approach is also contemplated herein. The proteinase inhibitor is generally a protein or a peptide or a chemical analog thereof. The plant can be a monocotyledonous plant, especially a plant from the Poaceae family, as well as grains, such as maize, barley, wheat, rice and the like, or a dicotyledonous plant, especially from the families Solanaceae, Brassicaceae, Malvaceae, and Fabaceae.

Infection and damage from many fungal pathogens, especially those which are filamentous fungi, can be controlled in many plant species using the present system. Examples of controllable fungal and oomycete pathogens include, but are not limited to, *Fusarium, Verticillium, Pythium, Rhizoctonia, Sclerotinia, Leptosphaeria, Phytophthora, Colletotrichum, Cercospora* and *Alternaria* species, and rust fungi. Important applications include, without being limiting, the synergistic combinations of a proteinase inhibitor and an antifungal defensin used, e.g. to protect plants from *Fusarium graminearum, Fusarium oxysporum* f. sp. *vasinfectum* (Fov), *Colletotrichum graminicola, Leptosphaeria maculans, Alternaria brassicicola, Alternaria alternata, Aspergillus nidulans, Botrytis cinerea, Cercospora beticola, Cercospora zeae maydis, Cochliobolus heterostrophus, Exserohilum turcicum, Fusarium culmorum, Fusarium oxysporum, Fusarium oxysporum* f. sp. *dianthi, Fusarium oxysporum* f. sp. *lycopersici, Fusarium solani, Fusarium pseudograminearum, Fusarium verticilloides, Gaeumannomyces graminis* var. *tritici, Plasmodiophora brassicae, Sclerotinia sclerotiorum, Stenocarpella (Diplodia) maydis, Thielaviopsis basicola, Verticillium dahliae, Ustilago zeae, Puccinia sorghi, Macrophomina phaseolina, Phialophora gregata, Diaporthe phaseolorum, Cercospora sojina, Phytophthora sojae, Rhizoctonia solani, Phakopsora pachyrhizi, Alternaria macrospora, Cercospora gossypina, Phoma exigua, Puccinia schedonnardii, Puccinia cacabata, Phymatotrichopsis omnivora, Fusarium avenaceum, Alternaria brassicae, Alternaria raphani, Erysiphe graminis* (*Blumeria graminis*), *Septoria tritici, Septoria nodorum, Mycosphaerella zeae, Rhizoctonia cerealis, Ustilago tritici, Puccinia graminis, Puccinia triticina, Tilletia indica, Tilletia caries* and *Tilletia controversa*.

Agronomic compositions comprising a plant defensin and a proteinase inhibitor (or precursor thereof) or anti-fungal homologs, analogs, variants and functional equivalents thereof are also contemplated herein.

A protocol for managing plant pathogen infection of plants is further contemplated herein comprising the manipulation of a plant environment to provide a plant defensin and a proteinase inhibitor in amounts which inhibit the pathogen.

Reference to "plant pathogen" in a particular embodiment includes a fungus and other related organisms. Generally, when the system comprises genetically modifying plants to express both a defensin and a proteinase inhibitor, the term "plant" includes its progeny. When the system comprises topically applying a combination of defensin and proteinase inhibitor, the effect is generally limited to a particular plant.

A summary of the sequence identifiers used herein is provided in Table 2. The Sequence Listing is incorporated by reference herein.

TABLE 2

Summary of sequence identifiers

| SEQ ID NOS. | | |
|---|---|---|
| 1 | NaCys1 | Nucleic acid sequence |
| 2 | NaCys1 | Amino acid sequence |
| 3 | NaCys2 | Nucleic acid sequence |
| 4 | NaCys2 | Amino acid sequence |
| 5 | NaCys3 | Nucleic acid sequence |
| 6 | NaCys3 | Amino acid sequence |
| 7 | NaCys4 | Nucleic acid sequence |
| 8 | NaCys4 | Amino acid sequence |
| 9 | StPin1A | Nucleic acid sequence |
| 10 | StPin1A | Amino acid sequence |
| 11 | NaD1 | Nucleic acid sequence |
| 12 | NaD1 | Amino acid sequence |
| 13 | Hv-CPI6 | Nucleic acid sequence |
| 14 | Hv-CPI6 | Amino acid sequence |
| 15 | CC6 | Nucleic acid sequence |
| 16 | CC6 | Amino acid sequence |
| 17 | NaPin1A | Nucleic acid sequence |
| 18 | NaPin1A | Amino acid sequence |
| 19 | NaPin1B | Nucleic acid sequence |
| 20 | NaPin1B | Amino acid sequence |
| 21 | Tomdef2 | Nucleic acid sequence |
| 22 | Tomdef2 | Amino acid sequence |
| 23 | PhD1A | Nucleic acid sequence |
| 24 | PhD1A | Amino acid sequence |
| 25 | BTIP | Amino acid sequence |
| 26 | JRF1 | Synthetic primers |
| 27 | JRF2 | Synthetic primers |
| 28 | JRR1 | Synthetic primers |
| 29 | JRF3 | Synthetic primers |
| 30 | JRF4 | Synthetic primers |
| 31 | HvCys6F | Synthetic primers |
| 32 | HvCys6R | Synthetic primers |
| 33 | CC6F | Synthetic primers |
| 34 | CC6R | Synthetic primers |
| 35 | MHvCys6F2 | Synthetic primers |
| 36 | MHvCys6F | Synthetic primers |
| 37 | MCC6 | Synthetic primers |
| 38 | CC6R2 | Synthetic primers |
| 39 | Sac2StPin1A5' | Synthetic primers |
| 40 | Pot1SalI3' | Synthetic primers |
| 41 | NaPin1Afw | Synthetic primers |
| 42 | NaPin1Arv | Synthetic primers |
| 43 | NaPin1Bfw | Synthetic primers |
| 44 | NaPin1Brv | Synthetic primers |

BRIEF DESCRIPTION OF THE FIGURES

FIGS. 1A-1E are diagrammatical representations showing FIG. 1A an alignment of the amino acid sequences of the *N. alata* cystatins NaCys1 (SEQ ID NO:2), NaCys2 (SEQ ID NO:4), NaCys3 (SEQ ID NO:6) and NaCys4 (SEQ ID NO:8). Conserved amino acids are starred. Amino acids that are essential for proteinase inhibitor activity are boxed in black. FIG. 1B an alignment of the amino acid sequences of the barley cystatin Hv-CPI6 and the maize cystatin CC6. FIG. 1C shows that the antibody raised in rabbits against the cystatin NaCys1 can detect at least 1 ng of bacterially expressed NaCys1, NaCys2 and NaCys3 on a protein blot FIG. 1D cysteine proteinase inhibitor activity of NaCys1, NaCys3 and NaCys4 on Papain and FIG. 1 E cysteine proteinase inhibitor activity of NaCys1, NaCys3 and NaCys4 on Cathepsin L.

FIGS. 2A-2C are diagrammatical representations showing FIG. 2A a table of type I proteinase inhibitors expressed and their sources. FIG. 2B is an alignment of the amino acid sequences of the type I proteinase inhibitors. FIG. 2C shows that the polyclonal antibody raised in rabbits against StPin1A (SEQ ID NO:10) can detect at least 50 ng of bacterially expressed StPin1A on a protein blot. The size of the molecular size markers is given in kDa.

FIG. 3A. Combination of NaD1 and NaCys1 (SEQ ID NO:2). FIG. 3B. Combination of NaD1 and NaCys2 (SEQ ID NO:4). FIG. 3C. Combination of NaD1 and NaCys3 (SEQ ID NO:6). FIG. 3D. Combination of NaD1 and NaCys4 (SEQ ID NO:8). FIG. 3E. Combination of NaD1 and the barley cystatin Hv-CPI6 (SEQ ID NO:14). FIG. 3F. Combination of NaD1 and the maize cystatin CC6 (SEQ ID NO:16). FIG. 3G. Comparison of the expected effect (Ee) from an additive response with the observed response (Io) in the fungal bioassays illustrated in FIGS. 3A-3F. Numbers are marked with an asterisk where synergy was obtained. FIG. 3H. Immunofluorescence micrographs showing uptake of NaCys1-FITC into fungal hyphae in the presence of NaD1. *F. graminearum* hyphae incubated with (a) no protein or (b, c & d) 4 μM FITC labelled NaCys1 for 1 h and visualised by light (left panels) and fluorescence microscopy (right panels). (b) NaCys1-FITC without NaD1 (c & d) NaCys1-FITC with NaD1 (0.5 μM). NaCys1-FITC only entered the cytoplasm of hyphae that had been treated with NaD1.

FIGS. 4A through 4F are graphical representations showing the effect of combinations of the defensin NaD1 and serine proteinase inhibitors on the growth of *Fusarium graminearum* in vitro. Fungal growth, measured as described in FIG. 3 is plotted against proteinase inhibitor concentration (μM) on the horizontal axis. The solid line connects sample results obtained in the presence of 0 μM NaD1; Dashed line: 0.25 μM NaD1; Dotted line: 0.5 μM NaD1; Dot-Dash line: 1 μM NaD1. FIG. 4A. Combination of NaD1 and Bovine Trypsin Inhibitor I-P. FIG. 4B. Combination of NaD1 and *Solanum tuberosum* Type 1 Potato Inhibitor (StPin1A). FIGS. 4C and 4D. Combinations of NaD1 and *Nicotiana alata* Type 1 Potato Inhibitors NaPin1A (SEQ ID NO:18) and NaPin1B (SEQ ID NO:20) respectively. FIG. 4E. Combinations of NaD1 and *Nicotiana alata* Proteinase Inhibitor NaPI. FIG. 4F. Comparison of the expected effect (Ee) from an additive response with the observed response (Io) in the fungal bioassays illustrated in FIGS. 4A-4E. Numbers are marked with an asterisk where synergy was obtained.

FIG. 5 illustrates that defensins apart from NaD1 can act in synergy with proteinase inhibitors to retard the growth of *Fusarium graminearum*. FIG. 5A is a sequence alignment of the NaD1, Tomdef2 (SEQ ID NO:22) and PhD1A (SEQ ID NO:24) defensins. FIGS. 5B-5E. Combinations of Tomdef2 (SEQ ID NO:22) and B. NaCys2 (SEQ ID NO:4), C. the maize cystatin CC6 (SEQ ID NO:16) D. Bovine Trypsin Inhibitor I-P (SEQ ID NO:25) and E. the *Solanum tuberosum* Type 1 Potato Inhibitor StPin1A. FIGS. 5F-5I. Combinations of the petunia defensin PhD1A and F. NaCys2, G. the maize cystatin CC6 H. Bovine Trypsin Inhibitor I-P and I. the *Solanum tuberosum* Type 1 Potato Inhibitor StPin1A. FIG. 5J-5K. Comparison of the expected effect (Ee) from an additive response with the observed response (Io) in the fungal bioassays illustrated in FIGS. 5B-5E and FIGS. 5F-5I respectively. Numbers are marked with an asterisk where synergy was obtained.

FIG. 6 is a synergy table showing the effects of combinations of the defensin NaD1 and proteinase inhibitors on the growth of *Fusarium oxysporum* f. sp. *vasinfectum* (Fov) in vitro. Fungal growth was measured by the increase in optical density at 595 nm (A595) achieved 40 hours after inoculation of the growth medium. The expected effect (Ee) from an additive response is compared with the observed response (Io) in the fungal bioassays with NaD1 (SEQ ID NO:12) in combination with NaCys2 (SEQ ID NO:4), the maize cystatin CC6 (SEQ ID NO:16) Bovine Trypsin Inhibitor I-P (SEQ ID NO:25) and the *Solanum tuberosum* Type 1 Potato Inhibitor StPin1A (SEQ ID NO:10). Numbers are marked with an asterisk where synergy was obtained.

FIGS. 7A through 7E are graphical representations showing the effects of combinations of the defensin NaD1 (SEQ ID NO:12) and proteinase inhibitors on the growth of *Colletotrichum graminicola* in vitro. Fungal growth was measured by the increase in optical density at 595 nm (A595) achieved 40 hours after inoculation of the growth medium, (vertical axis) and is plotted against proteinase inhibitor concentration (μM) on the horizontal axis. The solid line connects sample results obtained in the presence of 0 μM NaD1; Dashed line: 1.25 μM NaD1; Dotted line: 2.5 μM NaD1; Dot-Dash line: 5 μM NaD1. FIGS. 7A-7D. Combinations of NaD1 with 7A. NaCys2 (SEQ ID NO:4), 7B. the maize cystatin CC6 (SEQ ID NO:16) 7C. Bovine Trypsin Inhibitor I-P (SEQ ID NO:25) and 7D. the *Solanum tuberosum* Type 1 Potato Inhibitor StPin1A (SEQ ID NO:10). FIG. 7E. Comparison of the expected effect (Ee) from an additive response with the observed response (Io) in the fungal bioassays illustrated in FIGS. 7A-7D. Numbers are marked with an asterisk where synergy was obtained.

FIG. 9 is a synergy table showing the effects of combinations of the defensin NaD1 and proteinase inhibitors on the growth of *Fusarium graminearum, Colletotrichum gramincola* and *Aspergillus niger*. Fungal growth was measured by the increase in optical density at 595 nm (A595) achieved 40 hours after inoculation of the growth medium. The expected effect (Ee) from an additive response is compared with the observed response (Io) in the fungal bioassays with NaD1 (SEQ ID NO:12) in combination with CI-1B, CI-2, LBTI, SBTI, BBTI, NaPin1A, NaPin1B. Numbers are marked with an asterisk where synergy was obtained.

FIG. 10A-10B are diagrammatical representations showing FIG. 10A a table of defensins used and their source and FIG. 10B a sequence alignment of defensins. FIG. 10D-10E are synergy tables showing the effects of combinations of the defensins and proteinase inhibitors on the growth of FIG. 10D *Fusarium graminearu* and FIG. 10E *Colletotrichum gramincola* and *Aspergillus niger*. Fungal growth was measured by the increase in optical density at 595 nm (A595) achieved 40 hours after inoculation of the growth medium. The expected effect (Ee) from an additive response is compared with the observed response (Io) in the fungal bioassays with defensins in combination with At2g38870, HvCPI6 and BPTI. Numbers are marked with an asterisk where synergy was obtained.

DETAILED DESCRIPTION

Figure 1D:
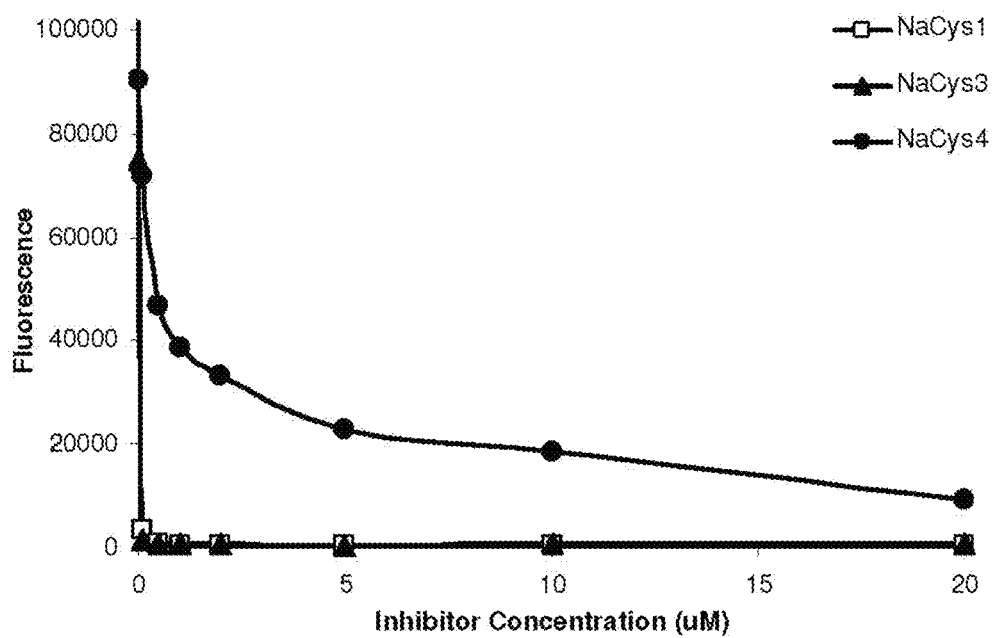

Various terms used herein have their generally accepted meaning. For clarity, the following terms are further explained and defined.

A "susceptible fungus" is a fungal strain that can be inhibited separately by each component of the system provided herein or by a combination of both components. See, e.g. FIG. 3B, when toxicity of 0.5 μM NaD1 with *Fusarium graminearum* is very low in the absence of NaCys2, but which is significantly enhanced when combined with 0.5 μM/mL NaCys2. The foregoing example also demonstrates the synergy observable when a defensin and cystatin are applied in combination. Any fungal strain that can be inhibited by NaD1, for example, can be a susceptible fungus if that fungus can also be inhibited by a cysteine or a serine proteinase inhibitor. NaD1 has been shown to inhibit growth of a representative array of filamentous fungi, including but not limited to *Fusarium graminearum, Fusarium oxysporum* f. sp. *vasinfectum* (Fov), *Colletotrichum graminicola, Leptosphaeria maculans, Alternaria brassicicola, Alternaria alternata, Aspergillus nidulans, Botrytis cinerea, Cercospora beticola, Cercospora zeae maydis, Cochliobolus heterostrophus, Exserohilum turcicum, Fusarium culmorum, Fusarium oxysporum, Fusarium oxysporum* f. sp. *dianthi, Fusarium oxysporum* f. sp. *lycopersici, Fusarium solani, Fusarium pseudograminearum, Fusarium verticilloides, Gaeumannomyces graminis* var. *tritici, Plasmodiophora brassicae, Sclerotinia sclerotiorum, Stenocarpella (Diplodia) maydis, Thielaviopsis basicola, Verticillium dahliae, Ustilago zeae, Puccinia sorghi, Macrophomina phaseolina, Phialophora gregata, Diaporthe phaseolorum, Cercospora sojina, Phytophthora sojae, Rhizoctonia solani, Phakopsora pachyrhizi, Alternaria macrospora, Cercospora gossypina, Phoma exigua, Puccinia schedonnardii, Puccinia cacabata, Phymatotrichopsis omnivora, Fusarium avenaceum, Alternaria brassicae, Alternaria raphani, Erysiphe graminis* (*Blumeria graminis*), *Septoria tritici, Septoria nodorum, Mycosphaerella zeae, Rhizoctonia cerealis, Ustilago tritici, Puccinia graminis, Puccinia triticina, Tilletia indica, Tilletia caries* and *Tilletia*. Related defensins have been shown to be active in inhibiting *Fusarium oxysporum* species, including ZmESR6, PhD1A, PhD2 and Tomdef2. Accordingly, a large number of synergistic combinations of plant defensins and proteinase inhibitors are available for plant protection against many fungal diseases, especially those caused by filamentous fungi.

Reference to "variant" includes a derivative of a particular sequence as well as a natural variant such as a polymorphic variant.

In some instances, the inhibitory effect of a given proteinase inhibitor or defensin may be below the limit of detection for a given assay, under the test conditions employed, but will be found to contribute significantly to the toxicity when combined with the other components. Greco et al, 1995 has defined different categories of synergy, according to whether one, both or neither of the two components has measurable activity when assayed in the absence of the other component. The definition adopted herein includes all such situations provided that the combined effect of the two components acting together is greater than the sum of the individual components acting alone. It will be understood that a synergistic combination of two or more components may yield greater than additive activity only under certain conditions, e.g. when one or more of the components is present at a lower concentration than is maximal for individual efficacy. A combination of components is deemed synergistic, as the term is intended herein, if there exists a set of conditions, including but not limited to concentrations, where the combined effect of the components acting together is greater than the sum of the individual components acting alone. Richer, 1987 describes a mathematical approach to establish proof of synergy. This approach uses Limpel's formula which is defined in Richer, supra 1987 and was used by Harman et al, U.S. Pat. No. 6,512,166 B1 to prove synergy between fungal cell wall degrading enzymes and fungal cell membrane affecting compounds on the growth of plant pathogenic fungi.

"Fungal inhibition" includes both fungicidal and fungistatic activity, as measured by reduction of fungal growth (or loss of viability) compared to a control. Fungal growth can be measured by many different methods known in the art. A commonly used method of measuring growth of a filamentous fungus entails germinating spores in a suitable growth medium, incubating for a time sufficient to achieve measurable growth, and measuring increased optical density in the culture after a specified incubation time. The optical density is increased with increased growth. Typically, fungal growth is necessary for pathogenesis. Therefore, inhibition of fungal growth provides a suitable indicator for protection from fungal disease, i.e. the greater the inhibition, the more effective the protection.

"Preventing infection" in the present context, means that the plants treated with the system disclosed herein, avoid pathogen infection or disease symptoms or all of the above, or exhibit reduced or minimized or less frequent pathogen infection or disease symptoms or all of the above, that are the natural outcome of the plant-pathogen interactions when compared to plants not expressing the defensin or proteinase inhibitor transgenes or treated with the defensin or proteinase inhibitor. That is to say, pathogens are prevented or reduced from causing disease and/or the associated disease symptoms. Infection and/or symptoms are reduced at least about 10%, 20%, 30%, 40%, 50, 60%, 70% or 80% or greater as compared to a plant not so treated with the system taught herein. In an alternative scenario, the system herein results in reduced sporulation of the plant pathogenic fungus which is sensitive to both the proteinase inhibitor and the defensin.

Hence, the combined action of the defensin and the proteinase inhibitor is to inhibit fungal growth, replication, infection and/or maintenance, amongst other inhibitory activities.

Plant protection (disease resistance or reduction) can be evaluated by methods known in the art. See, Uknes et al, 1993; Gorlach et al, 1996; Alexander et al, 1993. The skilled artisan will recognize that methods for determining plant infection and disease by a plant pathogen depends on the pathogen and plant being tested.

The term "plant defensin" has been well-defined in the literature (see, e.g. Lay et al, 2005). The plant defensins are small, cysteine-rich proteins having typically 45-54 amino acids. The cysteine residues form a characteristic, definitive pattern of disulfide bonds. NaD1 is a plant defensin isolated from floral tissue of *Nicotiana alata*. The amino acid and coding sequences of NaD1 are disclosed in U.S. Pat. No. 7,041,877, which is incorporated by reference herein. Other antifungal defensins are well known to the art, including, but not limited to, NaD1, PhD1A, PhD2, Tomdef2, RsAFP2, RsAFP1, RsAFP3 and RsAFP4 from radish, DmAMP1 from dahlia, MsDef1, MtDef2, CtAMP1, PsD1, HsAFP1, VaD1, VrD2, ZmESR6, AhAMP1 and AhAMP4 from *Aesculus hippocatanum*, AflAFP from alfalfa, NaD2, AX1, AX2, BSD1, EGAD1, HvAMP1, JI-2, PgD1, SD2, SoD2, WT1, pI39 and pI230 from pea. Functions of domains of plant defensins are disclosed in U.S. Published Application No. 2009-0083880, which is incorporated herein by reference. The C-terminal tail of NaD1 or another defensin having a C-terminal tail, can be incorporated via recombinant DNA technology into the structure of other defensins so as to reduce (potential) toxicity to the plant expressing the transgene. In addition, the C-terminal tail of another defensin or a vacuolar targeting sequence from another plant protein can be substituted for that of NaD1.

The term "proteinase inhibitor" is used herein to include proteins or peptides used to inhibit the activity of fungal proteinases and to protect plants from fungal disease. Chemical analogs or functional equivalents of the proteinase inhibitors are also encompassed herein. In an embodiment, the present methods and compositions do not extend to the combination of the permeabilizing defensin NaD1 and the proteinase inhibitor NaPl from *Nicotiana* alata.

The proteinase inhibitor may also be provided in a precursor form which is processed into an active form prior to being effective.

Cysteine protease inhibitors, or cystatins, are tight and reversibly binding inhibitors of cysteine proteases. They comprise a superfamily subdivided into three families: the stefins, the cystatins and the kininogens (Turk and Bode, 1991).

A "synergistic effect" occurs where two or more components within a system produce a combined effect that is greater than the sum of the individual effects of each component acting alone. The effect may be one or more of efficacy, stability, rate, and/or level of toxicity. As described herein, synergistic fungal growth inhibition measured in the combined presence of at least one plant defensin and at least one proteinase inhibitor is greater than the summed inhibition measured in the presence of a particular concentration range of each component, defensin and proteinase inhibitor, individually, under otherwise identical conditions. It will be understood that it is not necessary that a greater than additive effect be observed with every combination of concentrations of the two components in order to be deemed synergistic. The synergistic effect of two components can be observed under certain concentration combinations, but not in others.

For example, if entry into the fungal cell limits toxicity, the presence of defensin can result in synergy, especially if the concentration of proteinase inhibitor is sub-maximal with respect to inhibition. In one embodiment, the concentration of one or both of the defensin or proteinase inhibitor is sub-maximal. By the same token, synergy can be masked if one or both components is present at such a high level (maximum level) as to result in maximum observable inhibition. The general system for a defensin proteinase inhibitor combination is, therefore, termed "synergistic" because the potential for synergy is present even if synergy is not observed under all conditions. The synergy between a plant defensin and a proteinase inhibitor provides greater fungal inhibition than can be obtained by either component acting alone, for at least some dosages. In some cases a proteinase inhibitor that is not measurably effective against a particular pathogen becomes effective in the presence of defensin. Therefore, the present methods and compositions provide for increased protection of plants from fungus disease with reduced dependence on chemical fungicides. This means decreased input cost to growers, a broader spectrum of activity against plant pathogens and reduced potential for environmental damage. In addition, the selection pressure for development of fungicide-resistant fungal strains is greatly reduced, which allows for an extended commercial life as well as reduced proliferation of resistant fungus strains and reduced likelihood of emergence of multiple-resistant strains.

Hence, the system herein is useful for reducing economic loss due to fungal infection.

In one aspect herein, a system is provided for the protection of a plant from a disease associated with a pathogen such as a fungal agent, and that prevention or treatment results in decreased need for pathogenicide treatment of plants or plant parts, thus lowering costs of material, labor, and environmental pollution, or prolonging shelf-life of products (e.g. fruit, seed, and the like) of such plants. The present disclosure provides a genetically modified plant or progeny thereof which is resistant to fungal infection, the plant comprising cells genetically modified to produce a fungus-permeabilizing plant defensin and a proteinase inhibitor or precursor form thereof, wherein neither is produced in a cell of a plant not genetically modified and wherein if the defensin is NaD1, the proteinase inhibitor is not NaPI. The term "plant" includes whole plants and parts thereof, including, but not limited to, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, and the like), and progeny of same. The plants that can be protected using the system herein include higher and lower plants, including angiosperms (monocotyledonous and dicotyledonous plants), gymnosperms, ferns, horsetails, psilophytes, lycophytes, bryophytes, and multicellular algae. Plants for use in the present system can include any vascular plant, for example monocotyledons or dicotyledons or gymnosperms, including, but not limited to, alfalfa, apple, *Arabidopsis*, banana, barley, canola, castor bean, chrysanthemum, clover, cocoa, coffee, cotton, cottonseed, corn (maize), *crambe*, cranberry, cucumber, dendrobium, dio-scorea, eucalyptus, fescue, flax, gladiolus, liliacea, linseed, millet, muskmelon, mustard, oat, oil palm, oilseed rape, papaya, peanut, pineapple, ornamental plants, *Phaseolus*, potato, rapeseed, rice, rye, ryegrass, safflower, sesame, sorghum, soybean, sugarbeet, sugarcane, sunflower, strawberry, tobacco, tomato, turfgrass, wheat and vegetable crops such as lettuce, celery, broccoli, cauliflower, cucurbits, onions (including garlic, shallots, leeks, and chives); fruit and nut trees, such as apple, pear, peach, orange, grapefruit, lemon, lime, almond, pecan, walnut, hazel; vines, such as grapes, kiwi, hops; fruit shrubs and brambles, such as raspberry, blackberry, gooseberry; forest trees, such as ash, pine, fir, maple, oak, chestnut, poplar; with alfalfa, canola, castor bean, corn, cotton, *crambe*, flax, linseed, mustard, oil palm, oilseed rape, peanut, potato, rice, safflower, sesame, soybean, sugarbeet, sugarcane, sunflower, tobacco, tomato, and wheat preferred. More preferably, plants for use in the methods herein include any crop plant, for example, forage crop, oilseed crop, grain crop, fruit crop, vegetable crop, fiber crop, spice crop, nut crop, turf crop, sugar crop, beverage crop, and forest crop. The crop plant can be soybean, wheat, corn, cotton, alfalfa, canola, sugarbeet, rice, potato, tomato, onion, a legume, or a pea plant. In one aspect, reference to "plant" includes its progeny.

Reference to "fungal pathogen" includes fungi of the following phylums: Myxomycota, Plasmodiophoromycota, Hyphochytriomycota, Labyrinthulomycota, Oomycota, Chytridiomycota, Zygomycota, Ascomycota and Basidiomycota.

A "transgenic plant" refers to a plant, or seed thereof, that contains genetic material not found (i.e. "exogenous") in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e. under regulatory control of) to appropriate inducible or constitutive regulatory sequences that allow for the expression of the polypeptide. The expression cassette can be introduced into a plant by transformation or by breeding after transformation of a parent plant. An example of a suitable expression cassette is disclosed in U.S. Published Application No. 2007-0277263, the contents of which are incorporated herein by reference.

The plant or plant part for use in the present system includes plants of any stage of plant development. Conveniently, the application occurs during the stages of germination, seedling growth, vegetative growth, and reproductive growth. More particularly, applications of the present methods and compositions occur during vegetative and reproductive growth stages. The stages of vegetative and reproductive growth are also referred to herein as "adult" or "mature" plants.

Whilst the present disclosure provides a system for protecting plants from fungal infection using the synergistic action between a plant defensin and a proteinase inhibitor, it is understood that additional materials can be added to the combination to achieve even more benefit with respect to the health of the plant, for example, by incorporating a fungicidal, insecticidal or a nematicidal compound, or by utilizing more than one defensin and/or more than one proteinase inhibitor. For example, the spectrum of activity against plant pathogens can potentially be expanded by using additional agents.

The defensin and proteinase inhibitor components are conveniently supplied by the plant that is to be protected, although the present methods and compositions extend to surface sprays or seed coatings as well as in corporation in fertilizers and plant food. In certain embodiments, the plant is genetically modified to express the desired defensin and proteinase inhibitor using methods well-known in the art. In the example of cotton to be protected from disease caused by *Fusarium oxysporum* f. sp. *vasinfectum*, a cotton variety normally susceptible to Fov infection has been genetically transformed to express the defensin NaD1. The transgenic cotton variety expressing NaD1 has been shown to be significantly protected from the pathological effects of Fov infection in field trials, compared to the untransformed parent variety (U.S. Published Application No. 2009-0083880, incorporated herein by reference to the extent there is no inconsistency with the present disclosure). The results establish that Fov is susceptible to NaD1 and that the amount of a defensin, such as NaD1, that can be expressed by transgenic plants is sufficient to contribute to a synergistic effect when combined with a proteinase inhibitor as described herein.

Purified defensin protein can, if desired, be directly combined with a proteinase inhibitor as a mixture, provided they can be formulated together or sequentially by separate application means. In a further embodiment, a multiplex approach is used where one of the components is engineered to be produced by the plant and the other component is exogenously supplied.

Membrane permeabilization has been reported as the mode of action of some plant defensins, although the mechanism of permeabilization has not been investigated.

NaD1 was tested in vitro for antifungal activity against the filamentous fungi *Fusarium oxysporum* (Fov), *Verticillium dahliae*, *Thielaviopsis basicola*, *Aspergillus nidulans* and *Leptosphaeria maculans* (U.S. Pat. No. 7,041,877, U.S. Published Application No. 2009-0083880 and U.S. patent application Ser. No. 12/362,657). At 1 µM, NaD1 retarded the growth of Fov and *L. maculans* by 50% while *V. dahliae*, *T. basicola*, and *A. nidulans* were all inhibited by approximately 65%. At 5 µM NaD1, the growth of all five species was inhibited by more than 80%. These five fungal species are all members of the ascomycete phylum and are distributed among three classes in the subphylum pezizomycotiria. These fungi are agronomically important fungal pathogens. All filamentous fungi tested thus far are sensitive to inhibition by NaD1.

TABLE 3

Growth inhibitory effects of NaD1 on various cell types

| Cell type | NaD1 IC$_{50}$ (µM) |
|---|---|
| *Fusarium oxysporum* f. sp. *vasinfectum* | 1.0 |
| *Leptosphaeria maculans* | 0.80 |
| *Aspergillus nidulans* | 0.80 |
| *Verticillium dahliae* | 0.75 |
| *Thielaviopsis basicola* | 0.80 |

The importance of the four disulfide bonds in NaD1 was investigated by reducing and alkylating the cysteine residues. Reduced and alkylated NaD1 (NaD1$_{R\&A}$) was completely inactive in the growth inhibitory assays with Fov, even at a concentration ten-fold higher than the IC$_{50}$ for NaD1.

The activities of many antimicrobial peptides are attenuated by the presence of cations, particularly divalent cations, in the media; therefore the effect of NaD1 (10 µM) on the growth of Fov was measured in the presence of the divalent cations Ca$^{2+}$ and Mg$^{2+}$ to determine their effect on NaD1 activity. Both cations decreased the antifungal activity of NaD1 in a concentration-dependent manner. Complete inactivation of NaD1 was observed at <2 mM CaCl$_2$, whereas 50 mM MgCl$_2$ was required to achieve the same effect, indicating that Ca$^{2+}$ was greater than 20 times more antagonistic. This indicates the effect is not simply related to charge and that blocking of specific interactions may be involved. By contrast, the activity of the tobacco protein osmotin is enhanced by the presence of Ca$^{2+}$, presumably by facilitating an interaction with phosphomannans on the fungal cell surface (Salzman et al, 2004).

Another embodiment of the present disclosure is a method for identifying a defensin which enhances antifungal activity of a proteinase inhibitor, without the need to carry out antifungal activity assays. The method entails measuring the ability of a defensin to permit entry into a fungal cell of a permeability indicator compound. A suitable permeabilization indicator compound is one whose location, whether intracellular or extracellular, can be detected. Under normal conditions, the indicator compound remains extracellular and does not freely pass through the cell wall and membrane. In the presence of certain defensins, such as NaD1, the indicator compound can be detected inside the cell of a given fungus (U.S. patent application Ser. No. 12/367,657). If a defensin being tested (a test defensin) is found to increase permeability of a given fungus by increasing the intracellular amount of the indicator compound, when present with the fungus, that defensin is thereby identified as one that enhances antifungal activity of a proteinase inhibitor, when the defensin and proteinase inhibitor are combined in the presence of the fungus.

A standard criterion for a permeability indicator compound suitable for use in the methods herein is provided by the use of SYTOX® green (Invitrogen Corp. Carlsbad, Calif., USA) as an indicator for increased fungal cell permeability observed in the presence of NaD1, as described below. The method of identifying a defensin that enhances efficacy of a proteinase inhibitor is not limited to the use of SYTOX® green, but can be carried out with any use of any permeability indicator compound that yields similar permeability data when tested with NaD1.

The described method is carried out using methods described below, or with adaptations that would be understood by one skilled in the art as being equivalent. The steps of the method include: combining a fungus with a permeability indicator compound in the presence of, and separately, as a control, in the absence of, a test defensin; then comparing any detectable intracellular amounts of permeability indicator compound in the fungus in the presence and in the absence of the test defensin. If the effect of presence of the test defensin is such that an increased amount of intracellular indicator compound is detected in the fungus, compared to the control, the test defensin is identified as one which can enhance the efficacy of a proteinase inhibitor when the defensin and the proteinase inhibitor are combined in the presence of the fungus. A plant defensin identified by the method just described will be understood to be useful as a defensin component of the system for protecting a plant from fungus disease as disclosed herein, whether or not the defensin is known to have anti-fungal activity.

Permeabilization of Fov hyphal membranes by NaD1 was measured using the fluorescent dye SYTOX® green. SYTOX® green fluorescence increases more than 1000 fold upon binding to nucleic acids, but the dye only enters cells when the plasma membrane is compromised. Hyphae were treated with 0.1, 2 or 10 µM NaD1 or 10 µM NaD1$_{R\&A}$ (reduced and alkylated) in the presence of SYTOX® green. NaD1 permeabilized hyphae, and this permeabilization correlated with growth inhibition, except at the lowest concentration of NaD1 (0.1 µM) where a small amount of SYTOX® green uptake occurred, but no growth inhibition was observed. Permeabilization was not observed in hyphae treated with NaD1$_{R\&A}$, nor with untreated hyphae, consistent with the lack of growth inhibition.

At a very low, non-inhibitory concentration of NaD1 (0.1 µM), SYTOX® green entered some, but not all hyphae, reflecting NaD1-mediated permeabilization. The nuclei of the hyphal cells that had taken up SYTOX® green appeared intact, and the cytoplasm appeared unaltered. At higher, inhibitory concentrations of NaD1, the SYTOX® green entered most hyphae and formed a diffuse pattern of fluorescence across the cell. The nuclei were no longer intact, and the cytoplasm of all permeabilized hyphae appeared granular after NaD1 treatment.

To determine whether NaD1 formed an opening of a distinct size or merely destabilized the plasma membrane, NaD1-treated hyphae were incubated with FITC-labeled dextrans (Sigma-Aldrich) of either 4 kDa (average globular diameter of 14 Å) or 10 kDa (average globular diameter of 23 Å). FITC-dextrans of 4 kDa entered hyphae at the same NaD1 concentration that led to SYTOX® green uptake (MW ~650 Da), while 10 kDa FITC-dextrans were excluded even at very high concentrations of NaD1. To examine whether the opening formed by NaD1 was transient or relatively stable, the assay was conducted in two ways. FITC-dextrans were either added at the same time as NaD1 or after removal of unbound NaD1 by extensive washing. The 4 kDa FITC-dextran was able to enter under both conditions.

NaD1 permeabilized the plasma membrane of susceptible hyphae in a dose-dependent manner that correlated with growth inhibition; however, at non-inhibitory concentrations of NaD1, some permeabilization was still detected. At these low concentrations, the cytoplasm of permeabilized hyphae appeared normal under the light microscope and SYTOX® green was localized to the nuclei. At higher, inhibitory concentrations of NaD1, permeabilized hyphae exhibited significant cytoplasmic granulation and the SYTOX® green fluorescence pattern was much more diffuse across the cell indicating that the nuclei were no longer intact. Without wishing to be bound by theory, it is believed that NaD1-induced permeabilization of fungal membranes is required for growth inhibition, although it may not be sufficient to induce cell death.

The fluidity of the fatty-acyl chains of membrane lipids decreases as the temperature decreases, leading to an overall increase in membrane stability. It is postulated that this makes insertion of peptides into bilayers more difficult, thus decreasing the amount of peptide-induced permeabilization that occurs through direct lipid interaction. This led to an assessment of the effect of temperature on NaD1-induced permeabilization. At 10° C. NaD1 induced substantial uptake of SYTOX® green, although this was less that that observed at 25° C. At 4° C., only a small degree of permeabilization could be seen and this was reduced even further at 0° C.

Without intending to be bound by any theory or mechanism of operation, it is postulated that NaD1 appears to act through either barrel-stave or toroidal pore formation. The consistency of uptake of the 4 kDa but not the 10 kDa dextrans over a number of NaD1 concentrations differs from other pore-forming antimicrobial peptides such as melittin, which cause a concentration-dependent increase in the size of dextrans that are released from artificial liposomes (Ladokhin and White, 2001), indicating an increase in pore size. The predicted size of the NaD1 pore is also large enough to allow NaD1 itself to pass through into the cell. It is also large enough to allow entry of certain proteinase inhibitors. In an embodiment, the present methods and compositions do not extend to the combination of the permeabilizing defensin NaD1 and the proteinase inhibitor NaPI from *Nicotiana alata*, when the defensin is NaD1, the proteinase inhibitor is not NaPI, and when the protease inhibitor is NaPI, the defensin is not NaD1.

The rate of permeabilization of Fov hyphae by various concentrations of NaD1 was monitored by measuring SYTOX® green uptake over time. At all concentrations, permeabilization was only observed after a lag time of around 20 min, and fluorescence began to plateau after 90 min. The rate of permeabilization was partially concentration-dependent, increasing progressively with NaD1 concentrations up to 3 µM. At concentrations above 3 µM (up to 50 µM), there was very little difference in the kinetics of permeabilization. This was reflected in the Vmax (maximum rate of fluorescence increase) data which show a steady state of uptake at low concentrations (below those required for significant growth inhibition), followed by a linear increase in fluorescence up to 6.25 µM NaD1. Above this concentration, the reaction rate did not change significantly, indicating the process is saturable.

The apparent loss of organelles after exposure to NaD1 indicated cells were undergoing cell death. To examine this further, the production of reactive oxygen species (ROS) was investigated in hyphae treated with NaD1. The non-fluorescent molecule dihydrorhodamine 123 (DHR123) was pre-loaded into hyphae which were then treated with NaD1 (0.1, 2 and 10 µM) or 10 µM NaD1$_{R\&A}$. In the presence of ROS, DHR123 is oxidized to the fluorescent molecule rhodamine 123. A concentration-dependent increase in fluorescence was observed in Fov hyphae following exposure to NaD1 at concentrations of NaD1 sufficient for growth inhibition. No fluorescence was observed after treatment with NaD1$_{R\&A}$, consistent with its lack of antifungal activity.

Ascorbic acid and 2,2,6,6-tetramethylpiperidine-N-oxyl (TEMPO) (Sigma-Aldrich) are both potent, cell-permeant scavengers of ROS. To explore the relevance of NaD1-induced ROS production, DHR123 oxidation by NaD1 was monitored in the presence of these two molecules. The presence of ascorbic acid or TEMPO did not alter the level of fluorescence, nor did the presence of 10 mM ascorbic acid affect growth inhibition of Fov by NaD1.

In summary, NaD1 disrupts membranes, apparently via formation of a putative-toroidal or barrel-stave pore that allows entry of molecules between 14 and 23 Å in diameter. NaD1 does not appear to interact with artificial bilayers, including those formed with lipids isolated from the hyphae of sensitive fungi, indicating that it may not interact directly with lipids, although the temperature dependence of toxicity supports the idea that it does insert into the membrane. The kinetics of SYTOX® green uptake suggest that a receptor is involved in membrane permeabilization.

Immunogold electron microscopy was used to determine whether NaD1 could cross the cell membrane and enter the cytoplasm of treated hyphae. Hyphae treated with or without NaD1 (10 µM) for 2 h were washed, fixed and sectioned for immunogold electron microscopy using the α-NaD1 antibody. Many, but not all, of the NaD1-treated hyphae had granulated cytoplasm with a number of aberrant vacuoles. The cytoplasm in these hyphae was heavily labeled with the α-NaD1 antibody although the NaD1 was not associated with particular intracellular organelles. The granulated cytoplasm in the NaD1-treated hyphae appeared to have collapsed inward, away from the cell wall. Gold labeling was also observed on the cell walls.

A number of hyphae that had not taken up large amounts of NaD1 were also present in the NaD1-treated sample. The cytoplasm of these hyphae was not granular, suggesting that NaD1 uptake is essential to the cell killing process. In support of this, hyphae could also be identified with partially granulated cytoplasm, and NaD1 was concentrated in these areas but not in the areas of the cell that appeared normal. This could represent an early stage of cell death.

The absence of NaD1 from several hyphae at a concentration that was sufficient to cause >90% growth inhibition may give some information as to the mode of uptake of NaD1. The growth inhibition assays were started with spores, so NaD1 was present through all stages of the cell cycle. In contrast, the microscopy was performed on hyphae that may have been at different stages of the cell cycle. Since immunoblotting analysis revealed that NaD1 remained in the supernatant after 3 h, the lack of internalization of NaD1 by some hyphae is not due to an insufficient concentration being used. It is possible that NaD1 is not able to affect cells in certain stages of the cell cycle. This is consistent with observations for the insect antifungal peptide, tenecin 3, which is taken up into yeast cells during logarithmic phase growth but not during stationary phase (Kim et al, 2001). Hyphae that do not take up NaD1 in the microscopy assays may represent those in a different stage of growth that are resistant to NaD1. This could be explained by predicted cell wall changes that occur upon entry into stationary phase that may prevent peptide uptake (Klis et al, 2002). In support of this, the antimicrobial peptide cecropin, which is able to inhibit the growth of germinating but not non-germinating *Aspergillus hyphae*, only binds to the cell surface of germinating hyphae (Ekengren and Hultmark, 1999).

To further confirm NaD1 uptake and to exclude the possibility that the presence of NaD1 in the cytoplasm was an artifact of the fixation process, NaD1 was labeled with the fluorophore bimane. This fluorophore was chosen because of its small, uncharged nature and the ability to covalently attach the molecule to carboxyl residues on NaD1. NaD1 labeled in this manner retained full antifungal activity. In contrast, NaD1 labeled with FITC via reactive amine groups was not biologically active, probably due to the fact that the molecule carries two negative charges at physiological pH. The attachment of a single FITC molecule to a reactive amine in NaD1 would thus reduce the overall charge of the protein by three. Since a positive charge is proposed to be vital for antimicrobial activity, NaD1 may not be able to tolerate this treatment. Furthermore, two of the lysines on NaD1 which would react with FITC are located on the loop regions that have been described as essential for the antifungal activity of another plant defensin, RsAFP2 (De Samblanx et al, 1997).

NaD1-bimane was added to live hyphae, and uptake was monitored by fluorescence microscopy. Internalization was observed after 20-30 min, which is consistent with the SYTOX® green permeabilization kinetics. At this time point the hyphae that had taken up NaD1 still looked healthy, however, over time, the cytoplasm of these hyphae became granular and they appeared to die. NaD1 did not appear to interact with specific organelles upon uptake but rather demonstrated a cytoplasmic localization. This differs from the plant defensin Psd1 which is transported to the nucleus of treated *N. crassa* cells (Lobo et al, 2007). Interaction of Psd1 with a nuclear-located cell-cycle protein has also been validated and its antifungal activity is believed to be a result of cell-cycle arrest (Lobo et al, 2007 supra). The antifungal protein from *P. chrysogenum*, PAF, on the other hand, displays cytoplasmic localization upon entry into *A. nidulans* hyphae (Oberparleiter et al, 2003). After entry, PAF induces an apoptotic phenotype, probably through G-protein signaling (Leiter et al, 2005).

The amount of NaD1 taken up into the cytoplasm of Fov hyphae was also monitored by SDS-PAGE and immunoblotting of cytoplasmic contents. These data indicated that NaD1 uptake occurred after 20 min which is consistent with the microscopy. The amount of NaD1 in the Fov cytoplasm increased up until 60 min, after which time it decreased slightly. This may be a result of cell breakdown and subsequent release of some internalized NaD1 back into the surrounding supernatant.

Evidence is now mounting that a number of antimicrobial peptides are able to enter cells and their mechanism of action involves intracellular targets. The cytoplasm of the NaD1-treated hyphae appeared 'shrunken' and contracted away from the cell wall. A similar morphology was observed in *Aspergillus nidulans* hyphae treated with the antifungal protein, AFP, from *Aspergillus giganteus*. AFP is fungistatic at low concentrations, causes membrane permeabilization and binds to the cell wall, while at high concentrations the protein is internalized and causes granulation of the hyphal cytoplasm (Theis et al, 2003; Theis et al, 2005).

A method for identifying a defensin which enhances anti-pathogen activity of a proteinase inhibitor, comprising the steps of: combining a pathogen with a permeability indicator compound in the presence of, and separately, in the absence of, a test defensin; comparing any detectable intracellular amounts of permeability indicator compound in the fungus in the presence and in the absence of the test defensin, whereby a test defensin, the presence of which increases the amount of intracellular permeability indicator compound compared to the intracellular amount of indicator compound detected in the absence of the test defensin, is identified as a defensin which enhances anti-fungal activity of a proteinase inhibitor.

Another aspect herein is directed to a topical composition comprising a fungus-permeabilizing plant defensin and a proteinase inhibitor or precursor form thereof wherein if the defensin is NaD1 then the proteinase inhibitor is not NaPI, when the defensin is NaD1, the proteinase inhibitor is not NaPI, and when the protease inhibitor is NaPI, the defensin is not NaD1.

Another aspect herein provides a topical anti-fungal composition comprising a fungus-permeabilizing plant defensin and a proteinase inhibitor or precursor form thereof wherein if the defensin is NaD1, then the proteinase inhibitor is not NaPI, when the defensin is NaD1, the proteinase inhibitor is not NaPI, and when the protease inhibitor is NaPI, the defensin is not NaD1. In an embodiment, the anti-fungal composition is a seed coating composition.

All references throughout this application, for example, patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification reflect the level of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that may be in the prior art.

When a group of substituents is disclosed herein, it is understood that all individual members of those groups and all subgroups, including any isomers and enantiomers of the group members with the same biological activity, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every combination of components described or exemplified or referenced can be used to practice the invention, unless otherwise stated. Specific names of compounds are intended to be exemplary, as it is known that one of ordinary skill in the art can name the same compounds differently. One of ordinary skill in the art will appreciate that methods, starting materials, synthetic methods and recombinant methodology other than those specifically exemplified can be employed in the practice of the invention without resort to undue experimentation. All art-known functional equivalents, of any such methods, starting materials, synthetic methods, and recombinant methodology are intended to be included in this invention. Whenever a range is given in the specification, for example, a temperature range, a time range, or a composition range, all intermediate ranges and subranges, as well as all individual values included in the ranges given are intended to be included in the disclosure.

In the claims of the present application, all dependent claims alternatively encompass the limitations of any and/or all prior claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition, method or system, is understood to encompass those compositions, methods and systems consisting essentially of and consisting of the recited components or elements or steps. The invention illustratively described herein suitably may be practiced in the absence of any element or elements, limitation or limitations which is not specifically disclosed herein.

One skilled in the art readily appreciates that the present invention is well adapted to carry out the objects and obtain the ends and advantages mentioned, as well as those inherent in the present invention. The methods, components, materials and dimensions described herein as currently representative of preferred embodiments are provided as examples and are not intended as limitations on the scope of the invention. Changes therein and other uses which are encompassed within the spirit of the invention will occur to those skilled in the art, are included within the scope of the claims. Although the description herein contains certain specific information and examples, these should not be construed as limiting the scope of the invention, but as merely providing illustrations of some of the embodiments of the invention. Thus, additional embodiments are within the scope of the invention and within the following claims.

It should be noted that the crop scientist, agriculturist or botanist would know how to and when to terminate, interrupt, or adjust administration due to toxicity or a deleterious effect on performance of the plant to be protected. Conversely, the artisan would also know to adjust treatment to higher levels if the response were not adequate (precluding toxicity). The magnitude of an administered dose of proteinase inhibitor and/or defensin or the level of expression of a recombinantly expressed proteinase inhibitor or defensin can be adjusted by means known to one of skill in the relevant arts, or the administration means or formulation for the proteinase inhibitor and/or defensin, if applied to the plant or seed, can be changed to improve protection of the plant from fungal pathogens. The severity of the condition may, for example, be evaluated, in part, by standard prognostic evaluation methods. Further, the dose and perhaps dose frequency, will also vary according to the age, size, soil and/or climatic conditions and response of the individual plant.

Use of agronomically acceptable carriers to formulate the compound(s) herein disclosed for the practice of the invention into dosages suitable for systemic and surface administration is within the scope of the invention and within the ordinary level of skill in the art. With proper choice of carrier and suitable manufacturing practice, the compositions of the present invention, in particular those formulated as solutions, may be administered to plant surfaces including above-ground parts and/or roots, or as a coating applied to the surfaces of seeds.

Agronomically useful compositions suitable for use in the system disclosed herein include compositions wherein the active ingredient(s) are contained in an effective amount to achieve the intended purpose. Determination of the effective amounts is well within the capability of those skilled in the art, especially in light of the disclosure provided herein.

In addition to the active ingredients, these compositions for use in the antifungal method may contain suitable agronomically acceptable carriers comprising excipients and auxiliaries which facilitate processing of the active compounds into preparations which can be used in the field, in greenhouses or in the laboratory setting.

Antifungal formulations include aqueous solutions of the active compounds in water-soluble form. Additionally, suspensions of the active compounds may be prepared as appropriate oily suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Further components can include viscosifiers, gels, wetting agents, ultraviolet protectants, among others.

Preparations for surface application can be obtained by combining the active compounds with solid excipient, optionally grinding a resulting mixture, and processing the mixture of granules, after adding suitable auxiliaries, if desired, to obtain powders for direct application or for dissolution prior to spraying on the plants to be protected. Suitable excipients are, in particular, fillers such as sugars, including lactose, sucrose, mannitol, or sorbitol; cellulose or starch preparations, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The present compositions and methods are further described in the following non-limiting Examples. Materials and methods employed in these Examples are provided below.

EXAMPLES

Purification of NaD1 from *Pichia pastoris* and from *Nicotiana alata*

The *Pichia pastoris* expression system is well-known and commercially available from Invitrogen (Carlsbad, Calif.; see the supplier's *Pichia* Expression Manual disclosing the sequence of the pPIC9 expression vector).

A single pPIC9-NaD1 *P. pastoris* GS115 colony was used to inoculate 10 mL of BMG medium (described in the Invitrogen *Pichia* Expression Manual) in a 100 mL flask and that was incubated overnight in a 30° C. shaking incubator (140 rpm). The culture was used to inoculate 500 mL of BMG in a 2 L baffled flask which was placed in a 30° C. shaking incubator (140 rpm). Once the $OD_{600}$ reached 2.0 (~18 h) cells were harvested by centrifugation (2,500×g, 10 min) and resuspended into 1 L of BMM medium ($OD_{600}$=1.0) in a 5 L baffled flask and incubated in a 28° C. shaking incubator for 3 days. The expression medium was separated from cells by centrifugation (4750 rpm, 20 min) and diluted with an equal volume of 20 mM potassium phosphate buffer (pH 6.0). The medium was adjusted to pH 6.0 with NaOH before it was applied to an SP Sepharose column (1 cm×1 cm, Amersham Biosciences) pre-equilibrated with 10 mM potassium phosphate buffer, pH 6.0. The column was then washed with 100 mL of 10 mM potassium phosphate buffer, pH 6.0 and bound protein was eluted in 10 mL of 10 mM potassium phosphate buffer containing 500 mM NaCl. Eluted proteins were subjected to RP-HPLC using a 40 minute linear gradient as described herein below. Protein peaks were collected and analyzed by SDS-PAGE and immunoblotting with the α-NaD1 antibody. Fractions containing NaD1 were lyophilized and resuspended in sterile milli Q ultrapure water. The protein concentration of *Pichia*-expressed NaD1 was determined using the bicinchoninic acid (BCA) protein assay (Pierce Chemical Co.) with bovine serum albumin (BSA) as the protein standard.

To isolate NaD1 from its natural source, whole *N. alata* flowers up to the petal coloration stage of flower development were ground to a fine powder and extracted in dilute sulphuric acid as described previously (Lay et al, 2003). Briefly, flowers (760 g wet weight) were frozen in liquid nitrogen, ground to a fine powder in a mortar and pestle, and homogenized in 50 mM sulfuric acid (3 mL per g fresh weight) for 5 min using an Ultra-Turrax homogenizer (Janke and Kunkel). After stirring for 1 h at 4° C., cellular debris was removed by filtration through Miracloth (Calbiochem, San Diego, Calif.) and centrifugation (25,000×g, 15 min, 4° C.). The pH was then adjusted to 7.0 by addition of 10 M NaOH and the extract was stirred for 1 h at 4° C. before centrifugation (25,000×g, 15 min, 4° C.) to remove precipitated proteins. The supernatant (1.8 L) was applied to an SP Sepharose™ Fast Flow (GE Healthcare Bio-Sciences) column (2.5×2.5 cm) pre-equilibrated with 10 mM sodium phosphate buffer, pH7.0. Unbound proteins were removed by washing with 20 column volumes of 10 mM sodium phosphate buffer (pH 6.0) and bound proteins were eluted in 3×10 mL fractions with 10 mM sodium phosphate buffer (pH 6.0) containing 500 mM NaCl. Samples from each purification step were analyzed by SDS-polyacrylamide gel electrophoresis (SDS-PAGE) and immunoblotting with the α-NaD1 antibodies. Fractions from the SP Sepharose column containing NaD1 were subjected to reverse-phase high performance liquid chromatography (RP-HPLC).

Reverse-Phase High Performance Liquid Chromatography

Reverse-phase high performance liquid chromatography (RP-HPLC) was performed on a System Gold HPLC (Beckman) coupled to a detector (model 166, Beckman) using a preparative C8 column (22×250 mm, Vydac) with a guard column attached. Protein samples were loaded in buffer A (0.1% [v/v] trifluoroacetic acid) and eluted with a linear gradient of 1-100% (v/v) buffer B (60% [v/v] acetonitrile in 0.089% [v/v] trifluoroacetic acid) at a flow rate of 10 mL/min over 40 min. Proteins were detected by monitoring absorbance at 215 nm. Protein peaks were collected and analyzed by SDS-PAGE.

Samples from each stage of NaD1 purification (30 μL) were added to NuPAGE (Registered) LDS sample loading buffer (10 μL, Invitrogen) and heated to 70° C. for 10 min. The samples were then loaded onto NuPAGE (Registered) precast 4-12% Bis-Tris polyacrylamide gels (Invitrogen) and the proteins were separated using an XCell-Surelock electrophoresis apparatus (Invitrogen) run at 200 V. Proteins were visualized by Coomassie Blue staining or transferred onto nitrocellulose for immunoblotting with the α-NaD1 antibodies.

Preparation of Reduced and Alkylated NaD1

Lyophilized NaD1 (500 μg) was dissolved in 400 μL of stock buffer (200 mM Tris-HCl pH 8.0, 2 mM EDTA, 6 M guanidine-HCl, 0.02% [v/v] Tween-20). Reduction buffer (stock buffer with 15 mM dithiothreitol [DTT]) was added (44 μL) followed by a 4.5 h incubation at 40° C. The reaction mixture was cooled to RT before iodoacetic acid (0.5 M in 1 M NaOH, 55 μL) was added and the incubation continued in the dark for 30 min at RT. A Nanosep omega (Registered) spin column (3K molecular weight cut off, PALL Life Sciences) was used to remove salts, DTT and iodoacetic acid and the protein concentration was determined using the BCA protein assay (Pierce). The effect of reduced and alkylated NaD1 ($NaD1_{R\&A}$) on the growth of *Fusarium oxysporum* (Fov) was measured as described herein.

Immunoblot Analysis

For immunoblot analysis, proteins were transferred to nitrocellulose and probed with protein A-purified α-NaD1 antibodies (1:3000 dilution of 7.5 µM) followed by goat α-rabbit IgG conjugated to horseradish peroxidase (1:3500 dilution; Amersham Pharmacia Biotech). Enhanced chemiluminescence (ECL) detection reagents (Amersham Pharmacia Biotech) were used to visualize bound antibodies with a ChemiGenius (Trade Mark) bioimaging system (Syngene).

To produce anti-NaD1 antiserum, purified NaD1 (1.5 mg) was conjugated to Keyhole Limpet Hemocyanin (0.5 mg, Sigma) with glutaraldehyde as described by Harlow and Lane, 1998. A rabbit was injected with 1.5 mL of protein (150 µg NaD1) in an equal volume of Freund's complete adjuvant (Sigma). Booster immunizations of conjugated protein (100 µg NaD1) and Freund's incomplete adjuvant (Sigma-Aldrich) were administered four and eight weeks later. Pre-immune serum was collected before injection and immune serum was collected 14 d after the third and fourth immunizations. The IgG fraction from both pre-immune and immune serum was purified using Protein-A Sepharose CL-4B (Amersham Pharmacia Biotech) and was stored at −80° C. at concentrations of 3.4 µM and 7.5 µM, respectively.

Analysis of Activity Against Filamentous Fungi

Antifungal activity against *Fusarium oxysporum* f. sp. *vasinfectum* (Fov, Australian isolate VCG01111 isolated from cotton; from Wayne O'Neill, Farming Systems Institute, DPI, Queensland, Australia), Thielaviopsis basicola (gift from David Nehl, NSW DPI, Narrabri, Australia), *Verticillium dahliae* (from Helen McFadden, CSIRO Plant Industry, Black Mountain, Australia), *Leptosphaeria maculans* (from Barbara Howlett, University of Melbourne, Victoria, Australia) and *Aspergillus nidulans* (from Michael Hynes, University of Melbourne) was assessed essentially as described in Broekaert et al, 1990. Spores were isolated from sporulating cultures growing in either half-strength potato dextrose broth (PDB) (Fov and *T. basicola*), Czapeck-Dox Broth (V. dahliae) (Difco Laboratories) or 10% (v/v) clarified V8 medium (*L. maculans* and *A. nidulans*) by filtration through sterile muslin. Spore concentrations were determined using a hemocytometer and adjusted to $5 \times 10^4$ spores/mL in the appropriate growth medium. Spore suspensions (80 µL) were added to the wells of sterile 96-well flat-bottomed microtitre plates along with 20 µL of filter-sterilized (0.22 µm syringe filter; Millipore) NaD1, or water to give final protein concentrations of 0-10 µM. The plates were shaken briefly and placed in the dark at 25° C. without shaking until the optical density at 595 nm of the water control reached approximately 0.2 (24-72 h depending on growth rate). Hyphal growth was estimated by measuring the optical density at 595 nm using a microtitre plate reader (SpectraMax Pro M2; Molecular Devices). Each test was performed in quadruplicate.

Effect of Metal Ions on NaD1 Activity

The activity of NaD1 against Fov was examined as described with varying concentrations of $CaCl_2$ (0.1, 0.2, 0.5, 1.0 and 2.0 µM) or $MgCl_2$ (1.0, 2.0, 10, 20 and 50 µM) present in the medium to determine the effects of divalent cations on NaD1 activity.

NaD1 and Membrane Permeabilization

Fov hyphae were grown in half-strength PDB (10 mL in a 50 mL tube) from a starting concentration of $5 \times 10^4$ spores/mL for 18 h at 25° C. with constant shaking. Samples (1 mL) were then removed and NaD1 (final concentration 2 µM), $NaD1_{R\&A}$ (final concentration 2 µM) or an equivalent volume of water was added before incubation for 2 h at RT with gentle agitation. SYTOX® green (Invitrogen-Molecular Probes, Eugene, Oreg.) was added to a final concentration of 0.5 µM and the hyphae were allowed to stand for 10 min. Hyphae (20 µL) were then transferred to microscope slides (SuperFrost (Registered) Plus, Menzel-Glaser) and covered with glass coverslips for visualization of SYTOX® green uptake using an Olympus BX51 fluorescence microscope. SYTOX® green fluorescence was detected using an MWIB filter (excitation wavelength 460-490 nm). Images were captured using a SPOT RT 3CCD digital camera (Diagnostic Instruments) and processed using Adobe Photoshop. SYTOX® green uptake was quantitated by measuring fluorescence of hyphae in microtitre trays using a fluorimeter (SpectraMax M2; Molecular Devices) with excitation and emission wavelengths of 488 nm and 538 nm, respectively.

The uptake of FITC-labeled dextran following NaD1 treatment of fungal hyphae was also studied. Fov hyphae were grown as described above and incubated with NaD1 (final concentration 0.1, 2, 10 or 50 µM) or an equivalent volume of water for 2 h at RT with gentle agitation. Hyphae were washed twice for 10 min with half-strength PDB to remove excess NaD1 before FITC dextrans of either 4 kDa (FD-4, Sigma-Aldrich) or 10 kDa (FD-10, Sigma-Aldrich) were added to a final concentration of 1 µM. Hyphae were incubated for a further 30 min at RT and then washed twice with half strength PDB to remove excess dextrans. Fluorescence microscopy was used to visualize hyphae as described for SYTOX® green. A second assay was performed under the same conditions except the dextrans were added at the same time as NaD1.

The effect of temperature on membrane permeabilization of Fov hyphae by NaD1 was monitored as described, except hyphae were pre-equilibrated for 60 min at either 10°, 4° or 0° C. before addition of NaD1 and all subsequent steps were carried out at these temperatures.

The kinetics of membrane permeabilization by NaD1 were studied. Fov hyphae were grown in half-strength PDB from a starting concentration of $5 \times 10^4$ spores/mL for 18 h at 25° C. Hyphae (80 µL) were then transferred to 96-well microtitre plates and incubated with SYTOX® green (0.5 µM) for 10 min prior to the addition of 20 µL of peptide solution to give final protein concentrations of 0.2, 0.4, 0.8, 1.6, 3.12, 6.25, 12.5, 25, 50 or 100 µM. Fluorescence readings (Ex; 488 nm, Em; 538 nm) were then taken every 2 min for 3 h using a fluorimeter (SpectraMax M2).

Isolation of NaD1 from Treated Hyphae

Fov hyphae were grown as described above prior to the addition of NaD1 (10 µM final concentration) to 1 mL of the culture. Samples (100 µL) were collected after 0, 5, 10, 30, 60, 90 and 120 min. Hyphae were collected by centrifugation (10 min, 10,000×g) and the supernatant was stored at −20° C. for analysis. Hyphae were washed (2×10 min) with KCl (0.6 M) to remove any ionically bound protein before they were resuspended in 50 mM CAPS buffer (pH 10.0) containing 10 mM DTT for 20 min. Hyphae were collected by centrifugation and the supernatant, containing cell wall proteins, was collected for analysis. The pellet (containing cells) was resuspended in water and the cells were lysed using glass beads (Sigma, 60 mg) and vortexing (3×10 min). Cellular debris was removed by centrifugation (16,000×g, 10 min) and the supernatant collected for analysis. All samples were then analyzed by SDS-PAGE and immunoblotting.

Electron Microscopy

Fov hyphae were grown for 18 h in half-strength PDB (5 mL) with vigorous shaking at 25° C. from a starting spore suspension of $5 \times 10^4$/mL. Hyphae were then treated with 2 µM NaD1 or an equivalent volume of water for 2 h at RT with gentle agitation, and were washed twice in 0.6 M KCl and three times in PBS before fixation in 4% (w/v) paraformaldehyde in PBS for 1 h at 4° C. Hyphae were again washed three times in PBS before dehydration in a standard ethanol series (15 min each, 50%, 70% and 90% ethanol, 3×15 min 100% ethanol). Hyphae were then infiltrated with LR White resin (ProSciTech) for 1 h at RT, followed by 18 h at 4° C., 1 h at RT and 24 h at 60° C. Fresh LR White resin was used at each step. Ultrathin sections were cut and placed on Formvar coated gold grids.

Grids were blocked with PBS containing 8% (w/v) BSA and 1% (v/v) Triton X-100 for 1 h and labeled with α-NaD1 antibodies (2 μg/mL in blocking buffer) for 1 h. Grids were washed in blocking buffer (3×10 min) and labeled with 15 nm gold particle labeled goat α-rabbit IgG antibodies (ProSciTech diluted 1 in 20 for 1 h. Grids were washed again in blocking solution (3×10 min) followed by water (15 min) before being air-dried. A JEOL JEM2010HC x e80 KV transmission electron microscope was used to examine labeled grids. Pictures were taken on Kodak EM film (ProSciTech) and developed in a dark room before scanning on a Hewlett Packard Scanjet 5P scanner.

Monitoring uptake of fluorescently labeled NaD1

Fluorescein isothiocyanate (FITC) was conjugated to NaD1 using the EZ-label (Trade Mark) FITC protein labeling kit (Pierce) as described by the manufacturer.

To produce bimane amine labeled NaD1, lyophilized NaD1 was dissolved in 0.1 M MES buffer (pH 5.0) to a final concentration of 2 mM. The fluorescent tag bimane amine (Invitrogen-Molecular Probes) was added to a final concentration of 10 mM along with 1-ethyl-3-(3-dimethylaminopropyl)-carbodiimide (EDC, final concentration of 2 mM). The reaction was incubated at RT for 2 h with gentle stirring before centrifugation (13,000 rpm, 10 min) to remove any precipitated protein. A Nanosep omega 3K spin column (PALL life sciences) was used to remove salts, unbound bimane amine and EDC. The bimane-labeled NaD1 was resuspended in water and the protein concentration was determined using the BCA protein assay (Pierce).

Hyphae grown for 18 h as described were treated with NaD1-bimane (2 μM) for between 10 min and 6 h. Hyphae were then visualized by fluorescence microscopy using an MWU filter (excitation wavelength of 330-385 nm).

Detection of Reactive Oxygen Species in Response to NaD1 Treatment

Fov hyphae were grown as described herein and incubated with 5 μg/mL dihydrorhodamine 123 (Sigma-Aldrich) for 2 h followed by extensive washing with growth medium. Hyphae were then treated with NaD1 (2 μM) or water for 1 h before being washed with 0.6 M KCl. Fluorescence was then measured on a fluorimeter with excitation and emission wavelengths of 488 nm and 538 nm respectively or visualized by fluorescence microscopy. The experiment was repeated either in the presence of ascorbic acid (10 mM) or 2,2,6,6-tetramethylpiperidine-N-oxyl (TEMPO, 3 mM).

Production of Transgenic Plant Cells and/or Tissue

Techniques and agents for introducing and selecting for the presence of heterologous DNA in plant cells and/or tissue are well-known. Genetic markers allowing for the selection of heterologous DNA in plant cells are well-known, e.g. genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e. the chimeric gene containing nopaline synthetase promoter, Tn5 neomycin phosphotransferase II and nopaline synthetase 3' non-translated region described by Rogers et al, 1988.

Techniques for genetically engineering plant cells and/or tissue with an expression cassette comprising an inducible promoter or chimeric promoter fused to a heterologous coding sequence and a transcription termination sequence are to be introduced into the plant cell or tissue by Agrobacterium-mediated transformation, electroporation, microinjection, particle bombardment or other techniques known to the art. The expression cassette advantageously further contains a marker allowing selection of the heterologous DNA in the plant cell, e.g. a gene carrying resistance to an antibiotic such as kanamycin, hygromycin, gentamicin, or bleomycin.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g. calcium phosphate coprecipitation, viral vectors, and other techniques practiced in the art. Suitable plant transformation vectors include those derived from a Ti plasmid of Agrobacterium tumefaciens, such as those disclosed by Herrera-Estrella et al, 1983, Bevan et al, 1983; Klee et al, 1985 and EPO publication 120,516 (Schilperoort et al, European Patent Publication 120, 516). In addition to plant transformation vectors derived from the Ti or root-inducing (Ri) plasmids of Agrobacterium, alternative methods can be used to insert the DNA constructs described herein into plant cells.

The choice of vector in which the DNA of interest is operatively linked depends directly, as is well known in the art, on the functional properties desired, e.g. replication, protein expression, and the host cell to be transformed, these being limitations inherent in the art of constructing recombinant DNA molecules. The vector desirably includes a prokaryotic replicon, i.e. a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule provided herein. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT™ and pBS available from Stratagene (La Jolla, Calif.). A vector herein may also be a Lambda phage vector as known in the art or a Lambda ZAP vector (available from Stratagene La Jolla, Calif.). Another vector includes, for example, pCMU (Nilsson et al, 1989). Other appropriate vectors may also be synthesized, according to known methods; for example, vectors pCMU/Kb and pCMUII used in various applications herein are modifications of pCMUIV (Nilsson et al, 1989).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens*.

A transgenic plant can be produced by any standard means known to the art, including but not limited to *Agrobacterium tumefaciens*-mediated DNA transfer, preferably with a disarmed T-DNA vector, electroporation, direct DNA transfer, and particle bombardment. Techniques are well-known to the art for the introduction of DNA into monocots as well as dicots, as are the techniques for culturing such plant tissues and regenerating those tissues.

Monoclonal or polyclonal antibodies, preferably monoclonal, specifically reacting with a polypeptide or protein of interest may be made by standard methods known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Abbreviations and nomenclature, where employed, are deemed standard in the field and commonly used in professional journals such as those cited herein.

Example 1

Cloning and Recombinant Expression of Cysteine Proteinase Inhibitors from *Nicotiana alata*

Cysteine proteinase inhibitor cDNAs were isolated from the ornamental tobacco *Nicotina alata* using standard molecular biology methods.
RNA Extraction Immature leaves, mature leaves and styles (~100 mg each) from *Nicotiana alata* were ground in liquid nitrogen. Trizol reagent (Invitrogen) was added to a final volume of 1 mL and the samples were incubated at room temperature for 5 min. The samples were then centrifuged (18,000 g at 4° C. for 10 min) and the supernatant was removed to a fresh tube. Chloroform (200 uL) was added and the tubes were vortexed for 15 s, incubated at room temperature for 3 min and then centrifuged (18,000 g at 4° C. for 15 min). The aqueous layer was removed to a fresh tube and isopropanol (500 uL) was added. The samples were vortexed, incubated at room temperature for 10 min, then centrifuged (18,000 g at 4° C. for 10 min). The supernatant was discarded and the pellet was washed with ethanol (75% v/v, 1 mL), centrifuged (18,000 g at 4° C. for 5 min) and the supernatant discarded. The RNA pellet was air-dried for 10 min and then resuspended in sterile distilled water (20 uL).
cDNA Synthesis RNA (1 ug) was added to DNase I (1 uL, 1 U/uL, Invitrogen), 10× DNase I reaction buffer (1 uL) and DEPC-treated water (to 10 uL) and incubated at room temperature for 15 min. EDTA (25 mM, 1 uL) was then added and the samples were heated for 10 min at 65° C. Oligo(dT)$_{20}$ primer (50 uM, 1 uL) and dNTP mix (10 mM each dATP, dGTP, dCTP and dTTP, 1 uL) were added and the samples were incubated for 5 min at 65° C. and then placed on ice. 5× First-Strand buffer (4 uL, Invitrogen), DTT (0.1 M, 1 uL), RNaseOUT Recombinant RNase Inhibitor (1 uL, Invitrogen) and Superscript III RT (200 U/uL, 1 uL, Invitrogen) were added and the samples were incubated for 30 min at 50° C. The reaction was then inactivated by heating for 15 min at 70° C.
PCR Amplification and Cloning of Cystatin cDNAs The oligonucleotide primers used to amplify cystatin cDNAs from *N. alata* were based on an EST sequence (GenBank accession number EB699598) from mature leaves of a *Nicotiana lansgdorfii×Nicotiana sanderae* cross. The 5' end of the two forward primers contained a Bam HI restriction site while the 3' end of the reverse primer contained a Sal I restriction site. The primer sequences were: JRF1: 5' AAG GAT CCA TGG CAA CAC TAG GAG G 3' (SEQ ID NO:26); JRF2: 5' AAG GAT CCA TGG CAA ATC TAG GAG G 3' (SEQ ID NO:27); JRR1: 5' AAG TGC ACT TAA GCA CTA GYG GCA TC 3' (SEQ ID NO:28). PCR reactions contained 10×PCR buffer (5 uL, Invitrogen), MgSO$_4$ (50 mM, 2 uL), dNTP mix (2.5 mM each, 4 uL), JRF1 or JRF2 primer (10 uM, 1 uL), JRR1 primer (10 uM, 1 uL), Platinum HiFi Taq DNA polymerase (5 U/uL, 0.2 uL, Invitrogen), sterile distilled water (34.8 uL) and cDNA (2 uL). Initial denaturing occurred at 94° C. for 2 min, followed by 35 cycles of 94° C. for 30s, 50° C. for 30 s and 68° C. for 30 s followed by a final elongation step of 68° C. for 5 min. The resultant ~300 by PCR product from mature leaf cDNA (also obtained from immature leaf and stylar cDNA) was cloned into the pCR2.1-TOPO vector (Invitrogen) which was then used to transform chemically competent *E. coli* cells (TOP10, Invitrogen) according to the manufacturer's instructions. Plasmid DNA was isolated using the Wizard Plus SV Miniprep kit (Promega) and vector inserts were sequenced (Macrogen) using the TOPO-specific M13 forward and reverse primers.
Recombinant Protein Expression and Purification NaCys1 (SEQ ID NO:1), NaCys2 (SEQ ID NO:3), NaCys3 (SEQ ID NO:5) and NaCys4 (SEQ ID NO:7) were PCR-amplified for subcloning into pHUE for recombinant protein expression in *E. coli* (Baker et al, 2005, Cantanzariti et al, 2004). The following primers were used: JRF3: 5' CTC CGC GGT GGT ATG GCA ACA CTA GGA GG 3' (SEQ ID NO:29); JRF4: 5' CTC CGC GGT ATG GCA AAT CTA GGA GG 3' (SEQ ID NO:30). PCR reactions contained 10×PCR buffer (5 uL, Invitrogen), MgSO$_4$ (50 mM, 2 uL), dNTP mix (2.5 mM each, 4 uL), JRF3 or JRF4 primer (10 uM, 1 uL), JRR1 (SEQ ID NO:26) primer (10 uM, 1 uL), Platinum HiFi Taq DNA polymerase (5 U/uL, 0.2 uL, Invitrogen), sterile distilled water (34.8 uL) and plasmid DNA from the respective TOPO clone (~1 mg/uL, 2 uL). Initial denaturing occurred at 94° C. for 2 min, followed by 30 cycles of 94° C. for 30s, 50° C. for 30 s and 68° C. for 30 s followed by a final elongation step of 68° C. for 5 min. PCR products were cloned into TOPO as described above. Inserts were excised using Sac II and Sac I, extracted from agarose gels using the Perfectprep kit (Eppendorf) and ligated into pHUE which was then used to transform TOP10 *E. coli* cells. For NaCys4, which has an internal, native Sac II site, an insert was excised from the cloned NaCys4 cDNA in the TOPO vector using an internal, native Eco RI site and the Sal I site in TOPO. This was ligated into pHUE containing NaCys2 which had also been digested with Eco RI and Sal I; the resultant DNA was used to transform TOP10 *E. coli* cells. Plasmid DNA for pHUE containing NaCys1, NaCys2, NaCys3 and NaCys4 was isolated and then used to transform *E. coli* BL21 (DE3) Codon Plus cells (Invitrogen).

Single colonies of *E. coli* (BL21 (DE3)) were used to inoculate 2YT media (10 mL, 16 g/L tryptone, 10 g/L yeast extract, 5 g/L NaCl) containing ampicillin (0.1 mg/mL), chloramphenicol (0.34 mg/mL) and tetracycline (0.1 mg/mL) and grown overnight with shaking at 37° C. This culture was used to inoculate 2YT media (500 mL) containing ampicillin (0.1 mg/mL) which was then grown for 4 h to an optical density (600 nm) of ~1.0. IPTG was then added (0.5 mM final concentration) and the culture grown for a further 3 h. Cells were harvested by centrifugation (4,000 g at 4° C. for 20 min), resuspended in native lysis buffer (20 mL per litre cell culture, 50 mM $NaH_2PO_4$, 300 mM NaCl, 10 mM imidazole, pH 8.0) and frozen at −80° C. Cells were then thawed and treated with lysozyme (5 mg per 25 mL resuspended cells) for 20 min at 4° C. DNase I (125 uL, 2 mg/mL in 20% glycerol, 75 mM NaCl) and $MgCl_2$ (125 uL, 1 M) were then added and the samples incubated at room temperature for 40 min on a rocking platform. The samples were then sonicated for 2×30 s on ice (80% power, Branson sonifier 450) and centrifuged (20,000 g at 4° C. for 30 min). The hexahistidine-tagged ubiquitin-fusion proteins (His6-Ub-NaCys-1,2,3) were then purified from the protein extracts by immobilized metal affinity chromatography (IMAC) under native conditions using Ni-NTA resin (1.5 mL to ~25 mL native protein extract, Qiagen) according to the manufacturer's instructions. Recombinant proteins were eluted using elution buffer (250 mM imidazole, 200 mM NaCl, 50 mM $NaH_2PO_4$, pH 8.0). The imidazole was removed by applying the eluted protein to a prepacked Sephadex G50 gel filtration column (PD-10, Amersham) equilibrated with 50 mM Tris.Cl, 100 mM NaCl, pH 8.0.

The hexahistidine-tagged ubiquitin was cleaved from the recombinant proteins using the deubiquitylating enzyme 6H.Usp2-cc (Cantanzariti et al. 2004). His6-Ub-NaCys1, 2 or 3 (~75 mg in 50 mM Tris.Cl, 100 mM NaCl, pH 8.0) was mixed with 6H.Usp2-cc (~0.6 mg) and DTT (1 mM final concentration) and incubated at 37° C. for 2 h. The cleaved tag was removed by another round of IMAC with the deubiquitylated cystatin as the unbound protein. This was then applied to another PD-10 column, eluted with water and lyophilized. The cystatins were characterized by SDS-PAGE, reversed-phase HPLC and MALDI-TOF mass spectrometry following digestion with trypsin.

The cysteine proteinase inhibitory activity of bacterially expressed NaCys1, NaCys3 and NaCys4 was determined using the enzymes papain and cathepsin L (Sigma). The assay mixtures (final volume 250 uL) contained papain or cathepsin L (50 nM final concentration), 100 uL of ZFR-MCA substrate (0.2 mM, Bachem, Melo et al., 2001), 100 uL of reaction buffer (0.2 M sodium acetate, 4 mM EDTA, 8 mM DTT, pH 5.5) and 50 uL of cystatin (for 0-20 uM final concentration). Released fluorescence was measured at 460 nm (excitation at 340 nm) after a 10 or 50 min incubation for papain and cathepsin L, respectively, at 37° C.

Polyclonal antibodies to NaCys1 (SEQ ID NO:2) were generated by conjugating purified NaCys1 to keyhole limpet haemocyanin. Purified NaCys1 (1 mg) was mixed with 0.5 mg of keyhole limpet haemocyanin (Sigma) in water to a final volume of 2 mL before an equal volume of 0.4% (v/v) glutaraldehyde (grade I) was added drop-wise to the protein solution over 5 min with stirring. The solution was allowed to stir for a further 1 h at RT before the reaction was terminated by addition of 1 mL of 1 M glycine (in PBS), pH 7.5. After stirring for a further 1 h at RT, the conjugated protein was dialysed overnight at 4° C. in 1×PBS using a 3500 MWCO SlideAlyzer (Pierce). The dialysed conjugated protein was made up to 10 mL with 1×PBS, aliquoted into 1 mL lots and stored at −20° C. until use. The protein conjugate (125 μg, 1 mL) was emulsified with an equal volume of Freund's complete adjuvant (Sigma) and injected subcutaneously into a rabbit. Booster immunizations were administered monthly and consisted of protein conjugate (125 μg) mixed with Freund's incomplete adjuvant (Sigma). Pre-immune serum was collected prior to injection, while immune sera were collected 2 weeks following immunization. The IgG fractions from the pre-immune and immune sera were purified on Protein-A Sepharose CL-4B (Amersham Pharmacia Biotech) according to the manufacturer's instructions and stored at −80° C.

Results

Four cDNAs encoding the cystatins NaCys1 (SEQ ID NO:2), NaCys2 (SEQ ID NO:4), NaCys3 (SEQ ID NO:6) and NaCys4 (SEQ ID NO:8) were isolated from the ornamental tobacco, *Nicotiana alata*. An alignment of the four amino acid sequences is shown in FIG. 1A. The amino acid sequences of the barley and maize cystatins is shown in FIG. 1B. The proteins encoded by the cDNAs were produced in a bacterial expression system and purified by metal affinity chromatography and RP-HPLC. The purified proteins eluted as single peaks and mass spectrometry was used to confirm the proteins had the mass predicted from the cDNA clones. About 40 mg of purified protein was obtained per litre of culture. A polyclonal antibody, raised against the cystatin NaCys1 could detect as little as 1 ng of each of the three bacterially expressed *N. alata* cystatins (NaCys1-3) on protein blots (FIG. 10). Cross reactivity between the antibody and all three cystatins was expected because they share 97-99% sequence identity at the amino acid level. These purified proteins were tested in combination with the defensin NaD1 in the fungal bioassays described in Example 3.

Figure 1E:
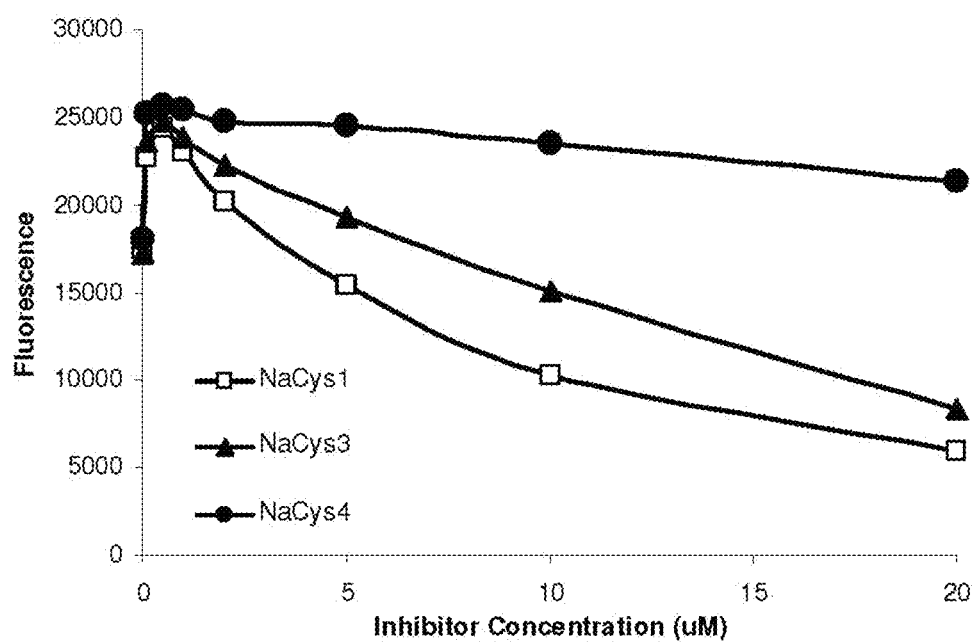

Bacterially expressed NaCys1 and NaCys3 were strong inhibitors of the cysteine proteinase papain while NaCys4 was a relatively poor inhibitor (FIG. 1D). Similarly NaCys1 and NaCys3 were better inhibitors of Cathepsin L than NaCys4 (FIG. 1E). The low cysteine proteinase activity of NaCys4 was attributed to the tryptophan to arginine substitution at position 80. This tryptophan is essential for protease binding (Bjork et al., 1996).

Example 2

Cloning and Recombinant Expression of Cysteine Proteinase Inhibitors from *Hordeum vulgare* and *Zea mays*

Cysteine proteinase inhibitor genes were isolated from barley and maize using standard molecular biology methods.

DNA Extraction

Leaf tissue samples (~100 mg) from barley (*Hordeum vulgare* cv Golden Promise) and maize (*Zea mays* cv SR73) seedlings were ground in liquid nitrogen. Genomic DNA was extracted using the DNeasy Plant Mini Kit (Qiagen) according to the manufacturer's instructions.

PCR Amplification and Cloning of Cystatin Genes

The oligonucleotide primers used to amplify barley and maize cysteine proteinase inhibitor genes were based on published sequences for Hv-CPI6 (Abraham et al. 2006) and CC6 (Massoneau et al. 2005), respectively. For Hv-CPI6, the primer sequences were: HvCys6F: 5' GCT CCG CGG TGG TAT GCA GAA GAA CTC GAC CAT GG 3' (SEQ ID NO:31) and HvCys6R: 5' GGA GCT CTT AGC CGC CGG CAG C 3' (SEQ ID NO:32); for CC6, the primer sequences were: CC6F: 5' GCT CCG CGG TGG TAT GTC CGC GAG AGC TCT TCT C 3' (SEQ ID NO:33) and CC6R: 5' GGA GCT CTC AGC TGG CCG GCG CGA AG 3' (SEQ ID NO:34). PCR reactions contained 5× Phusion HF buffer (10 uL, Finnzymes), dNTP mix (2.5 mM each, 4 uL), forward and reverse primers (10 uM, 2.5 uL each), Phusion DNA Polymerase (2 U/uL, 0.5 uL), sterile distilled water (29.5 uL) and genomic DNA (1 uL). Initial denaturation occurred at 98° C. for 30 s, followed by 30 cycles of 98° C. for 10 s, 69° C. for 15 s and 72° C. for 20 followed by a final elongation step of 72° C. for 5 min. 5' Deoxyadenosines were added to the resultant ~400 by PCR products by incubating the purified PCR product (6 uL) with 10× Taq PCR buffer (1 uL, Scientifix), Taq DNA polymerase (1 uL, Scientifix) and dATP (2 uL, 1 mM) at 72° C. for 20 min. The A-tailed PCR products were then cloned into the vector pGEM-T Easy (Promega) which was then used to transform electrocompetent E. coli cells (TOP10, Invitrogen) according to the manufacturer's instructions. Plasmid DNA was isolated using the Wizard Plus SV Miniprep kit (Promega) and vector inserts were sequenced (Macrogen) using the pGEM-T Easy-specific SP6 and T7 primers.

Recombinant Protein Expression and Purification

DNA encoding Hv-CP16 (SEQ ID NO:14) and CC6 (SEQ ID NO:16) was PCR-amplified for subcloning into pHUE for recombinant protein expression in E. coli (Cantanzariti et al. 2004). For Hv-CP16, a native Sac II restriction site near the 5' end of the gene encoding the mature protein was removed by a single base substitution (C to G) using the primer MHvCys6F2: 5' GCC ACC TCG GCC CTC GGC CGG CGC GGC 3' (SEQ ID NO:35) (substituted base underlined) in combination with HvCys6R (SEQ ID NO:32). The resultant PCR product was then used as the template for a nested PCR reaction using the primer MHvCys6F: 5' GCT CCG CGG TGG TGC CAC CTC GGC CCT C 3' (SEQ ID NO:36) in combination with HvCys6R (SEQ ID NO:32). For CC6, DNA encoding the mature protein was PCR-amplified using the primers MCC6: 5' GCT CCG CGG TGG TGG GCA GCC GCT CGC 3' (SEQ ID NO:37) and CC6R2: 5' GGG TAC CTC AGC TGG CCG GCG 3' (SEQ ID NO:38). PCR reactions were performed essentially as described above. Resultant PCR products were A-tailed and cloned into pGEM-T Easy; inserts were excised using Sac II and Sac I for Hv-CP16 and Sac II and Kpn I for CC6, extracted from agarose gels using the MinElute Gel Extraction kit (Qiagen) and ligated into pHUE. This was used to transform TOP10 E. coli cells from which plasmid DNA was isolated and used to transform BL21 (DE3) Star E. coli cells (Invitrogen).

Recombinant expression and purification of Hv-CP16 (SEQ ID NO:14) and CC6 (SEQ ID NO:16) were performed as described for the cysteine proteinase inhibitors from N. alata.

Results

The coding regions from the Hv-CP16 and CC6 genies were cloned. The DNA sequence for Hv-CP16 matched the published sequence (GenBank accession number AJ748341). The DNA sequence for CC6 had a silent base change compared to the published sequence (GenBank accession number AM055635). DNA encoding mature Hv-CP16 and CC6 was PCR-amplified and sub-cloned into pHUE. The protein was produced in a bacterial expression system and purified by metal affinity chromatography. The purified proteins were tested in combination with the defensin NaD1 in the fungal bioassays described in Example 3.

```
ATGCAGAAGAACTCGACCATGGGGAGACCGCTCCTCCTGCTCGCCCTCCTGGCCACGGCC
 M  Q  K  N  S  T  M  G  R  P  L  L  L  L  A  L  L  A  T  A

CTCGCAGCCACCTCGGCCCTCGGCCGCCGCGGCGTGCTTCTGGGCGGGTGGAGCCCCGTC
 L  A  A  T  S  A  L  G  R  R  G  V  L  L  G  G  W  S  P  V

AAGGACGTGAACGACCCGCACGTCCAGGAGCTAGGCGGGTGGGCGGTGGCCCAGCACGCC
 K  D  V  N  D  P  H  V  Q  E  L  G  G  W  A  V  A  Q  H  A

AGCCTAGCCAAGGACGGGCTGCTCTTCCGCCGGGTGACGCGCGGCGAGCAGCAGGTGGTG
 S  L  A  K  D  G  L  L  F  R  R  V  T  R  G  E  Q  Q  V  V

TCCGGGATGAACTACCGCCTCTTCGTGGTCGCGGCGGACGGCTCCGGCAAGAGGGTGACC
 S  G  M  N  Y  R  L  F  V  V  A  A  D  G  S  G  K  R  V  T

TATCTCGCGCAGATCTACGAGCACTGGAGCAGGACCCGCAAGCTCACGTCCTTCAAGCCG
 Y  L  A  Q  I  Y  E  H  W  S  R  T  R  K  L  T  S  F  K  P

GCTGCCGGCGGCTAA
 A  A  G  G  -
```

Cloned full-length DNA sequence of Hv-CP16 (SEQ ID NO:13) and deduced amino acid sequence (SEQ ID NO:14). The underlined amino acid sequence represents the signal peptide. For recombinant expression of the mature protein, the underlined base was changed (C to G silent change) in order to remove a native Sac II site, allowing straightforward sub-cloning into pHUE.

```
ATGTCCGCGAGAGCTCTTCTCCTGACGACCGCGACGCTGCTCCTGCTCGTCGCCGCTGCG
 M  S  A  R  A  L  L  L  T  T  A  T  L  L  L  L  V  A  A  A

CGTGCGGGGCAGCCGCTCGCCGGCGGGTGGAGCCCGATCAGGAACGTCAGCGACCCGCAC
 R  A  G  Q  P  L  A  G  G  W  S  P  I  R  N  V  S  D  P  H

ATCCAGGAGCTCGGCGGCTGGGCGGTGACGGAGCACGTCAGGCGGGCCAACGACGGCTG
 I  Q  E  L  G  G  W  A  V  T  E  H  V  R  R  A  N  D  G  L

CGGTTCGGCGAGGTGACGGGCGGCGAGGAGCAGGTGGTGTCCGGGATGAACTACAAGCTC
 R  F  G  E  V  T  G  G  E  E  Q  V  V  S  G  M  N  Y  K  L
```

```
-continued
GTCCTTGACGCCACGGACGCCGACGGCAAGGTCGCGGCGTACGGGGCCTTCGTGTACGAG
 V  L  D  A  T  D  A  D  G  K  V  A  A  Y  G  A  F  V  Y  E CAGTCGTGGACCAACACCCGCGAGCTCGTGTCCTTCGCGCCGGCCAGCTGA
 Q  S  W  T  N  T  R  E  L  V  S  F  A  P  A  S  -
```

Cloned full-length DNA sequence of CC6 (SEQ ID NO:15) and deduced amino acid sequence (SEQ ID NO:16). The silent base change (C to T) is underlined. The underlined amino acid sequence represents the signal peptide.

Example 3

Recombinant Expression of StPin1A

The serine proteinase inhibitor StPin1A (SEQ ID NO:10), isolated from potato (*Solanum tuberosum*) was previously described (as Pot1A) in U.S. Pat. No. 7,462,695 "Insect chymotrypsin and inhibitors thereof" and U.S. Published Application No. 2007-0277263 "Multi-Gene Expression Vehicle" and is incorporated herein by reference.

Recombinant StPin1A (SEQ ID NO:10), CI-1B, CI-2 and At2g38870 were produced using the pHUE expression system in *E. coli* as described in Example 1 with the following modifications. DNA encoding StPin1A was amplified by PCR using the following conditions. The primers were: Sac2StPin1A5': 5' CTC CGC GGT GGT AAG GAA TCG GAA TCT GAA TCT TG 3' (SEQ ID NO:39); Pot1Sal13': 5' GGT CGA CTT AAG CCA CCC TAG GAA TTT GTA CAA CAT C 3' (SEQ ID NO:40). PCR reactions contained 2× GoTaq Mastermix (25 µL, Promega), Sac2Pot15' primer (10 µM, 2 µL), Pot1Sal13' primer (10 µM, 2 µL), sterile distilled water (16 µL) and pGEM-T Easy-StPot1A plasmid DNA (~20 ng, 5 µL) as template. Initial denaturing occurred at 94° C. for 2 min, followed by 30 cycles of 94° C. for 1 min, 60° C. for 1 min and 72° C. for 1 min followed by a final elongation step of 72° C. for 10 min. DNA encoding for the mature domain of the barley type-I inhibitors CI-1B and CI-2 and the *Arabidopsis* type I inhibitor At2g38870 was ordered from Genscript. Inserts were excised from the pUC57 vector using Sac II and Sac I, extracted from agarose gels using the Perfectprep kit (Eppendorf) and ligated into pHUE which was then used to transform TOP10 *E. coli* cells. Plasmid DNA was isolated and then used to transform *E. coli* (DE3) CodonPlus) cells and proteins were expressed as described in example 3.

Single colonies of transformed *E. coli* (BL21 (DE3) CodonPlus) were used to inoculate 20 mL of 2YT media (10 mL, 16 g/L tryptone, 10 g/L yeast extract, 5 g/L NaCl) containing ampicillin (0.1 mg/mL), chloramphenicol (0.34 mg/mL) and tetracycline (0.1 mg/mL) and grown overnight with shaking at 37° C. This culture was used to inoculate fresh 2YT media (1 L) containing antibiotics which was then incubated at 37° C. with shaking until an optical density (600 nm) of ~0.8. IPTG was added (1 mM final concentration) and the culture grown for a further 3 h. Cells were harvested and protein extracted as described in Example 1 except that the imidazole was removed from the eluted protein fractions by dialysis through 0.22 µm nitrocellulose dialysis tubing in a buffer containing 50 mM Tris-HCl and 100 mM NaCl, pH 8.0. The hexahistidine-tagged ubiquitin was cleaved from the recombinant protein as described in Example 1. The cleaved protein was subsequently purified using a System Gold HPLC (Beckman) coupled to a detector (model 166, Beckman) and a preparative C8 column (22× 250 mm, Vydac). Protein samples were loaded in buffer A (0.1% [v/v] trifluoroacetic acid) and eluted with a step gradient of 0-60% (v/v) buffer B (60% [v/v] acetonitrile in 0.089% [v/v] trifluoroacetic acid) over 5 min and 60-100% buffer B over 20 min with a flow rate of 10 mL/min. Proteins were detected by monitoring absorbance at 215 nm. Protein peaks were collected manually and analyzed by SDS-PAGE.

Polyclonal antibodies to StPin1A were prepared as described in Example 1.

Results

Figure 2C:
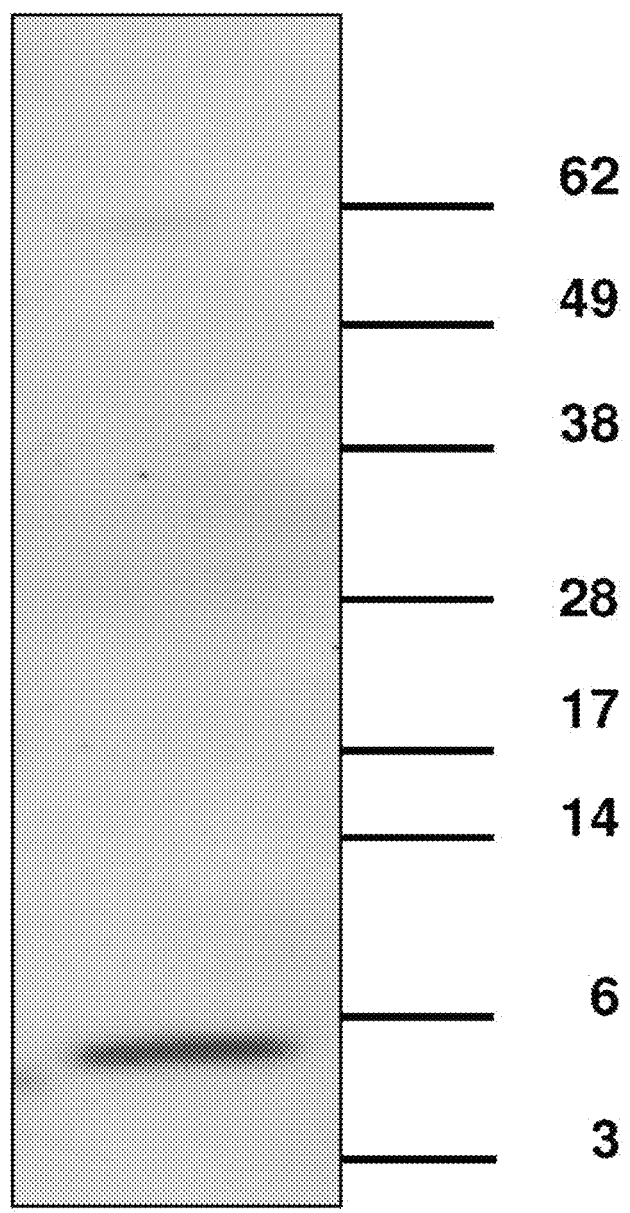

The DNA encoding the *Solanum tuberosum* Type I Proteinase Inhibitor StPin1A, the barley type I inhibitors CI-1B and CI-2, and the *Arabidopsis* proteinase inhibitor At2g38870 was cloned into the pHUE bacterial expression vector and expressed protein was purified by metal affinity chromatography and RP-HPLC. Purified proteins eluted as a single peak and mass spectrometry confirmed the proteins had the sequence predicted from the DNA clone with no post-translational modifications. About 15 mg of purified StPin1A was obtained per litre of culture. A polyclonal antibody, raised against the bacterially expressed StPin1A readily detected 50 ng of StPin1A on protein blots (FIG. 2). Purified StPin1A was tested in combination with the defensin NaD1 in the fungal bioassays described in Example 4. Purified CI-1B, CI-2 and At2g38870 were tested in combination with the defensin NaD1 in the fungal bioassays described in Example 9.

Example 4

Inhibition of the Growth of *Fusarium graminearum* in the Presence of NaD1 and Serine or Cysteine Proteinase Inhibitors In Vitro The inhibitory effects of defensin (NaD1) in combination with serine or cysteine proteinase inhibitors on the growth of *Fusarium graminearum* (Australian isolate CS3005 provided by CSIRO Plant Industry, St. Lucia, Queensland, Australia) was measured essentially as described by Broekaert et al, 1990. Spores were isolated from sporulating cultures growing in synthetic nutrient poor broth (SNPB). The cultures were grown in half strength potato dextrose broth (PDB) for 1-2 weeks at room temperature, before spores were collected by passing the culture through sterile tissue paper to remove hyphal matter. Spore concentrations were measured using a hemocytometer.

Figure 3A:
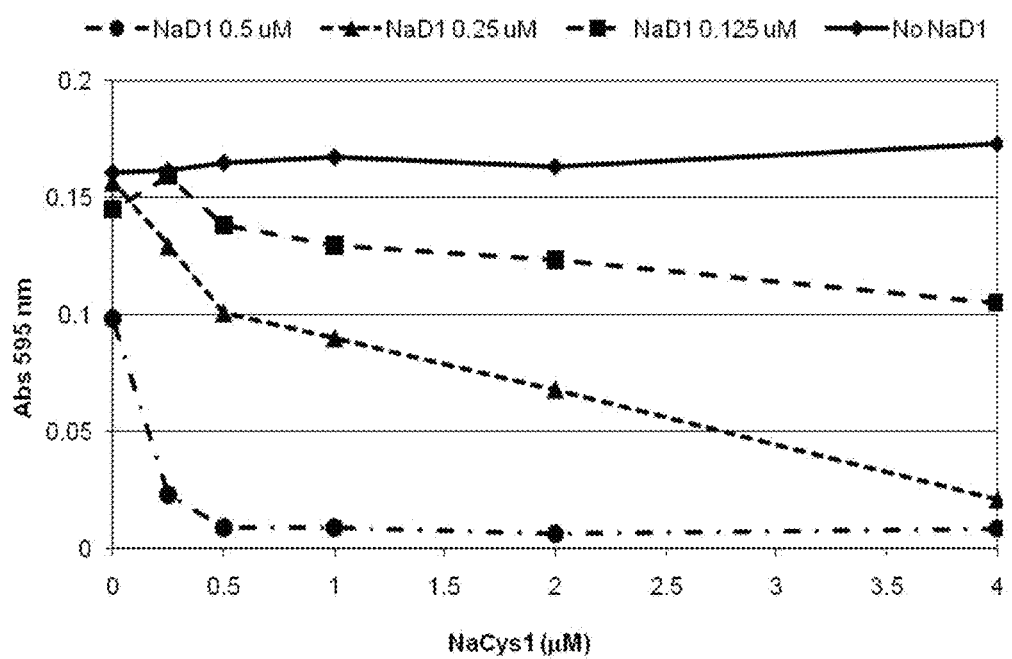
FIGS. 3A through 3F are graphical representations and FIG. 3H is a micrograph showing the effect of combinations of the defensin NaD1 (SEQ ID NO:12) and cysteine proteinase inhibitors on the growth of *Fusarium graminearum* in vitro. Fungal growth was measured by the increase in optical density at 595 nm (A595) achieved at 24-26 hours after inoculation of the growth medium, (vertical axis) and is plotted against proteinase inhibitor concentration (μM) on the horizontal axis. The solid line connects sample results obtained in the presence of 0 μM NaD1; Dashed line: 0.125 μM NaD1; Dotted line: 0.25 μM NaD1; Dot-Dash line: 0.5 μM NaD1.
Figure 3B:
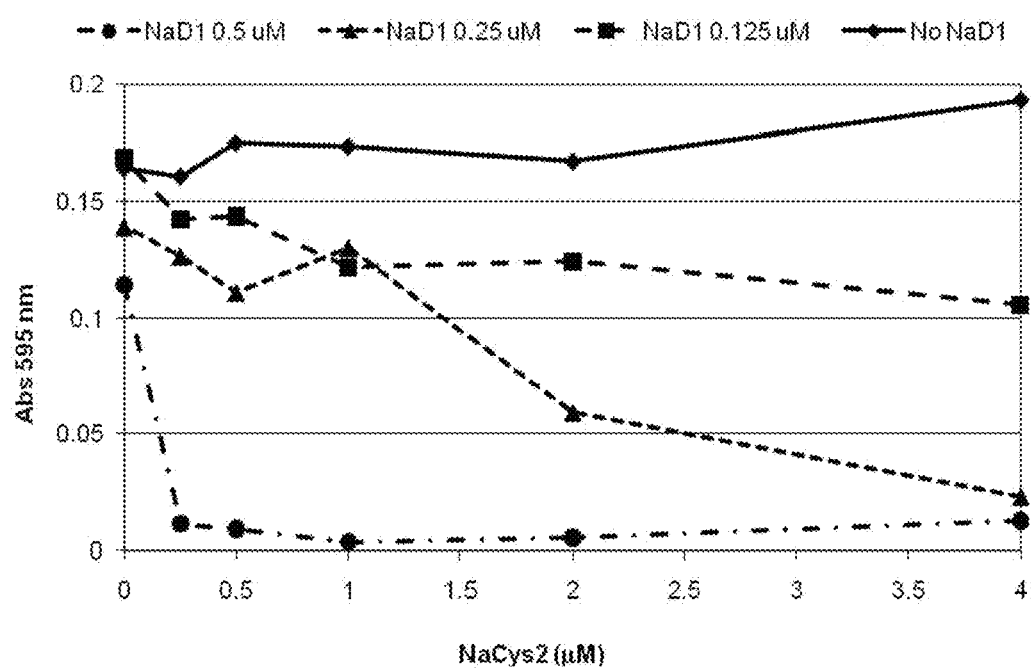
Figure 3C:
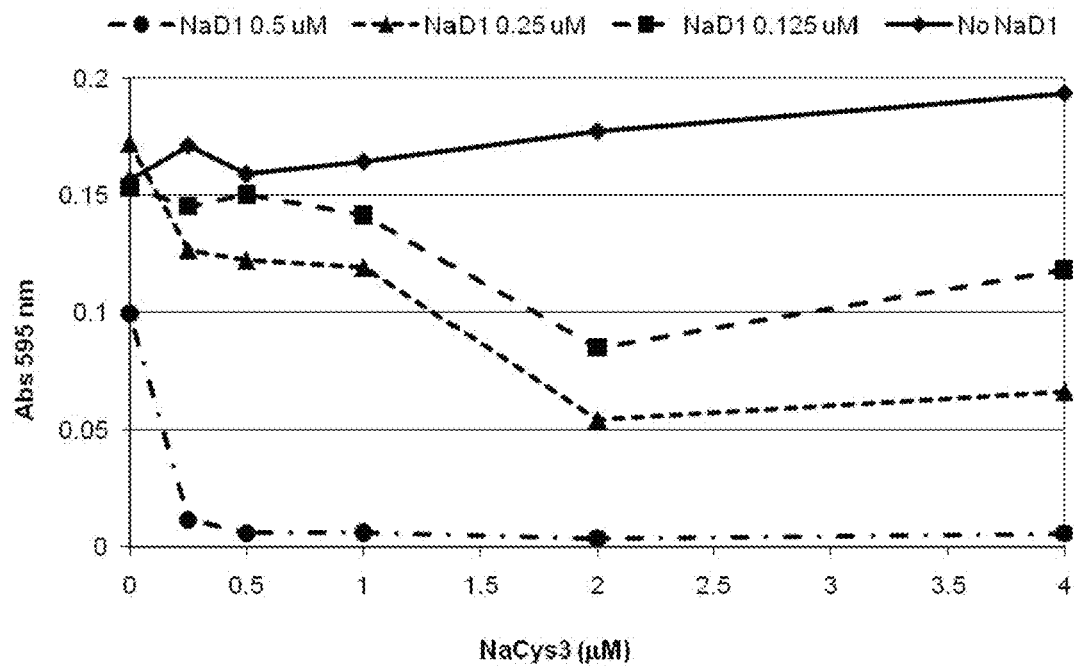
Figure 3D:
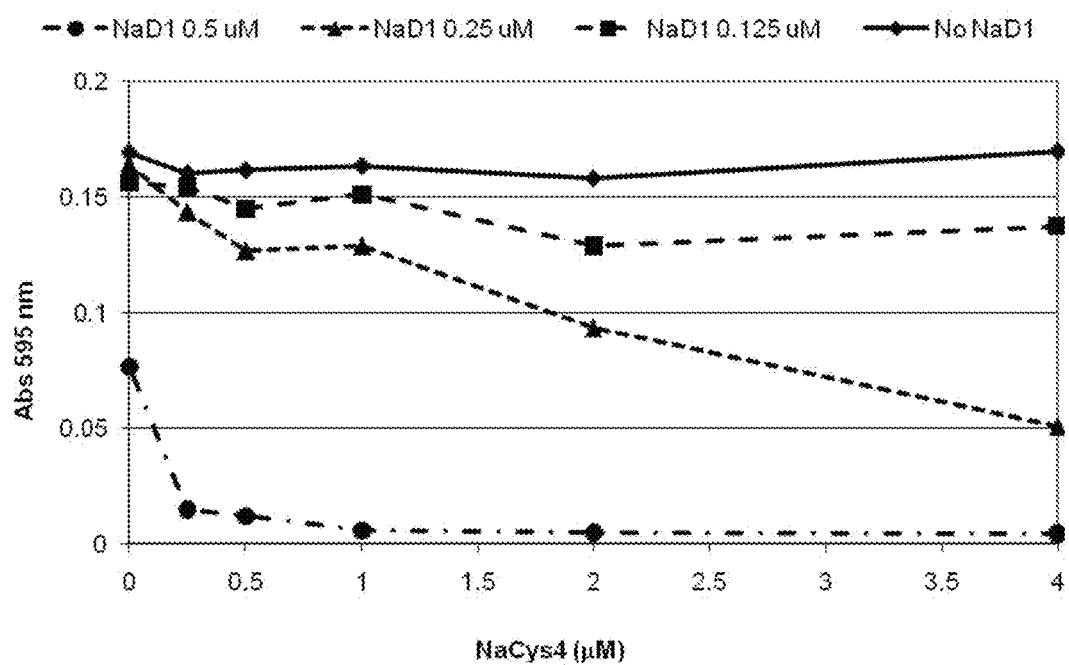
Figure 3E:
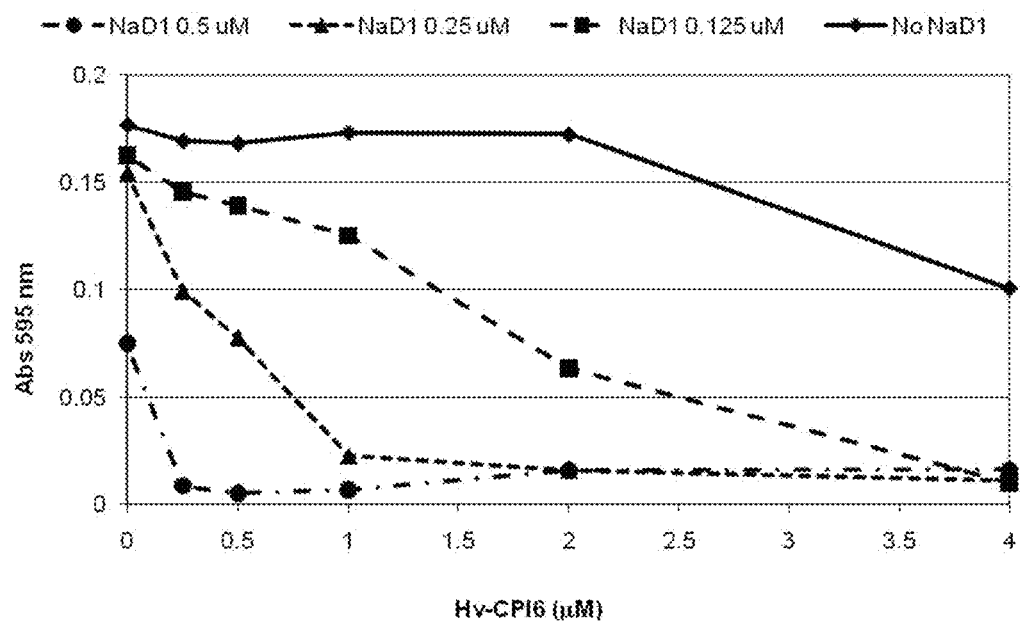
Figure 3F:
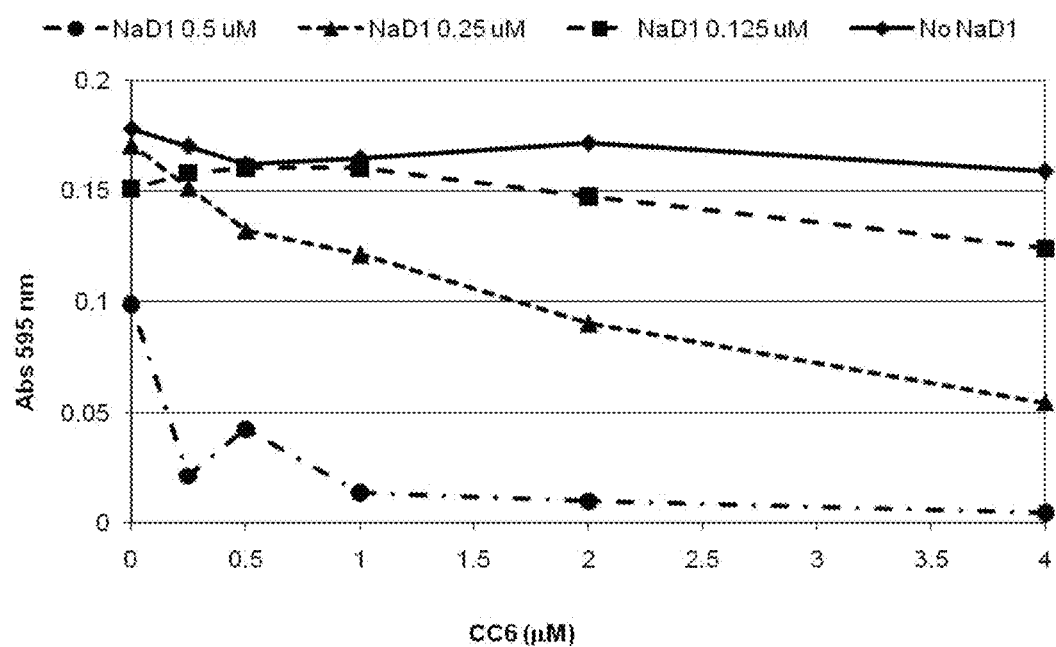
Figure 3H:
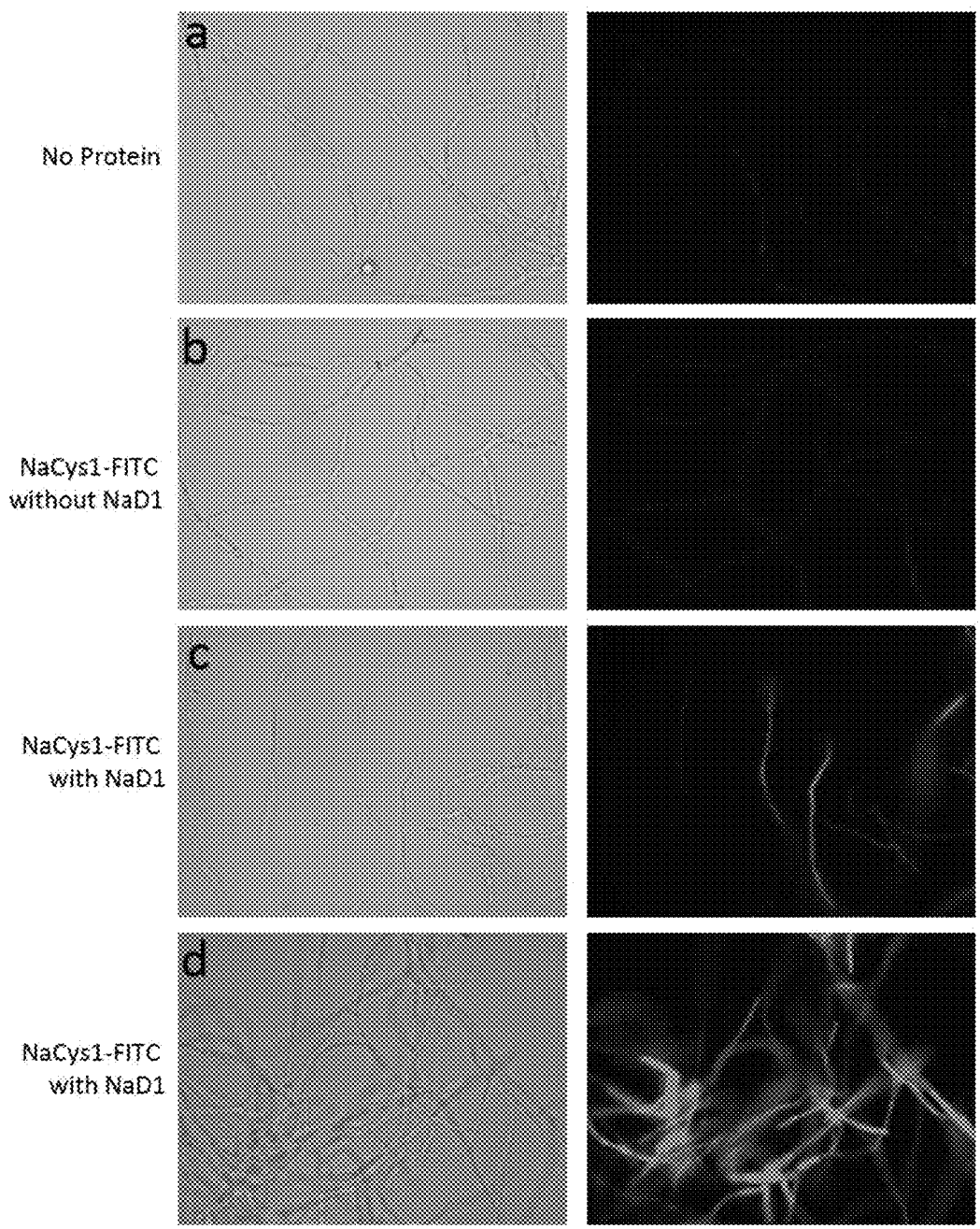

NaD1, prepared as described in the detailed descriptions, was diluted to provide a series of stock solutions with 10× the final concentrations shown in FIG. 3A. Recombinant NaCys1 (SEQ ID NO:2), NaCys2 (SEQ ID NO:4), NaCys3 (SEQ ID NO:6) and NaCys4 (SEQ ID NO:8) were prepared as described in Example 1 and stock solutions (10×) were prepared in H₂O. Trypsin inhibitor type I-P from bovine pancreas (Anderson and Kingston, 1983) was purchased from Sigma (T0256). Recombinant StPin1A, NaPin1A and NaPin1B were prepared as described in Example 3. The primers for amplification of NaPin1A and NaPin1B for cloning into the pHUE expression vector are NaPin1Afw (SEQ ID NO:41) and NaPin1Arv (SEQ ID NO:42), NaPin1Bfw (SEQ ID NO:43) and NaPin1Brv (SEQ ID NO:44) respectively. Soybean trypsin inhibitor Type II-S, Soybean Bowman-Birk inhibitor, cystatin from chicken egg white and the cysteine proteinase inhibitor E64 were purchased from Sigma (cat. numbers T9128, T9777, C8917 and E3132 respectively). NaPl was purified from plant tissue as described by Lee et al. 1999.

Antifungal assays were conducted in 96 well microtiter trays essentially as described in the detailed description (analysis of antifungal activity). Wells were loaded with 10 µL of filter sterilized (0.22 µm syringe filter, Millipore) NaD1 (10× stock for each final concentration) or water, 10 µL of filter sterilized (0.22 µm syringe filter, Millipore) proteinase inhibitor (10× stock for each final concentration) or water and 80 µL of $5×10^4$ spores/mL in ½ strength PDB. The plates were incubated at 25° C. Fungal growth was assayed by measuring optical density at 595 nm (A595) using a microtitre plate reader (SpectraMax Pro M2; Molecular Devices). Each test was performed in quadruplicate.

Immunofluorescence microscopy was used to determine whether NaCys1 could enter the cytoplasm of *F. graminearum* hyphae that had been treated with NaD1. NaCys1 was labelled with the fluorescent tag fluorescein isothiocyanate (FITC). Lyophilized NaCys1 (1 mg) was dissolved in 500 µL of 50 mM HEPES buffer (pH 8.0). The fluorescent tag fluorescein isothiocyanate (FITC, Invitrogen) was added to a final concentration of 5 mM. The reaction was incubated at RT for 2 h with gentle stirring before centrifugation (13,000 rpm, 10 min) to remove any precipitated protein. An Ultracell 3K MWCO spin column (Millipore) was used to remove any unbound FITC. The FITC-labelled NaCys1 was resuspended in water and the protein concentration was determined using the BCA protein assay (Pierce).

*Fusarium graminearum* hyphae were grown for 18 h in half-strength PDB (10 mL) with vigorous shaking at 25° C. from a starting spore suspension of $5×10^4$/mL. Hyphae (100 µL) were then treated with or without NaCys1-FITC (4 µM) in the presence or absence of NaD1 (0.5 µM). After 1 h, hyphae were pelleted by centrifugation (13,000 rpm, 10 min) and unbound NaCys1-FITC was removed by washing once in 0.6 M KCl and twice in PBS. Hyphae were then visualized by fluorescence microscopy using an Olympus BX51 fluorescence microscope. Fluorescence was detected using an MWIB filter (excitation wavelength of 460-490 nm). Images were captured using a SPOT RT 3CCD camera (Diagnostic Instruments) and processed using Adobe Photoshop.

Results

Figure 4A:
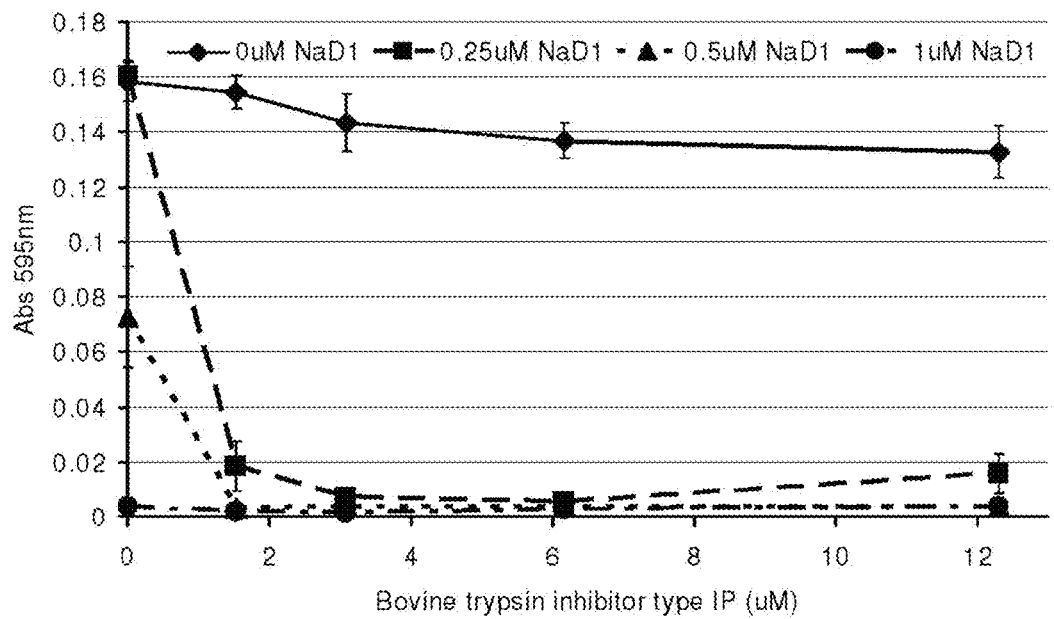
Figure 4B:
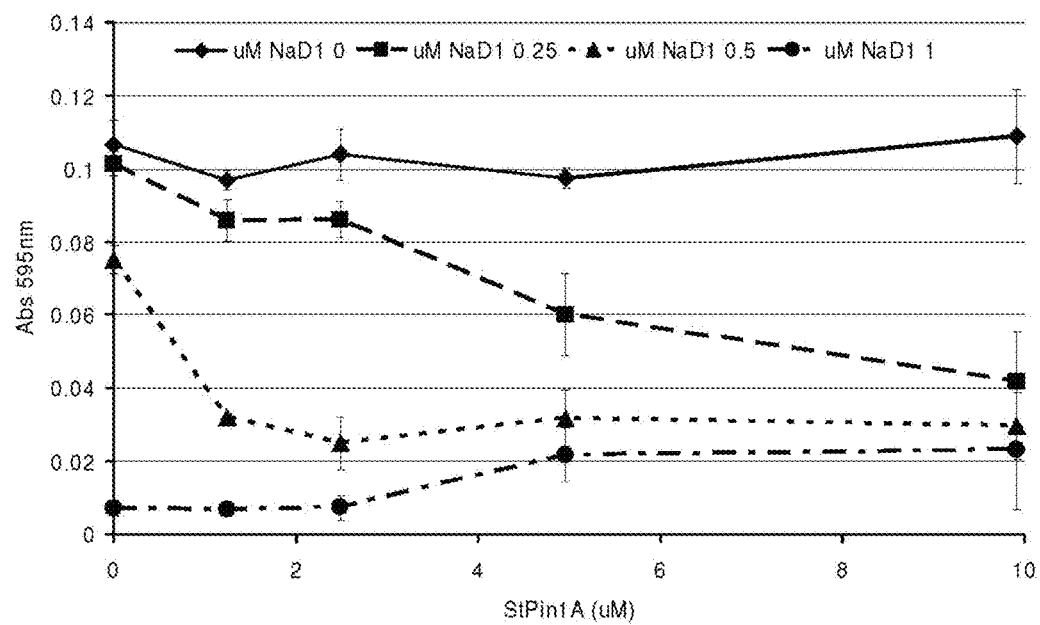
Figure 4C:
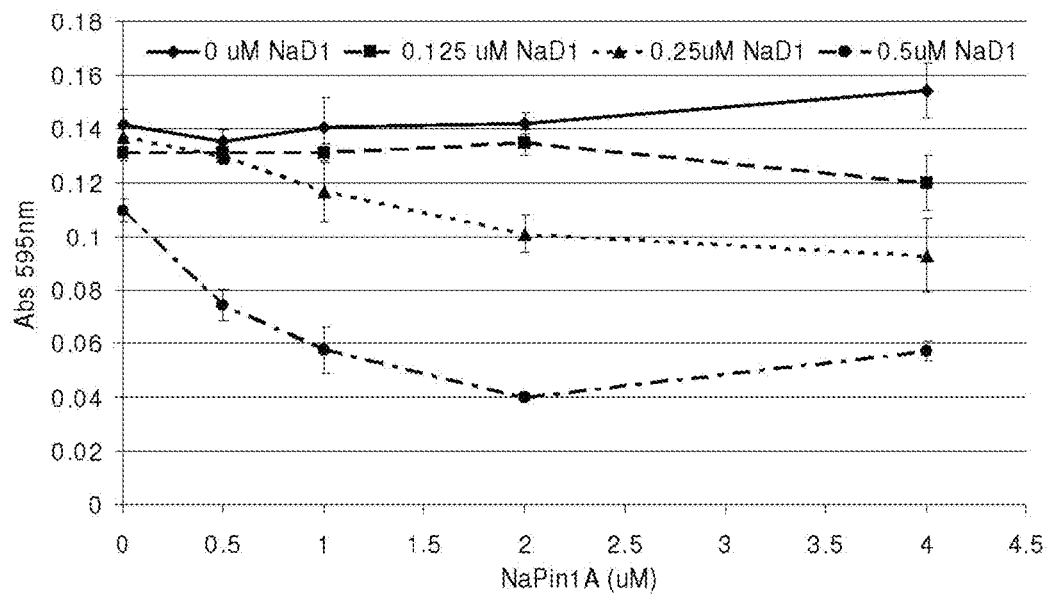
Figure 4D:
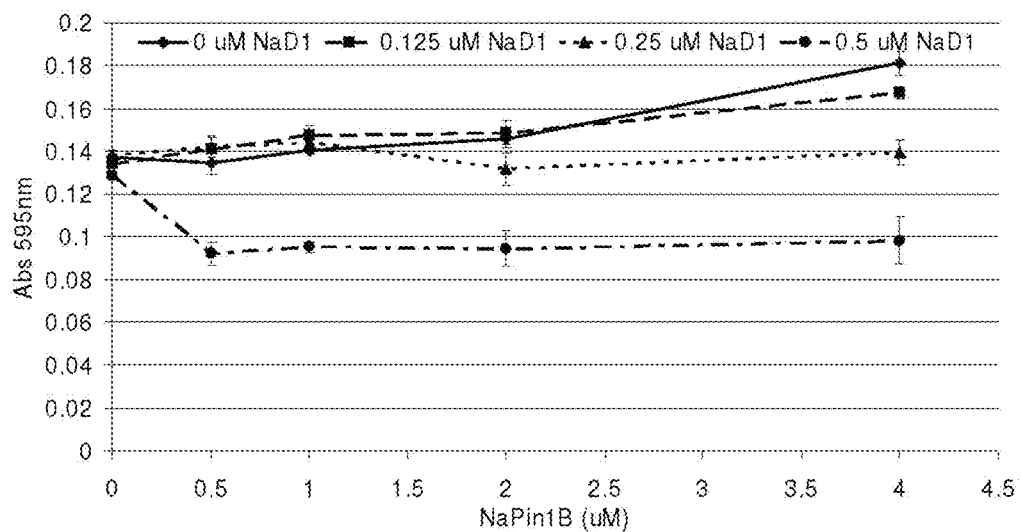

The NaD1 defensin had a synergistic effect on the inhibitory activity of all four of the *Nicotiana alata* cystatins (~10.8 kDa) and the cystatins from barley (11.1 kDa) and maize (10.1 kDa). (FIGS. 3A-3F) as well as on the inhibitory activity of Bovine Trypsin Inhibitor type I-P (6.5 kDa) (FIG. 4A) and the potato Type 1 proteinase inhibitors StPin1A, NaPin1A and NaPin1 B (~8.5 kDa) (FIGS. 4B-4D). Apart from the barley cystatin, none of these proteinase inhibitors had any fungicidal activity when they were not combined with NaD1. Indeed, the *N. alata* cystatins NaCys1, NaCys2 and NaCys3 had no effect on hyphal growth at concentrations up to 18.5 uM in the absence of NaD1.

Figure 4E:
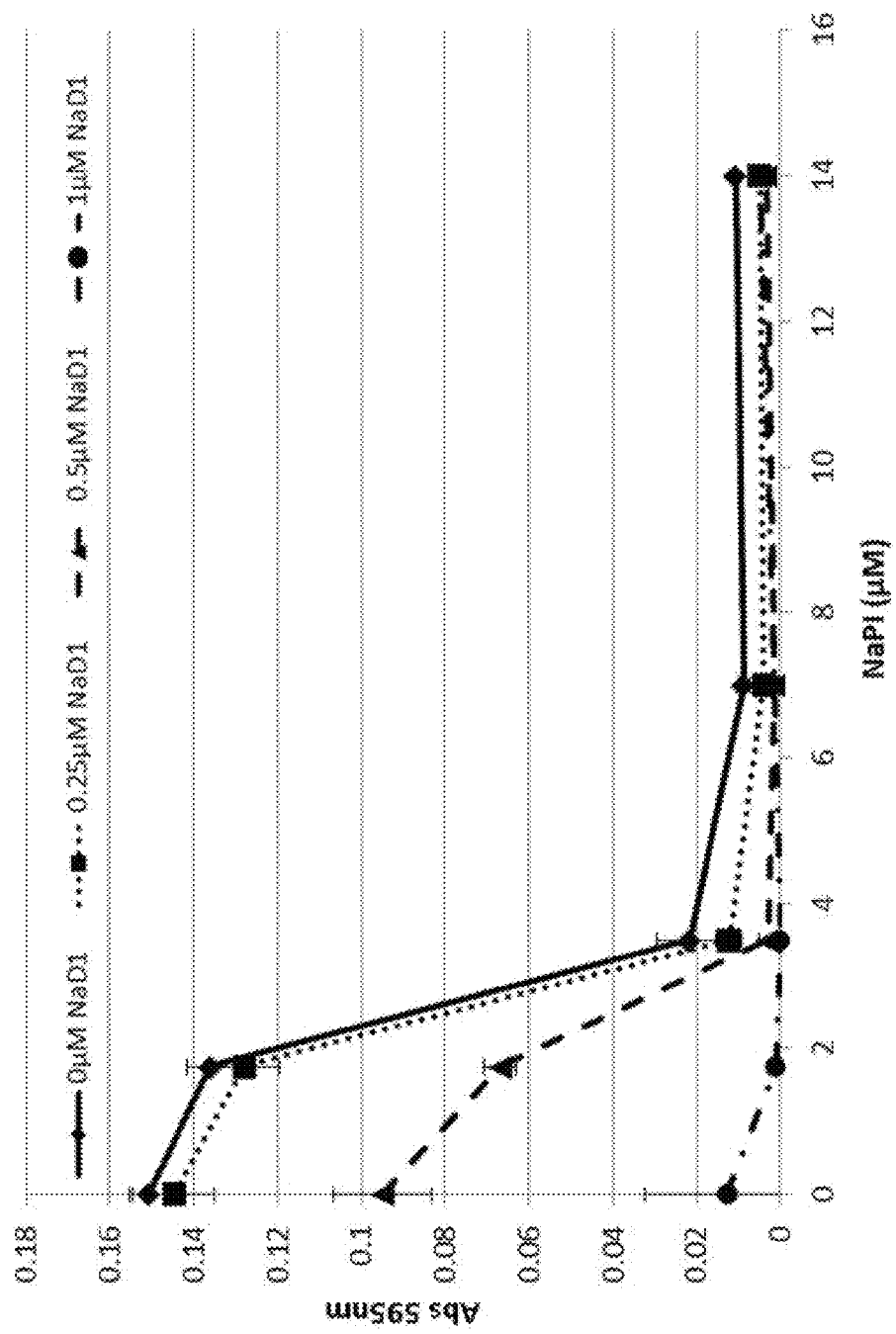

Synergy calculations are presented in FIG. 3G for the cystatins and 4E for the serine proteinase inhibitor wherein Ee is the expected effect from the additive response according to Limpel's formula (Richer, 1987) expressed as percent inhibition and Io is the percent inhibition observed. Synergy, that is, Io values higher than Ee values was obtained with all four *Nicotiana alata* cystatins and the cystatins from barley and maize (FIG. 3G) and the serine proteinase inhibitors, Bovine Trypsin Inhibitor type 1-P, StPin1A, NaPin1A and NaPin1B (FIG. 4E).

Plant cystatins (phytocystatins) with some antifungal activity have been reported previously (Joshi et al., 1998, Martinez et al., 2003). They are distinct from the cystatins tested in this application because they have direct antifungal activity, whereas apart from the barley cystatin, the PIs tested in this application have no affect on fungal growth in the absence of defensin. Nevertheless the antifungal activity of the barley cystatin was much enhanced in the presence of the NaD1 defensin. The proteinase inhibitory activity of the cystatins may not be essential for their antifungal activity. We observed that bacterially expressed NaCys1 and NaCys3 were strong inhibitors of the cysteine proteinase papain while NaCys4 was a relatively poor inhibitor (FIG. 1D). Similarly NaCys1 and NaCys3 were better inhibitors of Cathepsin L than NaCys4 (FIG. 1E). The low cysteine proteinase activity of NaCys4 was attributed to the tryptophan to arginine substitution at position 80. This tryptophan is essential for protease binding (Bjork et al., 1996). Martinez and co-workers (2003) have also observed that the antifungal activity of the barley cystatin Hv-CPI is not associated with its proteinase inhibitory activity.

The serine proteinase inhibitors, Soybean trypsin inhibitor Type II-S (21 kDa) and Soybean Bowman-Birk inhibitor (7.9 kDa) and the cysteine proteinase inhibitors chicken egg white cystatin (12.7 kDa) and E64 (357Da), had no fungicidal activity on their own or in combination with NaD1 under the conditions used for the fungal bioassay. The serine proteinase inhibitor NaPl inhibited the growth of *Fusarium graminearum* when used alone but did not act in synergy with the defensin NaD1 (FIG. 4E). Without wishing to be bound by any particular theory, it is believed that the observation that not all proteinase inhibitors act in synergy with defensins may be a reflection of their size, that is, they are too large or have inappropriate physical properties (eg. charge) to enter the hyphal cytoplasm via the pores created by defensin. The soybean trypsin inhibitor Type-II-S (21 kDa) would fall into this group. Alternatively they may enter hyphae in the presence of defensin but fail to bind to any targets that affect fungal growth.

Example 5

Inhibition of the Growth of *Fusarium graminearum* in the Presence of Defensins from Tomato or Petunia and Serine or Cysteine Proteinase Inhibitors In Vitro Defensins were isolated from tomato (Tomdef2, SEQ ID NO:22), U.S. patent application Ser. No. 12/362,657) and petunia (PhD1A, SEQ ID NO:24) flowers as described for the *N. alata* defensin NaD1 in the detailed description. Their identity and sequence was established by mass spectrometry, N-terminal sequencing and isolation of the encoding DNA. Their effect on the growth of *Fusarium graminearum* was measured in combination with serine or cysteine proteinase inhibitors as described for the NaD1 defensin in Example 4.

Results

Figure 5B:
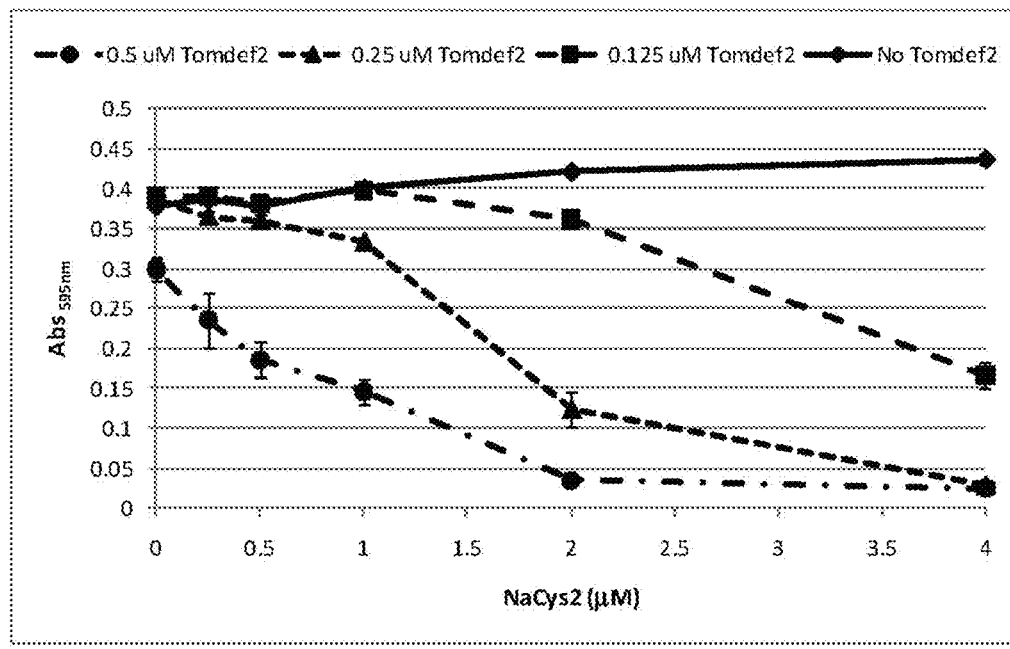
FIGS. 5B through 5I are graphical representations showing the effects of combinations of the tomato defensin Tomdef2 or the petunia defensin PhD1A and the proteinase inhibitors on the growth *Fusarium graminearum* in vitro. Fungal growth was measured by the increase in optical density at 595 nm (A595) achieved 40 hours after inoculation of the growth medium, (vertical axis) and is plotted against proteinase inhibitor concentration (μM) on the horizontal axis. The solid line connects sample results obtained in the presence of 0 μM defensin; Dashed line: 0.125 μM defensin; Dotted line: 0.25 μM defensin; Dot-Dash line: 0.5 μM defensin.
Figure 5C:
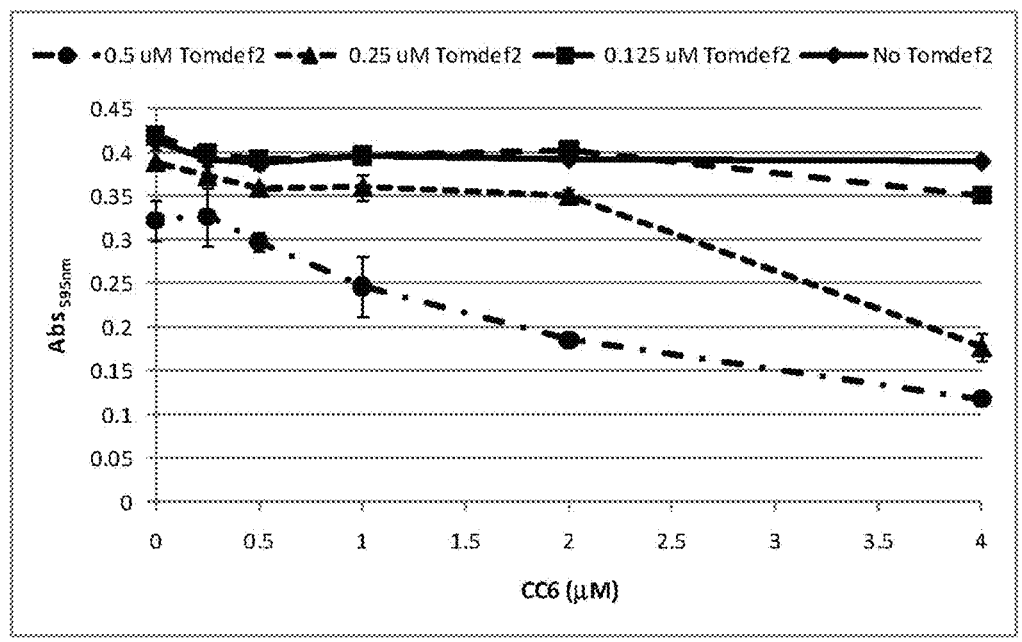
Figure 5D:
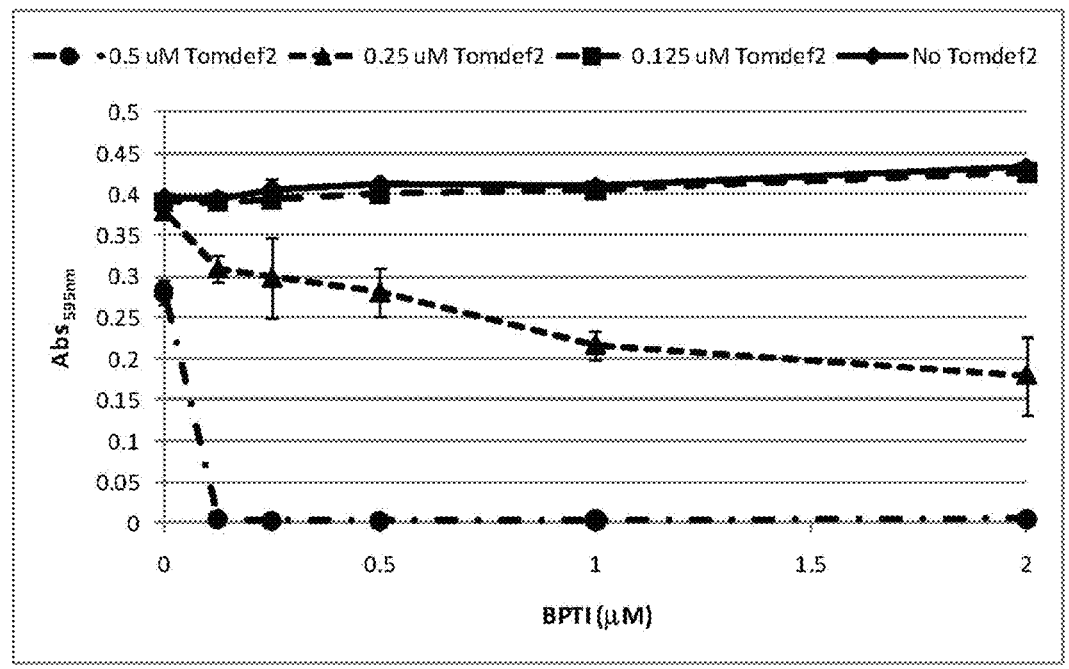
Figure 5E:
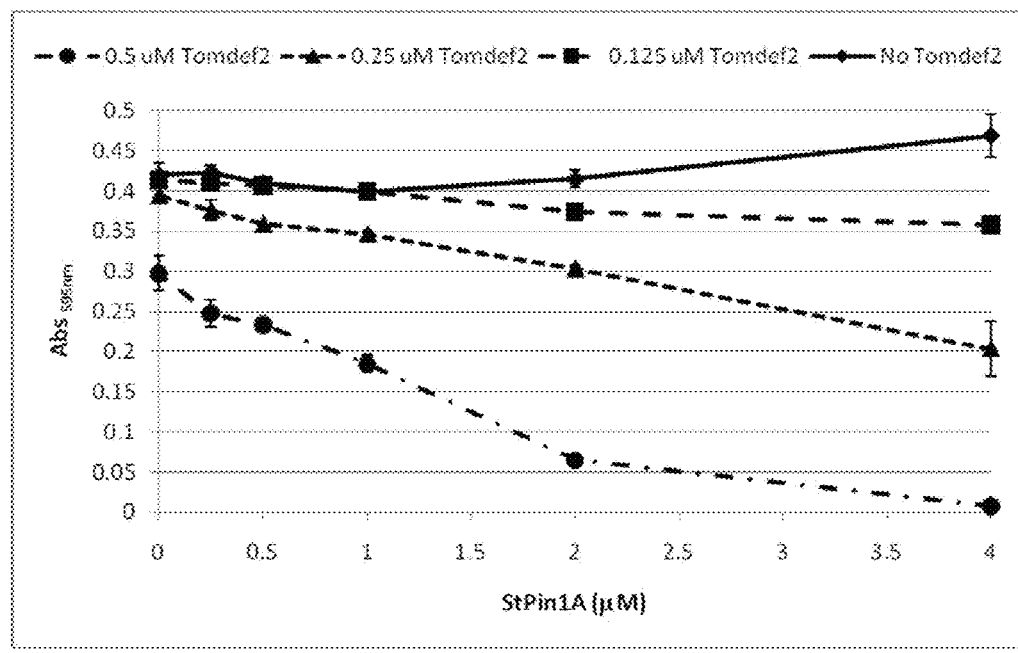
Figure 5F:
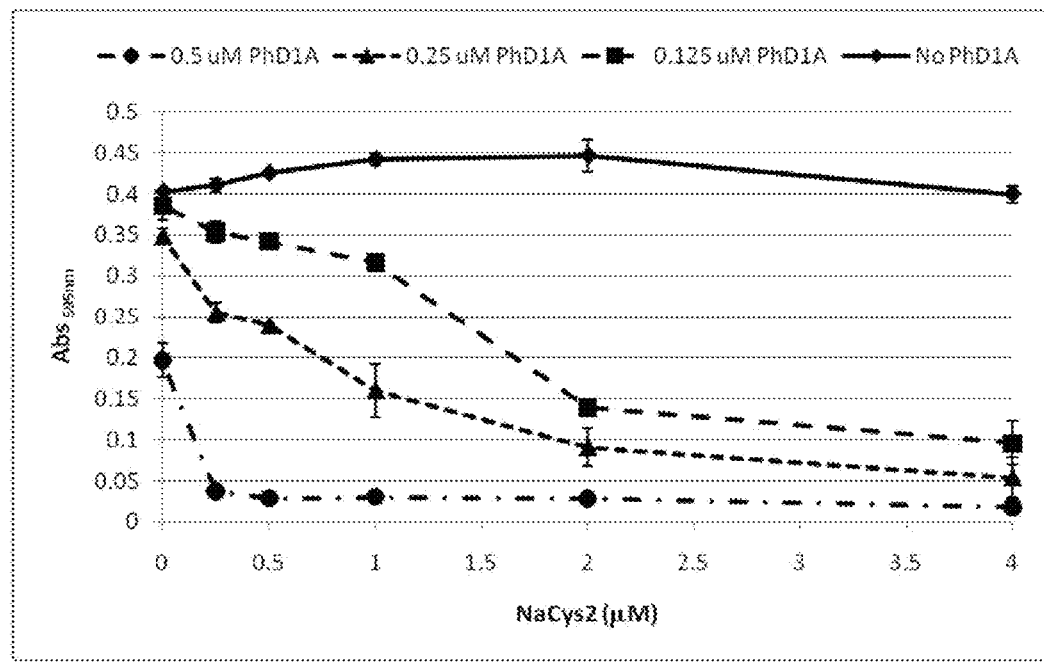
Figure 5G:
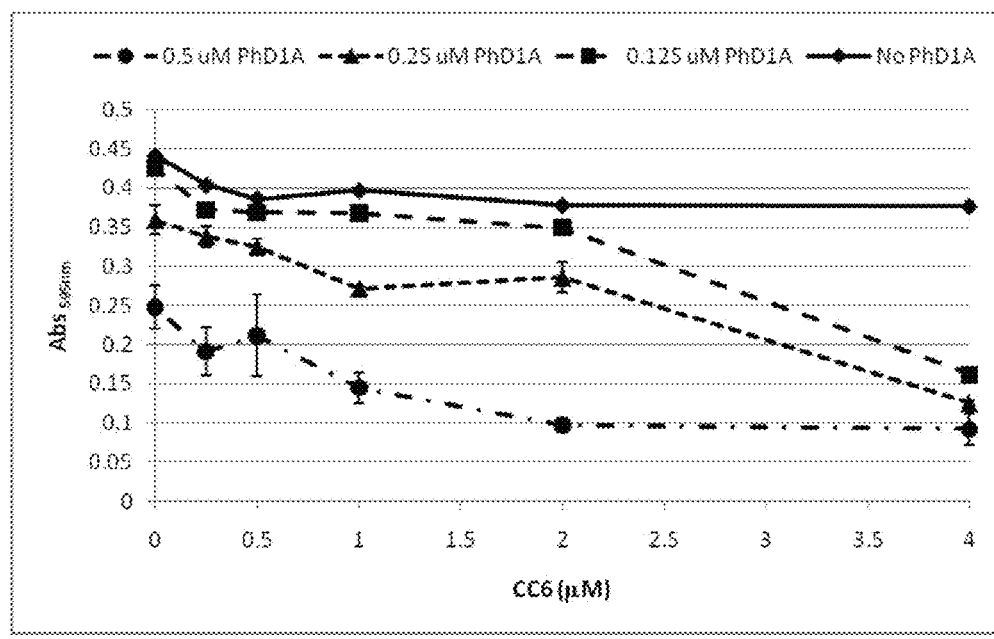
Figure 5H:
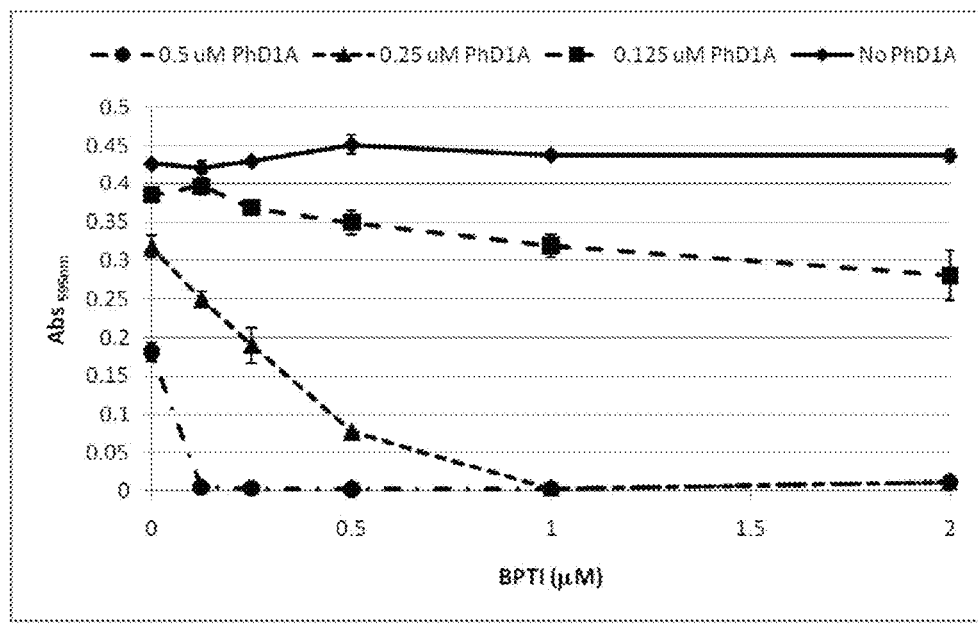
Figure 5I:
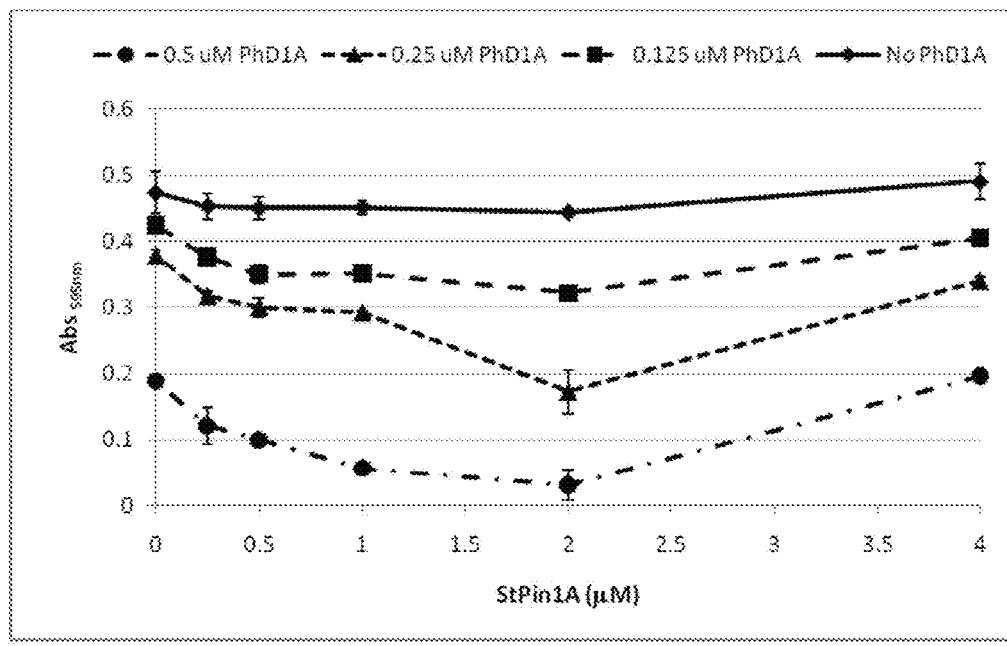

An alignment of the amino acid sequences of NaD1, Tomdef2 and PhD1A is shown in FIG. 5A. Overall they share about 60% sequence identity (FIG. 5A). The tomato and petunia defensins had a synergistic effect on the inhibitory activity of the *Nicotiana alata* cystatin NaCys2 (10.8 kDa) (FIGS. 5B, 5F) and the maize cystatin CC6 (FIGS. 5C, 5G) as well as on the inhibitory activity of Bovine Trypsin Inhibitor type I-P (6.5 kDa) (FIG. 5D, 5H) and the Type 1 proteinase inhibitor StPin1A (FIG. 5E, 5I) None of these proteinase inhibitors had any fungicidal activity when they were not combined with a defensin.

Synergy calculations are presented in FIGS. 5J and 5K wherein Ee is the expected effect from the additive response according to Limpel's formula (Richer, 1987) expressed as percent inhibition and Io is the percent inhibition observed. Synergy, that is Io values higher than Eo values, was obtained with NaD1 and all four proteinase inhibitors Numbers are marked with an asterisk where synergy was obtained.

Example 6

Inhibition of the Growth of *Fusarium oxysporum* in the Presence of NaD1 and Cysteine and Serine Proteinase Inhibitors In Vitro The inhibitory effects of defensin (NaD1) and proteinase inhibitors on the growth of *Fusarium oxysporum* f. sp. *vasinfectum* (Fov) (Australian isolate VCG01111 isolated from cotton and provided by Farming Systems Institute, DPI, Queensland, Australia) were measured essentially as described by Broekaert et al, supra 1990. Spores were isolated from sporulating cultures growing in ½ strength potato dextrose broth (PDB). The Fov culture was grown in ½ PDB for 1-2 weeks at room temperature, before spores were separated from hyphal matter by filtration through sterile tissue paper. The concentration of spores in the filtrate was measured using a hemocytometer. NaD1 and the proteinase inhibitors were prepared as described in Example 4. The conditions used for the fungal growth assay were the same as those described in Example 4. After 40h at 25° C. fungal growth was assessed by measuring optical density at 595 nm (A595).

Results

In assays with *F. oxysporum*, synergy between NaD1 and proteinase inhibitors was most obvious when NaD1 was combined with Bovine Trypsin Inhibitor type I-P (6.5 kDa) (FIG. 6). Less, but significant synergy was obtained with combinations of NaD1 and either the *N. alata* cystatin NaCys2 or the StPin1A inhibitor. Synergy was not apparent with the cysteine proteinase inhibitor CC6 (FIG. 6). Synergy calculations are presented in FIG. 6 wherein Ee is the expected effect from the additive response according to Limpel's formula (Richer, 1987) expressed as percent inhibition and Io is the percent inhibition observed. Numbers are marked with an asterisk where synergy was obtained.

Example 7

Inhibition of *Fusarium oxysporum* f. Sp. *Vasinfectum* (Fov) Infection in Transgenic Cotton Seedlings Expressing NaD1 and NaCys2

Gene constructs are produced that encode both the NaD1 defensin and a proteinase inhibitor under control of a plant promoter such as CaMV35S and a plant terminator such as the nos terminator. The gene construct is ligated into a binary vector such as pBin19 with a kanamycin selectable marker and is delivered into cotton (*Gossypium hirsutum*, cultivar 315) via *Agrobacterium* mediated transformation. Transgenic plants are screened for the expression of NaD1 and proteinase inhibitors by ELISA using antibodies such as those described in Examples 1 and 2.

Glasshouse bioassay of transgenic and non-transgenic cotton seed in *Fusarium oxysporum* f. sp. vasinfectum infected soil.

A glasshouse bioassay with infected soil is used to assess the level of resistance to Fov in non-transgenic Coker 315 and transgenic Coker 315 expressing NaD1 and a proteinase inhibitor. Cultures of Fov (isolate #24500 VCG 01111) are prepared in millet and incorporated into a soil mix. The infected soil is used to grow transgenic lines and non-transgenic Coker 315. The culture of Fov is prepared in ½ strength PDB (12 g/L potato dextrose) and grown for approximately one week at 26° C. The culture (5 to 10 mL) is used to infect autoclaved hulled millet which is then grown for 2 to 3 weeks at room temperature. The infected millet is incorporated into a pasteurized peat based soil mix at 1% (v/v), by vigorous mixing in a 200 L compost tumbler. The infected soil is transferred to plastic containers (10 L of mix per 13.5 L container).

Forty eight seeds are planted for each test. Seed is sown directly into the containers, 12 seed per box in a 3×4 array. Three seed for each test are sown randomly in each box.

Plants are grown for 7 weeks. Foliar symptom development is measured throughout the trial and disease score is determined by destructive sampling at the end of the trial. The following rating is used to determine the disease score: 0=no symptoms, 1=vascular browning to base of stem, 2=vascular browning to cotyledons, 3=vascular browning past cotyledons, 4=vascular browning to true leaves, 5=dead. The average disease score is an average for all seeds that germinate.

Example 8

Inhibition of the Growth of *Colletotrichum graminicola* in the Presence of NaD1 and Serine or Cysteine Proteinase Inhibitors In Vitro The inhibitory effects of defensin (NaD1) and serine or cysteine proteinase inhibitors were assayed on growth of *Colletotrichum graminicola* (maize isolate).

Spores of *C. graminicola* were isolated from sporulating cultures growing on the same medium and under the same conditions as used for *Fusarium graminearum* in Example 4. Preparation of NaD1 and the proteinase inhibitors, and the conditions used for the fungal growth assay were also the same as outlined in Example 4. After 40 h at 25° C. fungal growth was assessed by measuring optical density at 595 nm (A595).

Results

Figure 7A:
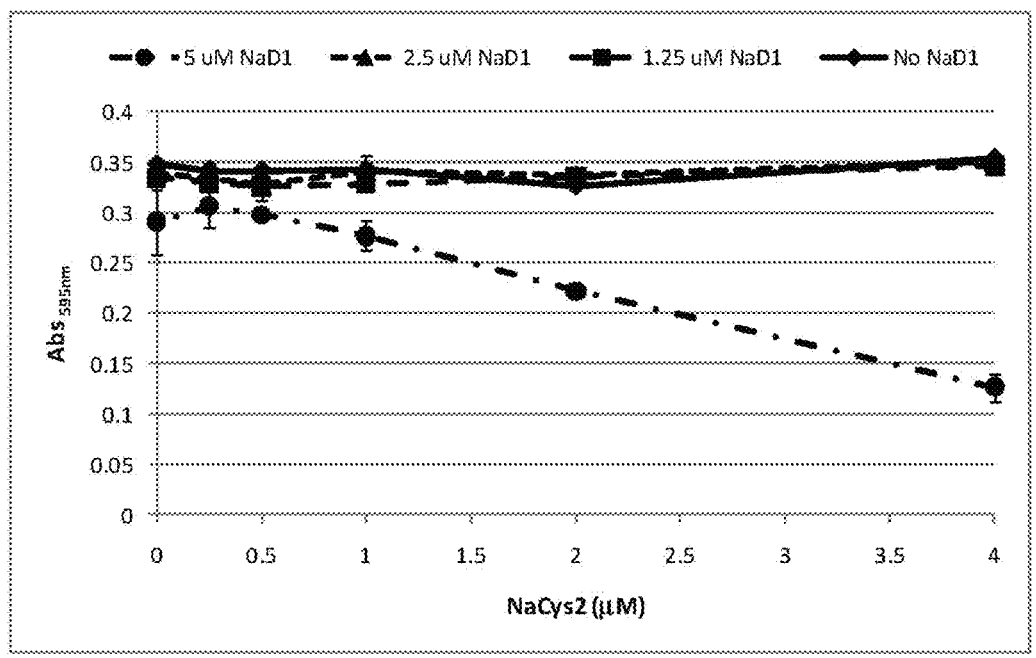
Figure 7B:
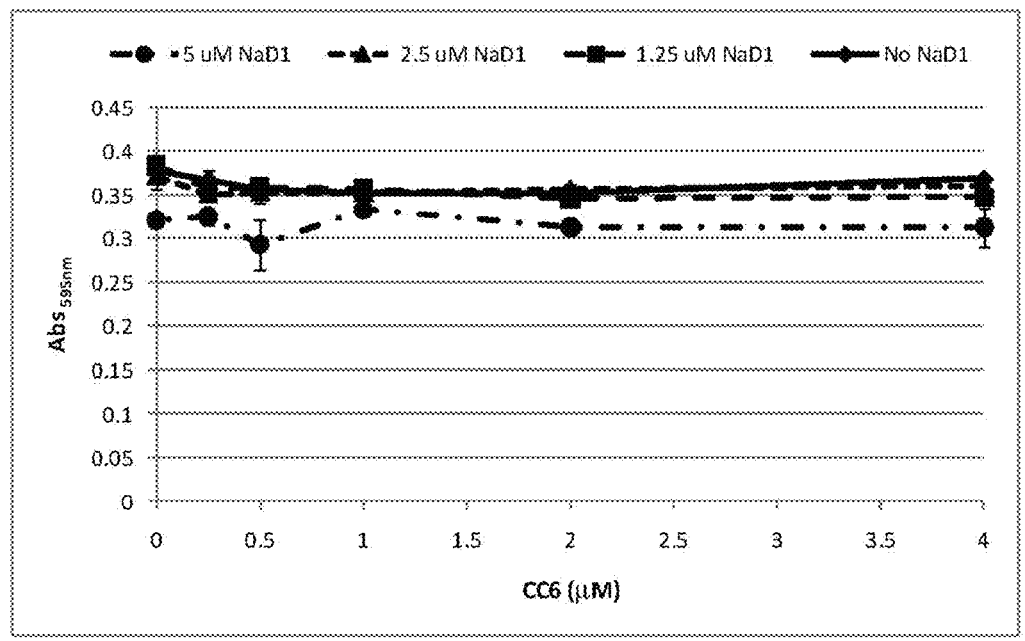
Figure 7C:
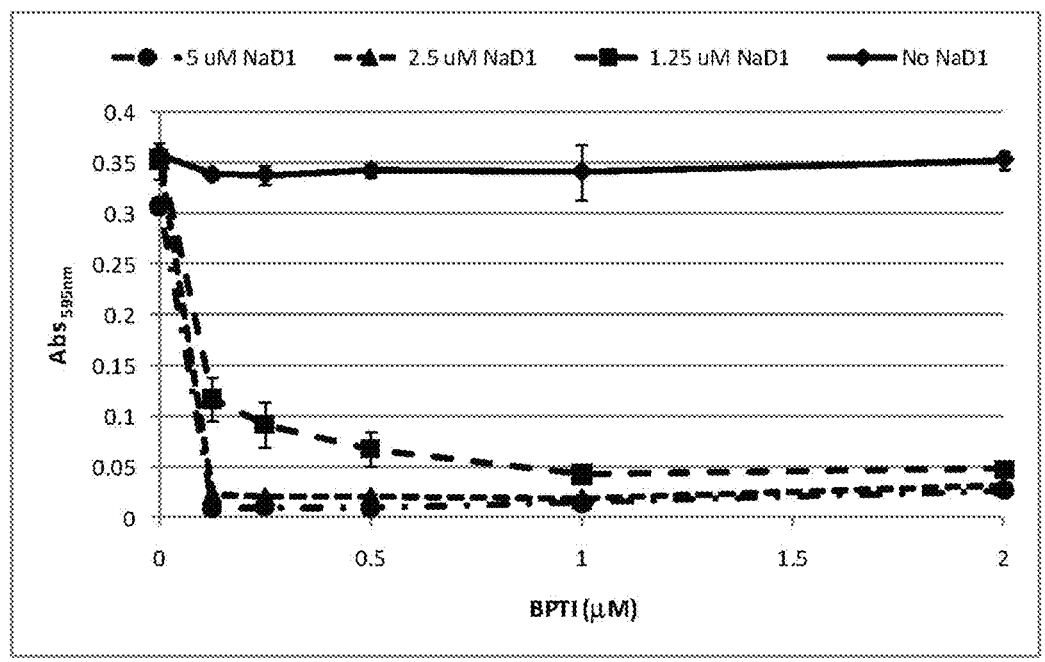
Figure 7D:
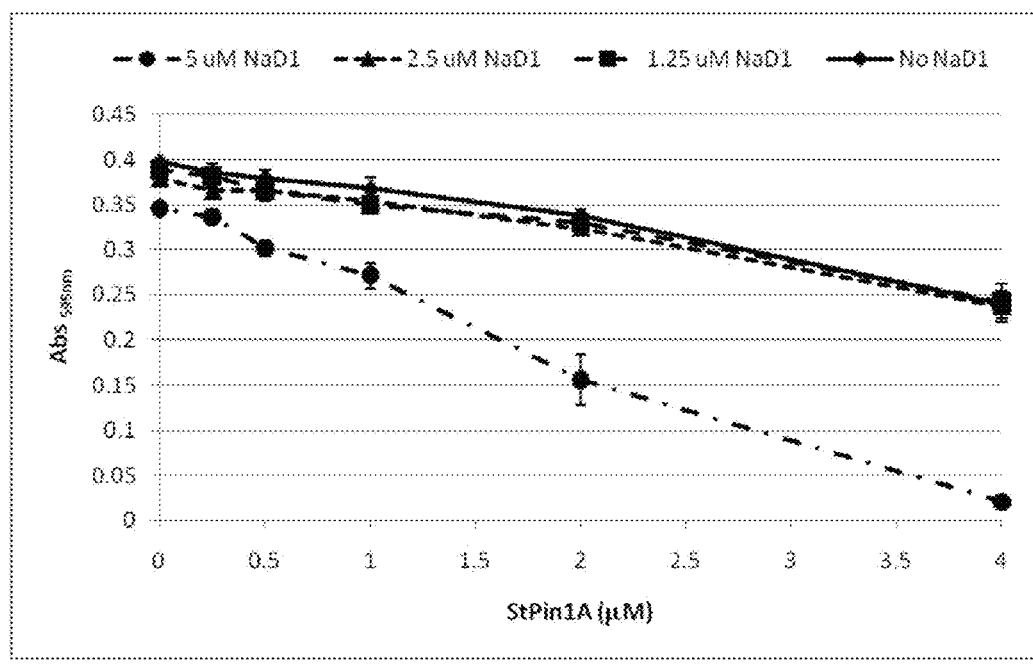
Figure 8A:
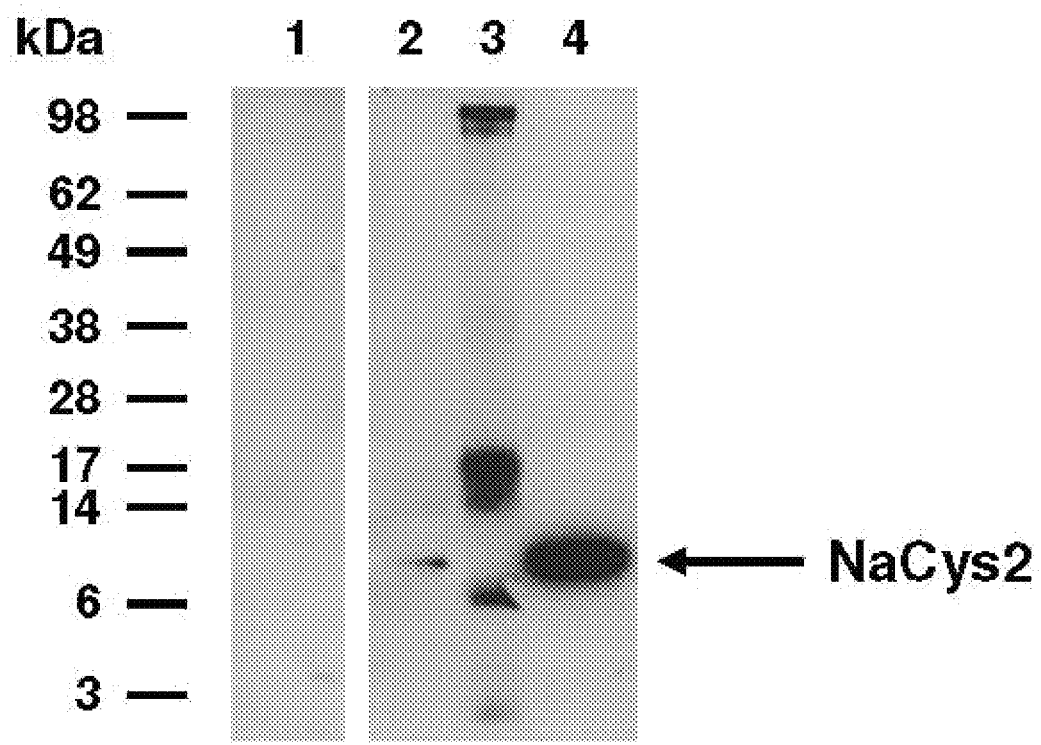
FIG. 8A is a protein blot of extracts prepared from cotton cotyledons after transient expression with pHEX116. The blot was probed with antibody raised against NaCys1 (SEQ ID NO:2). Lane 1: cotyledon sample transfected with empty pBIN19 vector, lane 2: cotyledon sample transfected with pHEX116, lane 3: SeeBlue Plus2 standards, lane 4: 20 ng recombinant HPLC purified NaCys2 (SEQ ID NO:4). The 10.9 kDa NaCys2 peptide (arrowed) was present in the cotyledon sample transfected with pHEX112.
Figure 8B:
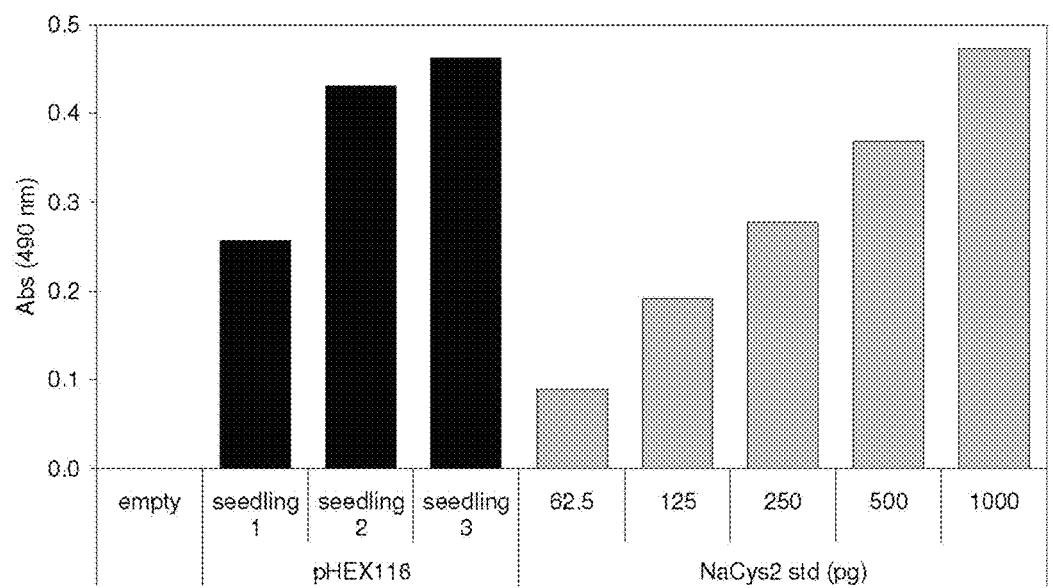
FIG. 8B is a bar graph illustrating NaCys2 detected by ELISA in extracts from cotton cotyledons after transient expression with pHEX116 or pBIN19 empty vector. Samples were diluted 1:20.

NaD1 defensin has a synergistic effect on the inhibitory activity of the *N. alata* cystatin NaCys2 (FIG. 7A). Higher or better synergy was obtained with the serine proteinase inhibitor StPin1A (FIG. 7D) and particularly the Bovine pancreatic trypsin inhibitor type I-P (FIG. 7C). Under the conditions used no obvious synergy was apparent with the maize cystatin CC6 (FIG. 7B). Synergy calculations are presented in FIG. 7E where Ee is the expected effect from the additive response according to Limpel's formula (Richer, 1987) expressed as percent inhibition and Io is the percent inhibition observed. Numbers are marked with an asterisk where was larger than Ee which is a measure of synergy.

Example 9

Inhibition of the Growth of *Fusarium graminearum, Colletotrichum graminicola* and *Aspergillus niger* in the Presence of NaD1 and Serine Proteinase Inhibitors In Vitro Recombinant CI-1B, CI-2, NaPin1A and NaPin1B were prepared as 10 times stock solutions in $H_2O$. The type-II trypsin inhibitor from *Phaseolus limensis* (lima bean, LBTI), the Kunitz trypsin inhibitor from *Glycine max* (soybean, SBTI) and the Bowman-Birk inhibitor from *Glycine max* (BBTI) were purchased from Sigma (product numbers T9378, T9003 and T9777 respectively) and diluted to 10 times stock solutions in $H_2O$.

The inhibitory effects of NaD1 in combination with serine proteinase inhibitors on the growth of *Fusarium graminearum, Colletotrichum gramincola* or *Aspergillus niger* was measured essentially as described by Broekaert et al, supra 1990. Spores were isolated from sporulating cultures growing on synthetic nutrient poor agar (SNPB, *Fusarium graminearum*) or V8 agar (*Colletotrichum graminicola, Aspergillus niger*) and counted using a hemocytometer.

Antifungal assays were conducted in 96 well microtiter trays essentially as described in the detailed description (analysis of antifungal activity). Wells were loaded with 10 μL of filter sterilized (0.22 μm syringe filter, Millipore) NaD1 (2.5 μM for *Fusarium graminearum*, 25 μM for *Colletotrichum graminicola* and *Aspergillus niger*), or water, along with 10 μL of filter sterilized (0.22 μm syringe filter, Millipore) proteinase inhibitor or water and 80 μL $5 \times 10^4$ spores/mL in ½ strength PDB. The plates were incubated at 25° C. Fungal growth was assayed by measuring optical density at 595 nm ($A_{595}$) using a microtitre plate reader (SpectraMax Pro M2; Molecular Devices). Each test was performed in quadruplicate.

Results

NaD1 was synergistic with CI-1B, CI-2, LBTI and SBTI against *Fusarium graminearum* and with CI-1B, CI-2, LBTI, NaPin1A, NaPin1B and BBTI against *Colletotrichum graminicola*. NaD1 was also synergistic with CI-1B against *Aspergillus niger*. Synergy calculations are presented in FIG. 9 wherein Ee is the expected effect from the additive response according to Limpel's formula (Richer, 1987) expressed as percent inhibition and Io is the percent inhibition observed. Numbers are marked with an asterisk where synergy was obtained.

Example 10

Synergy of Class I Permeabilising Defensins with Serine and Cysteine Protease Inhibitors Against *Fusarium graminearum, Colletotrichum graminicola*

Recombinant At2g38870 and HvCPI6 were prepared as 10 times stock solutions in $H_2O$. Bovine pancreatic trypsin inhibitor (BPTI) was purchased from Sigma (product numbers T0256) and diluted to a 10 times stock solution in $H_2O$.

DNA encoding the defensins HXL001, HXL002, HXL004, HXL007, HXL008 and DmAMP1 (FIG. 10A) was ordered from Genscript. Inserts were excised from the pUC57 vector using KpnI and XhoI, extracted from agarose gels using the Perfectprep kit (Eppendorf) and ligated into pPINK which was then used to transform TOP10 *E. coli* cells. Plasmid DNA was isolated and linearized using AflII then used to transform PichiaPink (Trademark) cells. The PichiaPink (Trademark) expression system is well-known and commercially available from Invitrogen (Carlsbad, Calif.; see the supplier's PichiaPink (Trademark) Expression Manual disclosing the sequence of the pPINK expression vector).

A single pPINK-defensin *P. pastoris* PichiaPink (Trademark) strain 1 colony was used to inoculate 25 mL of BMG medium (described in the Invitrogen *Pichia* Expression Manual) in a 250 mL flask and that was incubated over for 2-3 days in a 30° C. shaking incubator (140 rpm). The culture was used to inoculate 200 mL of BMG in a 1 L baffled flask which was placed in a 30° C. shaking incubator (140 rpm) overnight. The cells were harvested by centrifugation (2,500×g, 10 min, 4° C.) and resuspended into 1 L of BMM medium in a 5 L baffled flask and incubated in a 28° C. shaking incubator for 3 days. The cultures were induced at t=24 hours and 48 hours. The expression medium was separated from cells by centrifugation (6000 rpm, 20 min). The medium was adjusted to pH 3.0 before it was applied to an SP Sepharose column (1 cm×1 cm, Amersham Biosciences) pre-equilibrated with 100 mM potassium phosphate buffer, pH 6.0. The column was then washed with 100 mL of 100 mM potassium phosphate buffer, pH 6.0 and bound protein was eluted in 10×10 mL of 100 mM potassium phosphate buffer containing 500 mM NaCl. Eluted proteins were concentrated down to 1 mL using a centrifugal column and washed 5× using sterile milli Q ultrapure water. The protein concentration of *Pichia*-expressed NaD1 was determined using the bicinchoninic acid (BCA) protein assay (Pierce Chemical Co.) with bovine serum albumin (BSA) as the protein standard.

The inhibitory effects of defensins in combination with proteinase inhibitors on the growth of *Colletotrichum gramincola*, or *Fusarium graminearum* was measured essentially as described by Broekaert et al, supra 1990. Spores were isolated from sporulating cultures growing on synthetic nutrient poor agar (SNPB, *Fusarium graminearum*) or V8 agar (*Colletotrichum graminicola*) and counted using a hemocytometer.

Antifungal assays were conducted in 96 well microtiter trays essentially as described in the detailed description (analysis of antifungal activity). Wells were loaded with 10 μL of filter sterilized (0.22 μm syringe filter, Millipore) defensin or water, along with 10 μL of filter sterilized (0.22 μm syringe filter, Millipore) proteinase inhibitor or water and 80 μL $5 \times 10^4$ spores/mL in ½ strength PDB. The plates were incubated at 25° C. Fungal growth was assayed by measuring optical density at 595 nm ($A_{595}$) using a microtitre plate reader (SpectraMax Pro M2; Molecular Devices). Each test was performed in quadruplicate.

The ability of defensins to permeabilise *Fusarium oxysporum* f. sp. *vasinfectum* (Fov) hyphae was assessed using a SYTOX green assay as described in the detailed description (NaD1 and membrane permeabilisation).

Results

The defensins NaD1, HXP4, HXL002, HXL007 and HXL008 efficiently permeabilise Fov hyphae within 60 mins (FIG. 10B). The defensins HXL004 and DmAMP1 do not permeabilise Fov hyphae, even after 2 h.

Figure 10C:
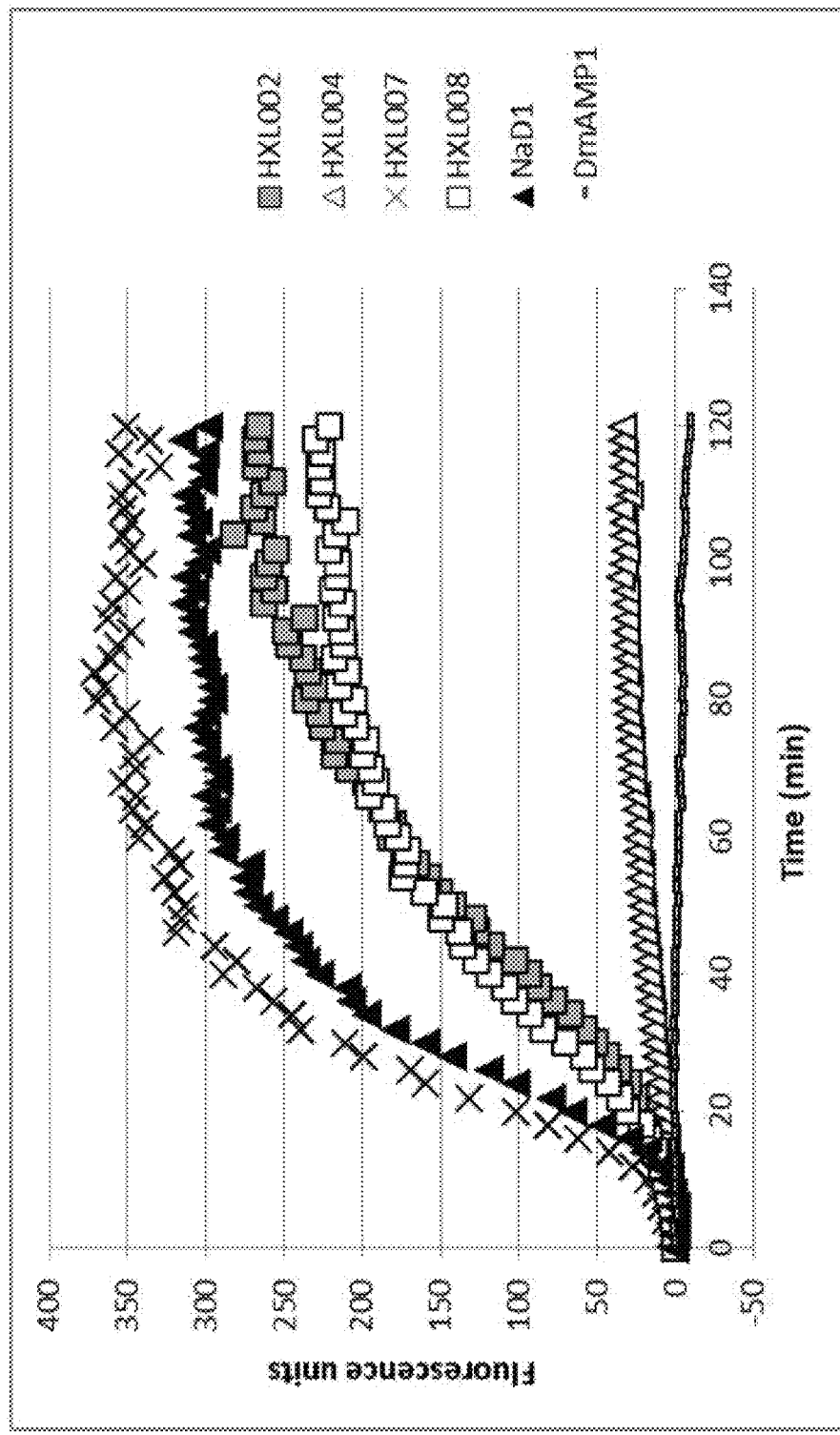
FIG. 10C is a graphical representation showing permeabilisation of the plasma membrane of *Fusarium oxysporum* hyphae in the presence of various defensins. Membrane permeabilisation was measured by monitoring the change in the SYTOX green fluorescence over 2 h.

Results of the synergy assays of defensins with proteinase inhibitors are presented in FIGS. 10C and 10D. The defensins HXL001, HXL002, HXL007 and HXL008 are synergistic with At2g38870, HvCPI6 and BPTI against *Colletotrichum graminicola*. Against *Fusarium graminearum*, HXL002, is synergistic with BPTI, HXL008 is synergistic with BPTI and HvCPI6 and HXL007 is synergistic with BPTI, HvCPI6 and At2g38870. DmAMP1 does not show significant synergy with any of the proteinase inhibitors tested. Synergy calculations are presented in Table 1 wherein Ee is the expected effect from the additive response according to Limpel's formula (Richer, 1987) expressed as percent inhibition and Io is the percent inhibition observed. Numbers are marked with an asterisk where synergy was obtained.

Example 11

Inhibition of *Leptosphaeria maculans* Infections in the Presence of NaD1 and Serine or Cysteine Proteinase Inhibitors In Vitro The inhibitory effects of defensin (NaD1) in combination with serine or cysteine proteinase inhibitors on the growth of *Leptosphaeria* maculans (Australian isolate IBCN18, Prof. B. Howlett) are measured essentially as described by Broekaert et al, 1990. *Leptosphaeria* maculans is grown in 10% (v/v) V8 medium for about 2 weeks. Spores are collected by filtration through sterile muslin and adjusted to a final concentration of 5×10$^4$ spores/mL. The conditions used for the fungal growth assay are the same as those described in Example 4 except 10% (v/v) V8 medium is used.

NaD1 and proteinase inhibitors are prepared as described in Example 4. Antifungal assays are conducted in 96 well microtiter trays essentially as described in the detailed description (analysis of antifungal activity). Wells are loaded with 10 μL of filter sterilized (0.22 μm syringe filter, Millipore) NaD1 (10× stock for each final concentration) or water, 10 μL of filter sterilized (0.22 μm syringe filter, Millipore) proteinase inhibitor (10× stock for each final concentration) or water and 80 μL 5×104 spores/mL in ½ strength PDB. The plates are incubated at 25° C. Fungal growth is assayed by measuring optical density at 595 nm (A595) using a microtitre plate reader (SpectraMax Pro M2; Molecular Devices). Each test is performed in quadruplicate.

Example 12

Inhibition of *Leptosphaeria Maculans* Infections in Transgenic Canola Seedlings Expressing NaD1 and NaCys2

Construction of NaCys2 Binary Vector (pHEX116)

DNA encoding *Nicotiana alata* cystatin 2 (NaCys2, SEQ ID NO:4) was excised from a pCR2.1-TOPO plasmid containing NaCys2 using BamH I and Sal I and cloned into pAM9 which contains the 35S CaMV promoter and terminator (pAM9 was modified from pDHA, Tabe et al., Journal of Animal Science, 73: 2752-2759, 1995). EcoRI was then used to excise the plant transcription unit which was cloned into the pBIN19 binary vector to produce pHEX116. This vector was then introduced into *Agrobacterium tumefaciens* LBA4404.

Transient Expression of NaCys2 in Cotton Cotyledons

*Agrobacterium tumefaciens* containing pHEX116 was spread on a selective plate and grown in the dark at 30° C. for 3 days. Bacteria were then resuspended to an OD600 of 1.0 in infiltration buffer (10 mM magnesium chloride and 10 uM acetosyringone (0.1 M stock in DMSO)) and incubated at room temperature for 2 h. Cotton plants (cv Coker 315) were grown for 8 days in a controlled temperature growth cabinet (25° C., 16 h/8 h light/dark cycle). The underside of cotyledons was infiltrated by gently pressing a 1 mL syringe against the leaf and filling the leaf cavity with the *Agrobacterium* suspension. The area of infiltration (indicated by darkening) was noted on the topside of the leaf. Plants were grown for a further 4 days. The infiltrated areas were then excised, weighed and frozen in liquid nitrogen. Protein expression was determined by ELISA and immunoblots. NaCys2 was detected by immunoblot (FIG. 8A) and ELISA (FIG. 8B) in cotton cotyledons transfected with pHEX116.

Detection of NaCys2 in Transgenic Plant Tissue

Immunoblot Analysis

Tissue (100 mg) was frozen in liquid nitrogen and ground to a fine powder in a mixer mill (Retsch MM300), for 2×15 sec at frequency 30. The powder was added to 1 ml acetone, vortexed thoroughly and centrifuged at 14,000 rpm (18,000g) for 2 min and the supernatant discarded. The air dried pellet was resuspended in 120 μl of PBS/0.05% (v/v) Tween® 20 with 3% (w/v) PVPP by vortexing thoroughly and supernatant was collected after centrifugation at 14,000 rpm for 10 min. For analysis by SDS-PAGE, 30 μl of sample in 1× sample buffer (Novex NuPAGE LDS sample buffer) and 5% v/v β-mercaptoethanol was used.

Extracted proteins were separated by SDS-PAGE on preformed 4-12% w/v polyacrylamide gradient gels (Novex, NuPAGE bis-tris, MES buffer) for 35 min at 200V in a Novex X Cell mini-cell electrophoresis apparatus. Prestained molecular size markers (Novex SeeBlue Plus 2) were included as a standard. Proteins were transferred to a nitrocellulose membrane (Osmonics 0.22 micron NitroBind) using the Novex X Cell mini-cell electrophoresis apparatus for 60 min at 30V with NuPAGE transfer buffer containing 10% v/v methanol. After transfer, membranes were dipped in isopropanol for 1 min, followed by a 5 min wash in TBS.

The membrane was blocked for 1 h in 3% w/v BSA at RT followed by incubation with primary antibody overnight at RT (NaCys1 antibody: 1:2500 dilution of a 1 mg/ml stock in TBS/1% BSA). The membrane was washed 5×10 min in TBST before incubation with goat anti-rabbit IgG conjugated to horseradish peroxidase for 60 min at RT (Pierce, 1:100,000 dilution in TBS). Five further 10 min TBST washes were performed before the membrane was incubated with the SuperSignal West Pico Chemiluminescent substrate (Pierce) according to the Manufacturer's instructions. Membranes were exposed to ECL Hyperfilm (Amersham).

Elisa

ELISA plates (Nunc Maxisorp™ (In Vitro, Noble Park VIC 3174) #442404) were coated with 100 μL/well of primary antibody in PBS (150 ng/well protein A purified polyclonal rabbit antibody raised in response to recombinantly expressed NaCys1 (SEQ ID NO:2) by a standard method and incubated overnight at 4° C. in a humid box. The next day, the plates were washed with PBS/0.05% (v/v) Tween® 20 for 2 min×4. Plates were then blocked with 200 μL/well 3% (w/v) BSA (Sigma (Castle Hill, NSW Australia 1765) A-7030: 98% ELISA grade) in PBS and incubated for 2 h at 25° C. and then washed with PBS/0.05% (v/v) Tween® 20, 2 min×4.

For preparation of samples, 100 mg of frozen canola leaf or cotton cotyledon tissue was ground in liquid nitrogen using a mixer mill for 2×10 sec at frequency 30. One mL of 2% (w/v) insoluble PVPP (Polyclar)/PBS/0.05% (v/v) Tween® 20 was added to each sample and the mixture vortexed, centrifuged for 10 min and the supernatant collected. Dilutions of the protein extracts were prepared in PBS/0.05% (v/v) Tween® 20, applied to each well (100 μL/well) and incubated for 2 h at 25° C.

Plates were washed (2 min×4) with PBS/0.05% (v/v) Tween® 20. Secondary antibody in PBS (150 ng/well biotin-labelled anti-NaCys1) was applied to each well at 100

μL/well and incubated for 1 h at 25° C. Plates were then washed (2 min×4) with PBS/0.05% (v/v) Tween® 20. Following this, NeutriAvidin HRP-conjugate (Pierce, Rockford, II 61105) #31001; 1:1000 dilution; 0.1 μL/well) in PBS was applied to each well at 100 μL/well. After a 1 h incubation at 25° C. the plates were washed (2 min×4) with PBS/0.05% Tween® 20, followed by two 2 min washes with $H_2O$. Fresh substrate was prepared by dissolving one ImmunoPure OPD (peroxidase substrate) tablet (Pierce, Rockford, II 61105 #34006) in 9 mL water, then adding 1 mL of stable peroxide buffer (10×, Pierce, Rockford, II 61105 #34062). Substrate (100 μL/well) was added to each well and incubated at 25° C. The reaction was stopped with 50 μL of 2.5 M sulfuric acid and the absorbance was measured at 490 nm in a plate reader.

Production of Transgenic Canola Expressing NaCys2 and NaD1

Transgenic canola (Brassica napus, cv R164) expressing NaCys2 is produced by Agrobacterium tumefaciens mediated transformation. The DNA binary vector (pHEX116) used for the transformation is described above. The binary vector is transferred into Agrobacterium tumefaciens strain AGL 1 by electroporation and the presence of the plasmid confirmed by gel electrophoresis. Cultures of Agrobacterium are used to infect hypocotyl sections of canola cv R164. Transgenic shoots are selected on the antibiotic kanamycin at 25 mg/L. Transgenic plants expressing NaD1 and cystatin are selected using ELISA's and/or immunoblots to detect soluble proteins extracted from leaves.

Glasshouse Bioassays with Leptosphaeria maculans

The pathogen Leptosphaeria maculans (Australian isolate ICBN18) is grown on 10% (v/v) V8 agar plates for 1-2 weeks at room temperature. Pycnidiospores are isolated by covering the plate with sterilized water (5 mL) and scraping the surface of the agar to dislodge the spores. Spores are separated from the hyphal matter by filtration through sterile tissues (eg Kleenex). The concentration of the spores in the filtrate is measured using a haemocytometer and the final concentration is adjusted to $10^6$ pycnidiospores/mL with water.

Seedlings (30 seeds per test) are grown in the glasshouse in small planting trays at 22° C. Ten days after sowing, the two cotyledons of each seedling are punctured twice with a 26 gauge needle (once in each of the 2 lobes) and the wounded area is inoculated with a droplet of spores (5 μL, $10^6$ spores/mL). Controls are inoculated with water. The plants are maintained under high humidity conditions for 3 days to facilitate spore germination.

Disease symptoms are assessed at 10, 14 and 17 days after inoculation. The diameter of each lesion is measured and the disease scored based on a system described by Williams and Delwiche (1979). Wounds with no darkening are scored as 0, lesions of diameter 0.5-1.5 mm are scored as 1, lesions of diameter 1.5-3.0 mm are scored as 3, lesions of diameter 3.0-6.0 are scored as 5, lesions greater than 6 mm in diameter or which have complete cotyledon necrosis are scored as 7. The disease scores are statistically analyzed by ordinal regression. Lesion size is quantified using computer software analysis (ImageJ) of digital images in $mm^2$. The average lesion size data is statistically analyzed by transforming the data (log 10) and performing the t-test.

To test for synergy between NaD1 and NaCys2, the transgenic line CAT13.26 which expresses NaD1 is crossed with a transgenic canola line expressing NaCys2. Line CAT13.26 is described in U.S. patent application Ser. No. 12/362,657, incorporated herein by reference. The three lines (NaD1 expressing, NaCys2 expressing and NaD1 and NaCys2 expressing) are then assessed in the seedling bioassay described above.

Those skilled in the art will appreciate that the compositions and methods described herein are susceptible to variations and modifications other than those specifically described. It is to be understood that the claimed invention includes all such variations and modifications. The invention also includes all of the steps, features, compositions and compounds referred to or indicated in this specification, individually or collectively, and any and all combinations of any two or more of said steps or features.

BIBLIOGRAPHY

Abraham et al, J Exp Bot 57:4245-55
Alexander et al, Proc Natl Acad Sci USA 90:7327-7331, 1993
Almeida et al, Arch Biochem Biophys 378.278-286, 2000
Anderson and Kingston, Proc Natl Acad Sci USA 80.6838-6842, 1983
Baker et al, Methods in Enzymology 398:540-554, 2005
Balandin et al, Plant Mol Biol 58269-282, 2005
Bevan et al, Nucleic Acids Res 11(2).269-385, 1983
Bjork et al, Biochemistry, 35, 10720-10726, 1996
Broekaert et al, FEMS Microbiol Lett 69:55-59, 1990
Cantanzariti et al, Protein Science 13:1331-1339, 2004
Chen et al, J Agric Food Chem 53.982-988, 2005
De Samblanx et al, J Biol Chem 272:1171-1179, 1997
Ekengren and Hultmark, Insect Biochem Mol Biol 29.965-972, 1999
Epand et al, Biochim Biophys Acta 1758:1343-1350, 2006
Gorlach et al, Plant Cell 8:629-643, 1996
Greco et al, Pharmacol Rev 47.231-385. 1995
Hanks et al, Plant Mol Biol 58.285-399. 2005
Harrison et al, Aust J Plant Phys 24:571-578. 1997
Herrera-Estrella et al, EMBO J 2987-995. 1983
Joshi et al, Biochem. Biophys. Res Comm. 246:382-387. 1998
Kim et al, Eur J Biochem 268:4449-4458, 2001
Klee et al, Bio/Technology 3:637-642, 1985
Klis et al, FEMS Microbiol Rev 26239-256. 2002
Kragh et al, Mol Plant Microbe Interact 8:424-434, 1995
Ladokhin and White, Biochim Biophys Acta 1514253-260, 2001
Lay et al, Curr Protein Pept Sci 6:85-101, 2005
Lay et al, Plant Physiol 131:1283-1293, 2003
Lee et al., Nature Structure Biology 6:526-530, 1999
Leiter et al, Antimicrob Agents Chemother 49.2445-2453, 2005
Lin et al, Proteins 68:530-540, 2007
Lobo et al, Biochemistry 46:987-996, 2007
Martinez et al, Molecular Plant-Microbe Interactions, 16:876-883, 2003
Massonneau et al, Biochim Biophys Acta 1729:186-199, 2005
Matsuzaki et al, Biochemistry 343423-3429. 1995
Matsuzaki Biochim Biophys Acta 1462:1-10. 1999
Melo et al, Analytical Biochemistry 293:71-77, 2001
Meyer et al, Plant Physiol 112.615-622, 1996
Nilsson et al, Cell 58:707, 1989
Oberparleiter et al, Antimicrob Agents Chemother 47:3598-3601, 2003
Oerke and Dehne, Crop Protection 23.275-285, 2004
Osborn et al, FEBS Lett 368:257-262, 1995
Park et al, Plant Mol Biol 50: 59-69, 2002
Pervieux et al, Physiol Mol Plant Pathol 64:331-341, 2004

Ramamoorthy et al, *Molecular Microbiology* 66:771-786, 2007
Richer, *Pestic Sci* 19:309-315, 1987
Rogers et al, *Methods for Plant Molecular Biology*, 1988
Saitoh, *Mol Plant Microbe Interact* 14:111-115, 2001
Salzman et al, *Mol Plant Microbe Interact* 17:780-788, 2004
Schilperoort et al, *European Patent Office Publication* 120, 516
Segura et al, *FEBS Lett* 435:159-162, 1998
Terras et al, *J Biol Chem* 267:15301-15309, 1992
Theis et al, *Antimicrob Agents Chemother* 47:588-593, 2003
Theis et al, *Res Microbiol* 156: 47-56, 2005
Thevissen et al, *Proc Natl Acad Sci USA* 97.9531-9536, 2000
Thevissen et al, *J Biol Chem* 2793900-3905, 2004
Thevissen et al, *Curr Drug Targets* 6.923-928, 2005
Turk and Bode, *FEBS Lett.* 285213-219, 1991
Uknes, *Molecular Plant Microbe Interactions* 6.680-685, 1993
Urdangarin and de la Canal, *Plant Physiol Biochem* 38253-258, 2000

---

The invention claimed is:

1. A method of inhibiting fungal infestation on a plant, comprising contacting the plant or seed of the plant with a topical anti-fungal composition wherein the topical anti-fungal composition comprises a fungus-permeabilizing plant defensin and a proteinase inhibitor, wherein the plant defensin is PhD2 and the proteinase inhibitor is a cystatin selected from the group consisting of NaCys1, NaCys2, NaCys3, NaCys4, Hv-CP16 and CC6, and wherein the extent of fungal inhibition provided by the defensin and the proteinase inhibitor combined is greater compared to the additive inhibition provided by either the defensin or proteinase inhibitor in individual contact with the fungus at the same dose as used in a combined contact.

2. The method of claim 1, wherein the fungus is selected from the group consisting of *Fusarium graminearum, Fusarium oxysporum* f. sp. *vasinfectum* (Fov), *Colletotrichum graminicola, Leptosphaeria maculans, Alternaria brassicicola, Alternaria alternata, Aspergillus nidulans, Botrytis cinerea, Cercospora beticola, Cercospora zeae maydis, Cochliobolus heterostrophus, Exserohilum turcicum, Fusarium culmorum, Fusarium oxysporum, Fusarium oxysporum* f. sp. *dianthi, Fusarium oxysporum* f. sp. *lycopersici, Fusarium solani, Fusarium pseudograminearum, Fusarium verticilloides, Gaeumannomyces graminis var. tritici, Plasmodiophora brassicae, Sclerotinia sclerotiorum, Stenocarpella* (*Diplodia*) *maydis, Thielaviopsis basicola, Verticillium dahliae, Ustilago zeae, Puccinia sorghi, Macrophomina phaseolina, Phialophora gregata, Diaporthe phaseolorum, Cercospora sojina, Phytophthora sojae, Rhizoctonia solani, Phakopsora pachyrhizi, Alternaria macrospora, Cercospora gossypina, Phoma exigua, Puccinia schedonnardii, Puccinia cacabata, Phymatotrichopsis omnivora, Fusarium avenaceum, Alternaria brassicae, Alternaria raphani, Erysiphe graminis* (*Blumeria graminis*), *Septoria tritici, Septoria nodorum, Mycosphaerella zeae, Rhizoctonia cerealis, Ustilago tritici, Puccinia graminis, Puccinia triticina, Tilletia indica, Tilletia caries* and *Tilletia controversa.*

3. The method of claim 1, wherein the plant is a crop plant selected from the group consisting of forage, oilseed, grain, fruit, vegetable, fiber, spice, nut, turf, sugar, beverage and a forest crop.

4. The method of claim 3, wherein the crop plant is selected from the group consisting of canola, soybean, wheat, corn, cotton, alfalfa, sugarbeet, rice, potato, tomato, onion, a legume and a pea plant.

5. The method of claim 4, wherein the crop plant is cotton or corn.

6. The method of claim 1, wherein the topical anti-fungal composition is a seed coating composition.

7. The method of claim 1, wherein the fungus is selected from the group consisting of *Alternaria* spp, *Aspergillus* spp, *Botrytis* spp, *Cercospora* spp, *Cochliobolus* spp, *Colletotrichum* spp, *Diaporthe* spp, *Erysiphe* spp, *Exserohilum* spp, *Fusarium* spp, *Gaeumannomyces* spp, *Leptosphaeria* spp, *Macrophomina* spp, *Mycosphaerella* spp, *Phakopsora* spp, *Phialophora* spp, *Phoma* spp, *Phymatotrichopsis* spp, *Phytophthera* spp, *Plasmodiophora* spp, *Puccinia* spp, *Pythium* spp, *Rhizoctonia* spp, *Septoria* spp, *Sclerotinia* spp, *Stenocarpella* spp, *Thielaviopsis* spp, *Tilletia* spp, *Ustilago* spp and *Verticillium* spp.

* * * * *

SEQUENCE LISTING

```
<160> NUMBER OF SEQ ID NOS: 46

<210> SEQ ID NO 1
<211> LENGTH: 297
<212> TYPE: DNA
<213> ORGANISM: Nicotiana alata (NaCys1)

<400> SEQUENCE: 1
atggcaacac taggaggaat tcgtgaggca ggtggatctg agaacagtct tgagatcaat      60
gatcttgctc gctttgctgt tgatgaacac aacaagaaac agaatgctct tttggagttt    120
ggaaaagttg tgaatgtgaa ggaacaagtg gttgctggaa ccatgtacta cataacactg    180
gaggcaactg aaggtggtaa gagaaagca tacgaagcca aggtctgggt gaagccgtgg     240
cagaacttca agcaattgga agacttcaag cttattgggg atgccgctag tgcttaa       297

<210> SEQ ID NO 2
<211> LENGTH: 98
<212> TYPE: PRT
<213> ORGANISM: Nicotiana alata (NaCys1)

<400> SEQUENCE: 2

Met Ala Thr Leu Gly Gly Ile Arg Glu Ala Gly Gly Ser Glu Asn Ser
 1               5                  10                  15

Leu Glu Ile Asn Asp Leu Ala Arg Phe Ala Val Asp Glu His Asn Lys
            20                  25                  30

Lys Gln Asn Ala Leu Leu Glu Phe Gly Lys Val Val Asn Val Lys Glu
        35                  40                  45

Gln Val Val Ala Gly Thr Met Tyr Tyr Ile Thr Leu Glu Ala Thr Glu
    50                  55                  60

Gly Gly Lys Lys Lys Ala Tyr Glu Ala Lys Val Trp Val Lys Pro Trp
65                  70                  75                  80

Gln Asn Phe Lys Gln Leu Glu Asp Phe Lys Leu Ile Gly Asp Ala Ala
                85                  90                  95

Ser Ala

<210> SEQ ID NO 3
<211> LENGTH: 297
<212> TYPE: DNA
<213> ORGANISM: Nicotiana alata (NaCys2)

<400> SEQUENCE: 3
atggcaaatc taggaggaat tcgtgaggca ggaggatctg agaacagtct tgagatcaat      60
gatcttgctc gctttgctgt tgatggacac aacaagaaac agaatgcact tctggagttc    120
agaaaggttg tgaatgtgaa ggaacaagtg gttgctggaa ccatgtacta cataacactg    180
gaggcaactg aaggtggtaa gagaaagca tacgaagcca aggtctgggt gaagccgtgg     240
cagaacttca agcaattgga agacttcaag cttattgggg atgccactag tgcttaa       297
```

<210> SEQ ID NO 4
<211> LENGTH: 98
<212> TYPE: PRT
<213> ORGANISM: Nicotiana alata (NaCys2)

<400> SEQUENCE: 4

```
Met Ala Asn Leu Gly Gly Ile Arg Glu Ala Gly Gly Ser Glu Asn Ser
1               5                   10                  15

Leu Glu Ile Asn Asp Leu Ala Arg Phe Ala Val Asp Gly His Asn Lys
            20                  25                  30

Lys Gln Asn Ala Leu Leu Glu Phe Arg Lys Val Val Asn Val Lys Glu
        35                  40                  45

Gln Val Val Ala Gly Thr Met Tyr Tyr Ile Thr Leu Glu Ala Thr Glu
    50                  55                  60

Gly Gly Lys Lys Lys Ala Tyr Glu Ala Lys Val Trp Val Lys Pro Trp
65                  70                  75                  80

Gln Asn Phe Lys Gln Leu Glu Asp Phe Lys Leu Ile Gly Asp Ala Ala
                85                  90                  95

Ser Ala
```

<210> SEQ ID NO 5
<211> LENGTH: 297
<212> TYPE: PRT
<213> ORGANISM: Nicotiana alata (NaCys3)

<400> SEQUENCE: 5

```
Ala Thr Gly Gly Cys Ala Ala Ala Thr Cys Thr Ala Gly Gly Ala Gly
1               5                   10                  15

Gly Ala Ala Thr Thr Cys Gly Thr Gly Ala Gly Gly Cys Ala Gly Gly
            20                  25                  30

Ala Gly Gly Ala Thr Cys Thr Gly Ala Gly Ala Ala Cys Ala Gly Thr
        35                  40                  45

Cys Thr Thr Gly Ala Gly Ala Thr Cys Ala Ala Thr Gly Ala Thr Cys
    50                  55                  60

Thr Thr Gly Cys Thr Cys Gly Cys Thr Thr Thr Gly Cys Thr Gly Thr
65                  70                  75                  80

Thr Gly Ala Thr Gly Ala Ala Cys Ala Cys Ala Ala Cys Ala Ala Gly
                85                  90                  95

Ala Ala Ala Cys Ala Gly Ala Ala Thr Gly Cys Ala Cys Thr Thr Cys
            100                 105                 110

Thr Gly Gly Ala Gly Thr Thr Cys Gly Gly Ala Ala Ala Gly Gly Thr
        115                 120                 125

Thr Gly Thr Gly Ala Ala Thr Gly Thr Gly Ala Ala Gly Gly Ala Ala
    130                 135                 140

Cys Ala Ala Gly Thr Gly Gly Thr Thr Gly Cys Thr Gly Gly Ala Ala
145                 150                 155                 160

Cys Cys Ala Thr Gly Thr Ala Cys Thr Ala Cys Ala Thr Ala Ala Cys
                165                 170                 175

Ala Cys Thr Gly Gly Ala Gly Gly Cys Ala Ala Cys Thr Gly Ala Ala
            180                 185                 190

Gly Gly Thr Gly Gly Thr Ala Ala Gly Ala Ala Gly Ala Ala Ala Gly
        195                 200                 205

Cys Ala Thr Ala Cys Gly Ala Ala Gly Cys Cys Ala Ala Gly Gly Thr
    210                 215                 220
```

```
Cys Thr Gly Gly Gly Thr Ala Ala Gly Cys Gly Thr Gly
225                 230                 235                 240

Cys Ala Gly Ala Ala Cys Thr Thr Cys Ala Ala Gly Cys Ala Ala Thr
                245                 250                 255

Thr Gly Gly Ala Ala Gly Ala Cys Thr Thr Cys Ala Ala Gly Cys Thr
            260                 265                 270

Thr Ala Thr Thr Gly Gly Gly Ala Thr Gly Cys Cys Ala Cys Thr
        275                 280                 285

Ala Gly Thr Gly Cys Thr Thr Ala Ala
    290                 295
```

<210> SEQ ID NO 6
<211> LENGTH: 98
<212> TYPE: PRT
<213> ORGANISM: Nicotiana alata (NaCys3)

<400> SEQUENCE: 6

```
Met Ala Asn Leu Gly Gly Ile Arg Glu Ala Gly Gly Ser Glu Asn Ser
1               5                   10                  15

Leu Glu Ile Asn Asp Leu Ala Arg Phe Ala Val Asp Glu His Asn Lys
            20                  25                  30

Lys Gln Asn Ala Leu Leu Glu Phe Gly Lys Val Val Asn Val Lys Glu
        35                  40                  45

Gln Val Val Ala Gly Thr Met Tyr Tyr Ile Thr Leu Glu Ala Thr Glu
    50                  55                  60

Gly Gly Lys Lys Lys Ala Tyr Glu Ala Lys Val Trp Val Lys Pro Trp
65                  70                  75                  80

Gln Asn Phe Lys Gln Leu Glu Asp Phe Lys Leu Ile Gly Asp Ala Ala
                85                  90                  95

Ser Ala
```

<210> SEQ ID NO 7
<211> LENGTH: 297
<212> TYPE: DNA
<213> ORGANISM: Nicotiana alata (NaCys4)

<400> SEQUENCE: 7

```
atggcaaatc taggaggaat tcgtgaggca ggaggatctg agaacagtct tgagatcaat      60
gatcttgctc gctttgctgt tgatgaacac aacaagaaac agaatgcact tctggagttc    120
ggaaaggttg tgaatgtgaa ggaacaagtg gttgctggaa ccatgtacta cataacactg    180
gaggcaactg aaggtggtaa gaagaaagca tacgaagcca aggtctgggt gaagccgcgg    240
cagaacttca gcaattgga agacttcaag cttattgggg atgccgctag tgcttaa      297
```

<210> SEQ ID NO 8
<211> LENGTH: 98
<212> TYPE: PRT
<213> ORGANISM: Nicotiana alata (NaCys4)

<400> SEQUENCE: 8

```
Met Ala Asn Leu Gly Gly Ile Arg Glu Ala Gly Gly Ser Glu Asn Ser
1               5                   10                  15

Leu Glu Ile Asn Asp Leu Ala Arg Phe Ala Val Asp Glu His Asn Lys
            20                  25                  30

Lys Gln Asn Ala Leu Leu Glu Phe Gly Lys Val Val Asn Val Lys Glu
        35                  40                  45

Gln Val Val Ala Gly Thr Met Tyr Tyr Ile Thr Leu Glu Ala Thr Glu
```

```
            50                  55                  60
Gly Gly Lys Lys Lys Ala Tyr Glu Ala Lys Val Trp Val Lys Pro Arg
 65                  70                  75                  80

Gln Asn Phe Lys Gln Leu Glu Asp Phe Lys Leu Ile Gly Asp Ala Ala
                 85                  90                  95

Ser Ala
```

<210> SEQ ID NO 9
<211> LENGTH: 336
<212> TYPE: DNA
<213> ORGANISM: Nicotiana alata (StPin1A)

<400> SEQUENCE: 9

```
atggagtcaa agtttgctca catcattgtt ttctttcttc ttgcaacttc ctttgaaact      60
ctcatggcac gaaagaagg tgatggatca gaagtcataa aacttctaaa ggaatcggaa     120
tctgaatctt ggtgcaaagg aaaacaattc tggccagaac ttattggtgt accaacaaag     180
cttgctaagg aaataattga aggaaaat ccatccataa atgatgttcc aataatattg       240
aatggcactc cagtcccagc tgattttaga tgtaatcgag ttcgtctttt tgataacatt     300
ttgggtgatg ttgtacaaat tcctagggtg gcttaa                               336
```

<210> SEQ ID NO 10
<211> LENGTH: 75
<212> TYPE: PRT
<213> ORGANISM: Nicotiana alata (StPin1A)

<400> SEQUENCE: 10

```
Lys Glu Ser Glu Ser Glu Ser Trp Cys Lys Gly Lys Gln Phe Trp Pro
  1               5                  10                  15

Glu Leu Ile Gly Val Pro Thr Lys Leu Ala Lys Glu Ile Ile Glu Lys
                 20                  25                  30

Glu Asn Pro Ser Ile Asn Asp Val Pro Ile Ile Leu Asn Gly Thr Pro
         35                  40                  45

Val Pro Ala Asp Phe Arg Cys Asn Arg Val Arg Leu Phe Asp Asn Ile
     50                  55                  60

Leu Gly Asp Val Val Gln Ile Pro Arg Val Ala
 65                  70                  75
```

<210> SEQ ID NO 11
<211> LENGTH: 318
<212> TYPE: DNA
<213> ORGANISM: Nicotiana alata (NaD1)

<400> SEQUENCE: 11

```
atggctcgct ccttgtgctt catggcattt gctatcttgg caatgatgct ctttgttgcc      60
tatgaggtgc aagctagaga atgcaaaaca gaaagcaaca catttcctgg aatatgcatt     120
accaaaccac catgcagaaa agcttgtatc agtgagaaat ttactgatgg tcattgtagc     180
aaaatcctca gaaggtgcct atgtactaag ccatgtgtgt ttgatgagaa gatgactaaa     240
acaggagctg aaattttggc tgaggaagca aaaactttgg ctgcagcttt gcttgaagaa     300
gagataatgg ataactaa                                                    318
```

<210> SEQ ID NO 12
<211> LENGTH: 47
<212> TYPE: PRT
<213> ORGANISM: Nicotiana alata (NaD1)

<400> SEQUENCE: 12

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 13
<211> LENGTH: 375
<212> TYPE: DNA
<213> ORGANISM: Hordeum vulgare (Hv-CPI6)

<400> SEQUENCE: 13

```
atgcagaaga actcgaccat ggggagaccg ctcctcctgc tcgccctcct ggccacggcc      60
ctcgcagcca cctcggccct cggccgccgc ggcgtgcttc tgggcgggtg agccccgtc      120
aaggacgtga acgacccgca cgtccaggag ctaggcgggt gggcggtggc ccagcacgcc     180
agcctagcca aggacgggct gctcttccgc cgggtgacgc gcggcgagca gcaggtggtg     240
tccgggatga actaccgcct cttcgtggtc gcggcggacg gctccggcaa gagggtgacc     300
tatctcgcgc agatctacga gcactggagc aggacccgca agctcacgtc cttcaagccg     360
gctgccggcg gctaa                                                      375
```

<210> SEQ ID NO 14
<211> LENGTH: 102
<212> TYPE: PRT
<213> ORGANISM: Hordeum vulgare (HV-CPI6)

<400> SEQUENCE: 14

Ala Thr Ser Ala Leu Gly Arg Arg Gly Val Leu Leu Gly Gly Trp Ser
1               5                   10                  15

Pro Val Lys Asp Val Asn Asp Pro His Val Gln Glu Leu Gly Gly Trp
            20                  25                  30

Ala Val Ala Gln His Ala Ser Leu Ala Lys Asp Gly Leu Leu Phe Arg
        35                  40                  45

Arg Val Thr Arg Gly Glu Gln Gln Val Val Ser Gly Met Asn Tyr Arg
    50                  55                  60

Leu Phe Val Val Ala Ala Asp Gly Ser Gly Lys Arg Val Thr Tyr Leu
65                  70                  75                  80

Ala Gln Ile Tyr Glu His Trp Ser Arg Thr Arg Lys Leu Thr Ser Phe
                85                  90                  95

Lys Pro Ala Ala Gly Gly
            100

<210> SEQ ID NO 15
<211> LENGTH: 351
<212> TYPE: DNA
<213> ORGANISM: Zea mays (CC6)

<400> SEQUENCE: 15

```
atgtccgcga gagctcttct cctgacgacc gcgacgctgc tcctgctcgt cgccgctgcg      60
cgtgcgggc agccgctcgc cggcgggtgg agcccgatca ggaacgtcag cgacccgcac      120
atccaggagc tcggcggctg gcggtgacg gagcacgtca ggcgggccaa cgacgggctg       180
cggttcggcg aggtgacggg cggcgaggag caggtggtgt ccgggatgaa ctacaagctc      240
gtcctcgacg ccacggacgc cgacggcaag gtcgcggcgt acggggcctt cgtgtacgag      300
```

```
cagtcgtgga ccaacacccg cgagctcgtg tccttcgcgc cggccagctg a         351
```

<210> SEQ ID NO 16
<211> LENGTH: 94
<212> TYPE: PRT
<213> ORGANISM: Zea mays (CC6)

<400> SEQUENCE: 16

```
Gly Gln Pro Leu Ala Gly Gly Trp Ser Pro Ile Arg Asn Val Ser Asp
1               5                   10                  15

Pro His Ile Gln Glu Leu Gly Gly Trp Ala Val Thr Glu His Val Arg
            20                  25                  30

Arg Ala Asn Asp Gly Leu Arg Phe Gly Glu Val Thr Gly Gly Glu Glu
        35                  40                  45

Gln Val Val Ser Gly Met Asn Tyr Lys Leu Val Leu Asp Ala Thr Asp
    50                  55                  60

Ala Asp Gly Lys Val Ala Ala Tyr Gly Ala Phe Val Tyr Glu Gln Ser
65                  70                  75                  80

Trp Thr Asn Thr Arg Glu Leu Val Ser Phe Ala Pro Ala Ser
                85                  90
```

<210> SEQ ID NO 17
<211> LENGTH: 324
<212> TYPE: DNA
<213> ORGANISM: Nicotiana alata (NaPIN1A)

<400> SEQUENCE: 17

```
atggtgaagt ttgctcacgt cgttgctttc ttgcttcttg catcacttat tcaaccctc      60 actgctcgag atttggaaat caatgttttg caacttgatg tgtctcagtc tggttgccca    120
ggagtgacaa aggaaagatg gccagaactt cttggaacac cagctaagtt tgctatgcaa    180
ataattcaga aggaaaatcc aaaactaact aatgttcaaa ctatactgaa tggtcgtcct    240
gttacagaag atttaagatg taatcgagtt cgtcttttg ttaatgtatt ggactttgtt     300
gtacaaactc cccaggttgg ctaa                                            324
```

<210> SEQ ID NO 18
<211> LENGTH: 72
<212> TYPE: PRT
<213> ORGANISM: Nicotiana alata (NaPin1A)

<400> SEQUENCE: 18

```
Gln Ser Gly Cys Pro Gly Val Thr Lys Glu Arg Trp Pro Glu Leu Leu
1               5                   10                  15

Gly Thr Pro Ala Lys Phe Ala Met Gln Ile Ile Gln Lys Glu Asn Pro
            20                  25                  30

Lys Leu Thr Asn Val Gln Thr Ile Leu Asn Gly Arg Pro Val Thr Glu
        35                  40                  45

Asp Leu Arg Cys Asn Arg Val Arg Leu Phe Val Asn Val Leu Asp Phe
    50                  55                  60

Val Val Gln Thr Pro Gln Val Gly
65                  70
```

<210> SEQ ID NO 19
<211> LENGTH: 285
<212> TYPE: DNA
<213> ORGANISM: Nicotiana alata (NaPin1B)

<400> SEQUENCE: 19

```
atggtgaagt tgctctcgt ggttactttc ttacttcttg catcaattt tcaacctctc    60 acggctcagt ccatttgccc aggagtgaaa aaggagacat ggccagaact tattggtgta   120
ccagctaagt tagcaaggga ataattcag aaggaaaatt caaaactaac taatgttcca   180
agtgtactga atggttctcc agtgacacaa gatttgagat gtgatcgagt tcgtcttttt   240
gttaatttgt tggactttgt tgtacaaatt ccccaggttg gctaa                  285
```

<210> SEQ ID NO 20
<211> LENGTH: 72
<212> TYPE: PRT
<213> ORGANISM: Nicotiana alata (NaPin1B)

<400> SEQUENCE: 20

```
Gln Ser Ile Cys Pro Gly Val Lys Lys Glu Thr Trp Pro Glu Leu Ile
 1               5                  10                  15

Gly Val Pro Ala Lys Leu Ala Arg Glu Ile Ile Gln Lys Glu Asn Ser
            20                  25                  30

Lys Leu Thr Asn Val Pro Ser Val Leu Asn Gly Ser Pro Val Thr Gln
        35                  40                  45

Asp Leu Arg Cys Asp Arg Val Arg Leu Phe Val Asn Leu Leu Asp Phe
    50                  55                  60

Val Val Gln Ile Pro Gln Val Gly
65                  70
```

<210> SEQ ID NO 21
<211> LENGTH: 318
<212> TYPE: DNA
<213> ORGANISM: Solanum lycopersicum var. cerasiforme (Tomdef2)

<400> SEQUENCE: 21

```
atggctcgtt ccatttctt catggcattt ttggtcttgg caatgatgct ctttgttacc    60
tatgaggtag aagctcagca aatttgcaaa gcaccaagcc aaactttccc aggattatgt   120
tttatggact catcatgtag aaaatattgt atcaaagaga aatttactgg tggacattgt   180
agcaaactcc aaaggaagtg tctatgcact aagccatgtg tatttgacaa aatctcaagt   240
gaagttaaag caactttggg tgaggaagca aaaactctaa gtgaagttgt gcttgaagaa   300
gagattatga tggagtaa                                                 318
```

<210> SEQ ID NO 22
<211> LENGTH: 48
<212> TYPE: PRT
<213> ORGANISM: Solanum lycopersicum var. cerasiforme (Tomdef2)

<400> SEQUENCE: 22

```
Gln Gln Ile Cys Lys Ala Pro Ser Gln Thr Phe Pro Gly Leu Cys Phe
 1               5                  10                  15

Met Asp Ser Ser Cys Arg Lys Tyr Cys Ile Lys Glu Lys Phe Thr Gly
            20                  25                  30

Gly His Cys Ser Lys Leu Gln Arg Lys Cys Leu Cys Thr Lys Pro Cys
        35                  40                  45
```

<210> SEQ ID NO 23
<211> LENGTH: 306
<212> TYPE: DNA
<213> ORGANISM: Petunia hybrida (PhD1A)

<400> SEQUENCE: 23

```
atggctcgct ccatctgttt cttcgcagtt gctacactgg cattgatgct ctttgctgcc    60
tatgaggcgg aagcggcaac ttgcaaggct gaatgcccaa cttgggatgg aatatgtata   120
aataaaggcc catgtgtaaa atgttgcaaa gcacaaccag aaaaattcac agacgggcac   180
tgcagtaaag tactccgaag atgcctatgc actaagccgt gtgcaactga agaggcaact   240
gcaactttgg ctaacgaggt aaagactatg gctgaagctt tggtcgaaga agatatgatg   300
gaataa                                                             306
```

<210> SEQ ID NO 24
<211> LENGTH: 49
<212> TYPE: PRT
<213> ORGANISM: Petunia hybrida (PhD1A)

<400> SEQUENCE: 24

```
Ala Thr Cys Lys Ala Glu Cys Pro Thr Trp Asp Gly Ile Cys Ile Asn
1               5                   10                  15

Lys Gly Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
        35                  40                  45

Cys
```

<210> SEQ ID NO 25
<211> LENGTH: 58
<212> TYPE: PRT
<213> ORGANISM: Bos taurus (BTIP)

<400> SEQUENCE: 25

```
Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55
```

<210> SEQ ID NO 26
<211> LENGTH: 25
<212> TYPE: DNA
<213> ORGANISM: Artificial Sequence
<220> FEATURE:
<223> OTHER INFORMATION: synthetic primer jrf1

<400> SEQUENCE: 26

```
aaggatccat ggcaacacta ggagg                                         25
```

<210> SEQ ID NO 27
<211> LENGTH: 25
<212> TYPE: DNA
<213> ORGANISM: Artificial Sequence
<220> FEATURE:
<223> OTHER INFORMATION: synthetic construct: primer jrf2

<400> SEQUENCE: 27

```
aaggatccat ggcaaatcta ggagg                                         25
```

<210> SEQ ID NO 28
<211> LENGTH: 26
<212> TYPE: DNA

```
<213> ORGANISM: Artificial Sequence
<220> FEATURE:
<223> OTHER INFORMATION: syntehtic construct: primer jrr1

<400> SEQUENCE: 28
aagtgcactt aagcactagy ggcatc                                         26

<210> SEQ ID NO 29
<211> LENGTH: 29
<212> TYPE: DNA
<213> ORGANISM: Artificial Sequence
<220> FEATURE:
<223> OTHER INFORMATION: synthetic construct: primer jrf3

<400> SEQUENCE: 29
ctccgcggtg gtatggcaac actaggagg                                      29

<210> SEQ ID NO 30
<211> LENGTH: 26
<212> TYPE: DNA
<213> ORGANISM: Artificial Sequence
<220> FEATURE:
<223> OTHER INFORMATION: synthetic construct: primer jrf4

<400> SEQUENCE: 30
ctccgcggta tggcaaatct aggagg                                         26

<210> SEQ ID NO 31
<211> LENGTH: 35
<212> TYPE: DNA
<213> ORGANISM: Artificial Sequence
<220> FEATURE:
<223> OTHER INFORMATION: synthetic construct: primer HvCys6F

<400> SEQUENCE: 31
gctccgcggt ggtatgcaga agaactcgac catgg                               35

<210> SEQ ID NO 32
<211> LENGTH: 22
<212> TYPE: DNA
<213> ORGANISM: Artificial Sequence
<220> FEATURE:
<223> OTHER INFORMATION: syntehtic construct: primer HvCys6R

<400> SEQUENCE: 32
ggagctctta gccgccggca gc                                             22

<210> SEQ ID NO 33
<211> LENGTH: 34
<212> TYPE: DNA
<213> ORGANISM: Artificial Sequence
<220> FEATURE:
<223> OTHER INFORMATION: synthetic construct: primer CC6F

<400> SEQUENCE: 33
gctccgcggt ggtatgtccg cgagagctct tctc                                34

<210> SEQ ID NO 34
<211> LENGTH: 26
<212> TYPE: DNA
<213> ORGANISM: Artificial Sequence
<220> FEATURE:
<223> OTHER INFORMATION: synthetic construct: primer CC6R

<400> SEQUENCE: 34
ggagctctca gctggccggc gcgaag                                         26
```

<210> SEQ ID NO 35
<211> LENGTH: 27
<212> TYPE: DNA
<213> ORGANISM: Artificial Sequence
<220> FEATURE:
<223> OTHER INFORMATION: synthetic construct: primer MHvCys6F2

<400> SEQUENCE: 35
gccacctcgg ccctcggccg gcgcggc                                       27

<210> SEQ ID NO 36
<211> LENGTH: 28
<212> TYPE: DNA
<213> ORGANISM: Artificial Sequence
<220> FEATURE:
<223> OTHER INFORMATION: synthetic construct: primer MHvCys6F

<400> SEQUENCE: 36
gctccgcggt ggtgccacct cggccctc                                      28

<210> SEQ ID NO 37
<211> LENGTH: 27
<212> TYPE: DNA
<213> ORGANISM: Artificial Sequence
<220> FEATURE:
<223> OTHER INFORMATION: synthetic construct: primer MCC6

<400> SEQUENCE: 37
gctccgcggt ggtgggcagc cgctcgc                                       27

<210> SEQ ID NO 38
<211> LENGTH: 21
<212> TYPE: DNA
<213> ORGANISM: Artificial Sequence
<220> FEATURE:
<223> OTHER INFORMATION: syntehtic construct: primer CC6R2

<400> SEQUENCE: 38
gggtacctca gctggccggc g                                             21

<210> SEQ ID NO 39
<211> LENGTH: 35
<212> TYPE: DNA
<213> ORGANISM: Artificial Sequence
<220> FEATURE:
<223> OTHER INFORMATION: synthetic construct: primer Sac2StPin1A5'

<400> SEQUENCE: 39
ctccgcggtg gtaaggaatc ggaatctgaa tcttg                              35

<210> SEQ ID NO 40
<211> LENGTH: 37
<212> TYPE: DNA
<213> ORGANISM: Artificial Sequence
<220> FEATURE:
<223> OTHER INFORMATION: synthetic construct: primer Pot1SalI3'

<400> SEQUENCE: 40
ggtcgactta agccacccta ggaatttgta caacatc                            37

<210> SEQ ID NO 41
<211> LENGTH: 33
<212> TYPE: DNA
<213> ORGANISM: Artificial Sequence
<220> FEATURE:

-continued

```
<223> OTHER INFORMATION: syntehtic construct: primer NaPin1Afw

<400> SEQUENCE: 41
ctccgcggtg gtcagtctgg ttgcccagga gtg                                33

<210> SEQ ID NO 42
<211> LENGTH: 36
<212> TYPE: DNA
<213> ORGANISM: Artificial Sequence
<220> FEATURE:
<223> OTHER INFORMATION: synthetic construct: primer NaPin1Arv

<400> SEQUENCE: 42
gagctcttag ccaacctggg gagtttgtac aacaaa                             36

<210> SEQ ID NO 43
<211> LENGTH: 33
<212> TYPE: DNA
<213> ORGANISM: Artificial Sequence
<220> FEATURE:
<223> OTHER INFORMATION: synthetic construct: primer NaPin1Bfw

<400> SEQUENCE: 43
ctccgcggtg gtcagtccat ttgcccagga gtg                                33

<210> SEQ ID NO 44
<211> LENGTH: 37
<212> TYPE: DNA
<213> ORGANISM: Artificial Sequence
<220> FEATURE:
<223> OTHER INFORMATION: synthetic construct: primer NaPin1Brv

<400> SEQUENCE: 44
cgagctctta gccaacctgg ggaatttgta caacaaa                            37

<210> SEQ ID NO 45
<211> LENGTH: 101
<212> TYPE: PRT
<213> ORGANISM: Petunia hybrida (PhD2:Full length)

<400> SEQUENCE: 45

Met Ala Arg Ser Ile Cys Phe Phe Ala Val Ala Ile Leu Ala Leu Met
  1               5                  10                  15

Leu Phe Ala Ala Tyr Glu Thr Glu Ala Gly Thr Cys Lys Ala Glu Cys
                 20                  25                  30

Pro Thr Trp Glu Gly Ile Cys Ile Asn Lys Ala Pro Cys Val Lys Cys
             35                  40                  45

Cys Lys Ala Gln Pro Glu Lys Phe Thr Asp Gly His Cys Ser Lys Ile
         50                  55                  60

Leu Arg Arg Cys Leu Cys Thr Lys Pro Cys Ala Thr Glu Glu Ala Thr
 65                  70                  75                  80

Ala Thr Leu Ala Asn Glu Val Lys Thr Met Ala Glu Ala Leu Val Glu
                 85                  90                  95

Glu Asp Met Met Glu
            100

<210> SEQ ID NO 46
<211> LENGTH: 49
<212> TYPE: PRT
<213> ORGANISM: Petunia hybrida (PhD2:mature domain)

<400> SEQUENCE: 46
```

-continued

```
Gly Thr Cys Lys Ala Glu Cys Pro Thr Trp Glu Gly Ile Cys Ile Asn
1               5                   10                  15

Lys Ala Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
        35                  40                  45

Cys
```